United States Patent
Duan et al.

(12)

(10) Patent No.: US 6,537,966 B1
(45) Date of Patent: Mar. 25, 2003

(54) FOLLISTATIN-3

(75) Inventors: D. Roxanne Duan, Bethesda, MD (US); Steven M. Ruben, Olney, MD (US)

(73) Assignee: Human Genome Sciences, Inc., Rockville, MD (US)

(*) Notice: Subject to any disclaimer, the term of this patent is extended or adjusted under 35 U.S.C. 154(b) by 0 days.

(21) Appl. No.: 09/617,804

(22) Filed: Jul. 14, 2000

Related U.S. Application Data

(63) Continuation of application No. 09/141,027, filed on Aug. 27, 1998, which is a continuation-in-part of application No. PCT/US98/17710, filed on Aug. 27, 1998.
(60) Provisional application No. 60/144,088, filed on Jul. 16, 1999, and provisional application No. 60/056,248, filed on Aug. 29, 1997.

(51) Int. Cl.[7] .......................... A61K 38/22; C12N 5/10; C12N 15/16; C12N 15/63

(52) U.S. Cl. .......................... 514/2; 530/350; 530/399; 530/402; 514/8; 514/12; 435/69.1; 435/69.4; 435/71.1; 435/71.2; 435/471; 435/325; 435/320.1; 435/252.3; 435/254.11

(58) Field of Search ................................ 530/350, 399, 530/402; 435/69.1, 69.4, 71.1, 71.2, 471, 325, 320.1, 252.3, 254.11; 514/2, 8, 12

(56) References Cited

U.S. PATENT DOCUMENTS 5,942,420 A    8/1999   Holtzmann

FOREIGN PATENT DOCUMENTS

| WO | WO 99/10364 A1 | 3/1999 |
|----|----------------|--------|
| WO | WO99/55865     | 4/1999 |
| WO | WO99/25371     | 5/1999 |
| WO | WO99/31237     | 6/1999 |
| WO | WO 01/05998 A1 | 1/2001 |

OTHER PUBLICATIONS

Mikayama et al. Proc. Natl. Acad. Sci USA vol. 90, pp. 10056–10060, 1993.*
Voet et al. Biochemistry John Wiley & Sons, Inc., pp. 126–128, and 228–234, 1990.*
Genbank Accession No. N52331, Hillier et al., (Jan. 30, 1997), *Genome Res.*, 6(9):807–828 (1996).
Genbank Accession No. AA552990, National Cancer Insitute, Cancer Genome Anatomy Project (Aug. 11, 1997).
Genbank Accession No. N28854, Hillier et al., The WashU–Merck EST Project (Jan. 4, 1996).
Genbank Accession No. R74502, Hillier et al., The WashU–Merck EST Project (Jun. 5, 1995).
Genbank Accession No. N75101, Hillier et al., (Jan. 30, 1997), *Genome Res.*, 6(9):807–828 (1996).
Genbank Accession No. AC004156, Lamerdin et al., Sequence analysis of a 3.5 Mb contig in human 19p13.3 containing a serine protease gene cluster (Feb. 19, 1998).
Genbank Accession No. AA375541, Adams et al., (Apr. 21, 1997), *Nature* 377(6547 Suppl):3–174 (1995).
Genbank Accession No. AA363365, Adams et al., (Apr. 21, 1997), *Nature Genet.*, 4:373–380 (1993).
Hayette et al., *Oncogene*, 16:2949–2954 (1998).
Shimasaki et al., *PNAS*, 85:4218–4222 (1988).
Genbank Accession No. AA227791, Hillier et al., Wash U.—Merck EST Project (Aug. 6, 1997).
Genbank Accession No. N32892, Hillier et al., Wash. U.—Merck EST Project (Jan. 10, 1996).
Genbank Accession No. AA470722, National Cancer Institute, Cancer Genome Anatomy Project (Aug. 14, 1997).
Genbank Accession No. AA492556, National Cancer Institute, Cancer Genome Anatomy Project (Aug. 19, 1997).
Genbank Accession No. N42037, Hillier et al., Wash. U.—Merck EST Project (Jan. 24, 1996).
Genbank Accession No. R72628, Hillier et al., Wash. U.—Merck EST Project (Jun. 2, 1995).
Genbank Accession No. H42225, Hillier et al., Wash. U.—Merck EST Project (Jul. 31, 1995).
Genbank Accession No. H24937, Hillier et al., Wash. U.-Merck EST Project (Jul. 7, 1995).
Genbank Accession No. R79389, Hillier et al., Wash. U–Merck EST Project (Jun. 9, 1995).
Genbank Accession No. H43043, Hillier et al., Wash. U–Merck EST Project (Jul. 31, 1995).
Genbank Accession No. AA227956, Hillier et al., Wash. U.—Merck EST Project (Aug. 6, 1997).
Genbank Accession No. H14559, Hillier et al., Wash. U–Merck EST Project (Jun. 27, 1995).
Genbank Accession No. AA470654, National Cancer Institute, Cancer Genome Anatomy Project (Aug. 14, 1997).
Genbank Accession No. H42566, Hillier et al., Wash. U.-Merck EST Project (Jul. 31, 1995).
Genbank Accession No. R79390, Hillier et al., Wash. U.-Merck EST Project (Jun. 9, 1995).
Genbank Accession No. R72699, Hillier et al., Wash. U.–Merck EST Project (Jun. 2, 1995).

(List continued on next page.)

*Primary Examiner*—Prema Mertz
(74) *Attorney, Agent, or Firm*—Human Genome Sciences, Inc.

(57) ABSTRACT

The present invention relates to a novel follistatin-3 protein which is a member of the family of inhibin-related proteins. In particular, isolated nucleic acid molecules are provided encoding the human follistatin-3 protein. Follistatin-3 polypeptides are also provided as are vectors, host cells and recombinant methods for producing the same. The invention further relates to screening methods for identifying agonists and antagonists of follistatin-3 activity. Also provided are diagnostic methods for detecting reproductive system-related disorders and disorders of the regulation of cell growth and differentiation and therapeutic methods for treating reproductive system-related disorders and disorders of the regulation of cell growth and differentiation.

67 Claims, 5 Drawing Sheets

OTHER PUBLICATIONS

Genbank Accession No. AA258582, Hillier et al., Wash. U.–Merck EST Project (Aug. 6, 1997).

Genbank Accession No. AA365825 (Apr. 21, 1997), Adams et al., *Nature*, 377(6547 Suppl.):3–174 (1995).

Genbank Accession No. AA020306, Marra et al., Wash. U–HHMI mouse EST Project (Jan. 21, 1997).

Genbank Accession No. H51168, Hillier et al., Wash. U.–Merck EST Project (Sep. 18, 1995).

Genbank Accession No. R46195, Hillier et al., Wash. U.–Merck EST Project (May 10, 1995).

Genbank Accession No. AA015105, Marra et al., Wash. U–HHMI mouse EST Project (Jan. 21, 1997).

Genbank Accession No. W18317, Marra et al., Wash. U–HHMI mouse EST Project (Sep. 10, 1996).

Genbank Accession No. D31566 (Feb. 8, 1995), Sudo et al., *Genomics*, 24:276–279 (1995).

Genbank Accession No. W14649, Marra et al., Wash. U–HHMI mouse EST Project (Sep. 10, 1996).

Genbank Accession No. AA568792, National Cancer Institute Cancer Genome Anatomy Project (Aug. 22, 1997).

Hemmati–Brivanlou, et al., *Cell*, 77:283–295 (1994).

Mikayama et al., *Proc. Natl. Acad. Sci. USA*, 90:10056–10060 (1993).

Voet et al., *Biochemistry*, John Wiley & Sons, Inc., pp.: 126–128 and 228–234(1990).

Online Database, Accession No. AA421552, Hillier et al. "Homo sapiens cDNA clone" (May 19, 1997).

Online Database, Accession No. AA470722, National Cancer Institute, "Homo sapiens cDNA clone" (Jun. 21, 1997).

Online Database, Accession No. AA227791, Hillier et al. "Homo sapiens cDNA clone" (Feb. 27, 1997).

European Search Report, Application No. EP 98 94 1072.5, dated Jul. 25, 2000.

\* cited by examiner

Figure 1A
Follistatin-3

```
  1 GCCGTCTCTGCGTTCGCCATGCGTCCCGGGGCGCCAGGGCCACTCTGGCCTCTGCCCTGG    60
  1                     M   R   P   G   A   P   G   P   L   W   P   L   P   W      14

61 GGGGCCCTGGCTTGGGCCGTGGGCTTCGTGAGCTCCATGGGCTCGGGGAACCCCGCGCCC   120
 15  G   A   L   A   W   A   V   G   F   V   S   S   M   G   S   N   P   A   P     34

121 GGTGGTGTTTGCTGGCTCCAGCAGGGCCAGGAGGCCACCTGCAGCCTGGTGCTCCAGACT   180
 35  G   G   V   C   W   L   Q   Q   G   Q   E   A   T   C   S   L   V   L   Q   T    54

*                                              #
181 GATGTCACCCGGGCCGAGTGCTGTGCCTCCGGCAACATTGACACCGCCTGGTCCAACCTC   240
 55  D   V   T   R   A   E   C   C   A   S   G   N   I   D   T   A   W   S   N   L    74

241 ACCCACCCGGGGAACAAGATCAACCTCCTCGGCTTCTTGGGCCTTGTCCACTGCCTTCCC   300
 75  T   H   P   G   N   K   I   N   L   L   G   F   L   G   L   V   H   C   L   P    94

301 TGCAAAGATTCGTGCGACGGCGTGGAGTGCGGCCCGGGCAAGGCGTGCCGCATGCTGGGG   360
 95  C   K   D   S   C   D   G   V   E   C   G   P   G   K   A   C   R   M   L   G   114

361 GGCCGCCCCGCGCTGCGAGTGCGCGCCCGACTGCTCGGGGCTCCCGGCGCGGTTGCAGGTC   420
115  G   R   P   R   C   E   C   A   P   D   C   S   G   L   P   A   R   L   Q   V   134

*.
421 TGCGGCTCAGACGGCGCCACCTACCGCGACGAGTGCGAGCTGCGCGCCGCGCGCTGCCGC   480
135  C   G   S   D   G   A   T   Y   R   D   E   C   E   L   R   A   A   R   C   R   154

481 GGCCACCCGGACCTGAGCGTCATGTACCGGGGCCGCTGCCGCAAGTCCTGTGAGCACGTG   540
155  G   H   P   D   L   S   V   M   Y   R   G   R   C   R   K   S   C   E   H   V   174

541 GTGTGCCCGCGGCCACAGTCGTGCGTCGTGGACCAGACGGGCAGCGCCCACTGCGTGGTG   600
175  V   C   P   R   P   Q   S   C   V   V   D   Q   T   G   S   A   H   C   V   V   194

601 TGTCGAGCGGCGCCCTGCCCTGTGCCCTCCAGCCCCGGCCAGGAGCTTTGCGGCAACAAC   660
195  C   R   A   A   P   C   P   V   P   S   S   P   G   Q   E   L   C   G   N   N   214

661 AACGTCACCTACATCTCCTCGTGCCACATGCGCCAGGCCACCTGCTTCCTGGGCCGCTCC   720
215  N   V   T   Y   I   S   S   C   H   M   R   Q   A   T   C   F   L   G   R   S   234

*
721 ATCGGCGTGCGCCACGCGGGCAGCTGCGCAGGCACCCCTGAGGAGCCGCCAGGTGGTGAG   780
235  I   G   V   R   H   A   G   S   C   A   G   T   P   E   E   P   P   G   G   E   254

*
781 TCTGCAGAAGAGGAAGAGAACTTCGTGTGAGCCTGCAGGACAGGCCTGGGCCTGGTGCCC   840
255  S   A   E   E   E   E   N   F   V                                               263
```

Figure 1B
Follistatin-3

```
 841  GAGGCCCCCCATCATCCCCTGTTATTTATTGCCACAGCAGAGTCTAATTTATATGCCACG   900

901  GACACTCCTTAGAGCCCGGATTCGGACCACTTGGGGATCCCAGAACCTCCCTGACGATAT   960

961  CCTGGAAGGACTGAGGAAGGGAGGCCTGGGGGCCGGCTGGTGGGTGGGATAGACCTGCGT  1020

1021  TCCGGACACTGAGCGCCTGATTTAGGGCCCTTCTCTAGGATGCCCCAGCCCCTACCCTAA  1080

1081  GACCTATTGCCGGGGAGGATTCCACACTTCCGCTCCTTTGGGGATAAACCTATTAATTAT  1140

1141  TGCTACTATCAAGAGGGCTGGGCATTCTCTGCTGGTAATTCCTGAAGAGGCATGACTGCT  1200

1201  TTTCTCAGCCCCAAGCCTCTAGTCTGGGTGTGTACGGAGGGTCTAGCCTGGGTGTGTACG  1260

1261  GAGGGTCTAGCCTGGGTGAGTACGGAGGGTCTAGCCTGGGTGAGTACGGAGGATCTAGCC  1320

1321  TGGGTGAGTACGGAGAGTCTAGCCTGGGTGTGTATGGAGGATCTAGCCTGGGTGAGTATG  1380

1381  GAGGGTCTAGCCTGGGTGAGTATGGAGGGTCTAGCCTGGGTGTGTATGGAGGGTCTAGCC  1440

1441  TGGGTGAGTATGGAGGGTCTAGCCTGGGTGTGTATGGAGGGTCTAGCCTGGGTGAGTATG  1500

1501  GAGGGTCTAGCCTGGGTGTGTACGGAGGGTCTAGTCTGAGTGCGTGTGGGGACCTCAGAA  1560

1561  CACTGTGACCTTAGCCCAGCAAGCCAGGCCCTTCATGAAGGCCAAGAAGGCTGCCACCAT  1620

1621  TCCCTGCCAGCCCAAGAACTCCAGCTTCCCCACTGCCTCTGTGTGCCCCTTTGCGTCCTG  1680

1681  TGAAGGCCATTGAGAAATGCCCAGTGTGCCCCCTGGGAAAGGGCACGGCCTGTGCTCCTG  1740

1741  ACACGGGCTGTGCTTGGCCACAGAACCACCCAGCGTCTCCCCTGCTGCTGTCCACGTCAG  1800

1801  TTCATGAGGCAACGTCGCGTGGTCTCAGACGTGGAGCAGCCAGCGGCAGCTCAGAGCAGG  1860

1861  GCACTGTGTCCGGCGGAGCCAAGTCCACTCTGGGGGAGCTCTGGCGGGACCACGGGCCA  1920

1921  CTGCTCACCCACTGGCCCCGAGGGGGTGTAGACGCCAAGACTCACGCATGTGTGACATC  1980

1981  CGGAGTCCTGGAGCCGGGTGTCCCAGTGGCACCACTAGGTGCCTGCTGCCTCCACAGTGG  2040
```

Figure 1C
Follistatin-3

```
2041  GGTTCACACCCAGGGCTCCTTGGTCCCCCACAACCTGCCCCGGCCAGGCCTGCAGACCCA  2100

2101  GACTCCAGCCAGACCTGCCTCACCCACCAATGCAGCCGGGGCTGGCGACACCAGCCAGGT  2160

2161  GCTGGTCTTGGGCCAGTTCTCCCACGACGGCTCACCCTCCCCTCCATCTGCGTTGATGCT  2220

2221  CAGAATCGCCTACCTGTGCCTGCGTGTAAACCACAGCCTCAGACCAGCTATGGGGAGAGG  2280

2281  ACAACACGGAGGATATCCAGCTTCCCCGGTCTGGGGTGAGGAGTGTGGGGAGCTTGGGCA  2340

2341  TCCTCCTCCAGCCTCCTCCAGCCCCCAGGCAGTGCCTTACCTGTGGTGCCCAGAAAAGTG  2400

2401  CCCCTAGGTTGGTGGGTCTACAGGAGCCNCAGCCAGGCAGCCCACCCCACCCTGGGGCCC  2460

2461  TGCCTCACCAAGGAAATAAAGACTCAAAGAAGCCT  2495
```

Figure 2

Percent Similarity: 61.508    Percent Identity: 43.254

Follistatin3.aa
x
Follistatin1.aa

```
  7 GPLWPLPWGALAWAVGFVSSMGSGNPAPGGVCWLQQGQEATCSLVLQTDV  56
    .. :. |  |:|.: : ::: : .:..|.:|  |||.|:.::  |  :::..|::
  2 VRARHQP.GGLCLLLLLLCQFMEDRSAQAGNCWLRQAKNGRCQVLYKTEL  50

57 TRAECCASGNIDTAWSNLTHPGNKINLLGFL....GLVHCLPCKDSCDGV 102
    .:.|||..|.:.|.|.:    ...|..|: ::      |  .:|:|||:.|:.|
 51 SKEECCSTGRLSTSWTE..EDVNDNTLFKWMIFNGGAPNCIPCKETCENV  98

103 ECGPGKACRM.LGGRPRCECAPDCSGLPARLQVCGSDGATYRDECELRAA 151
    :|||||  |||    .:|||  ||||||.:.  :  .|||  ||  |||:||.|   |
 99 DCGPGKKCRMNKKNKPRCVCAPDCSNITWKGPVCGLDGKTYRNECALLKA 148

152 RCRGHPDLSVMYRGRCRKSCEHVVCPRPQSCVVDQTGSAHCVVCRAAPCP 201
    ||:::|:|.|  |.|||:|.|  .|.||  . .||||||..|.||.|.    ||
149 RCKEQPELEVQYQGRCKKTCRDVFCPGSSTCVVDQTNNAYCVTCNRI.CP 197

202 VPSSPGQELCGNNNVTYISSCHMRQATCFLGRSIGVRHAGSC..AGTPEE 249
    |.|.:|  ||||:.|||  |.||:|.|||:||||||:  ..|.|   |  ..|:
198 EPASSEQYLCGNDGVTYSSACHLRKATCLLGRSIGLAYEGKCIKAKSCED 247

250 PPGGESAEEEENF 262
    ...:: .     :|
248 IQCTGGKKCLWDF 260
```

Follistatin-3

FOLLISTATIN-3

This application claims benefit under 35 U.S.C. § 119(e) of the filing date of copending U.S. Provisional Application Ser. No. 60/144,088, filed Jul. 16, 1999, which is hereby incorporated by reference in its entirety. This application is a continuation of U.S. application Ser. No. 09/141,027 filed Aug. 27, 1998, which in turn claims benefit of priority under 35 U.S.C. § 119(e) to U.S. Provisional Application Ser. No. 60/056,248, filed Aug. 29, 1997; each of which is hereby incorporated by reference in its entirety. This application is a C-I-P of PCT Application Ser. No. PCT/US98/17710, filed Aug. 27, 1998, which is hereby incorporated by reference in its entirety.

FIELD OF THE INVENTION

The present invention relates to a novel human gene encoding a polypeptide which is a member of the family of inhibin-related proteins. More specifically, isolated nucleic acid molecules are provided encoding a human polypeptide named follistatin-3. Follistatin-3 polypeptides are also provided, as are vectors, host cells and recombinant methods for producing the same. Also provided are diagnostic methods for detecting disorders related to the reproductive system, and therapeutic methods for treating such disorders. The invention further relates to screening methods for identifying agonists and antagonists of follistatin-3 activity.

BACKGROUND OF THE INVENTION

The family of inhibin-related proteins currently consists of at least four groups of members: inhibins, activins, and two splice variants of follistatin-1 (315 and 288 amino acids). Inhibins and activins are members of the transforming growth factor (TGF)-beta superfamily and function with opposing actions in a variety of capacities in paracrine and autocrine regulation of both reproductive and nonreproductive organs including the liver, kidney, adrenal glands, bone marrow, placenta, anterior pituitary, and brain (Ying, S. Y., et al., *Proc. Soc. Exp. Biol. Med.* 214:114–122 (1997); Mather, J. P., et al., *Proc. Soc. Exp. Biol. Med.* 215:209–222 (1997)). Although the follistatins are not closely related to the TGF-beta family, they still play a major role in the follical stimulating hormone (FSH) synthetic pathway by increasing estradiol production and by functioning directly as high affinity activin-binding proteins. Inhibins, activins, and follistatin-1 were all initially identified as regulators of pituitary FSH secretion, but have more recently been further characterized to function as growth factors, embryo modulators, and immune factors (Petraglia, F. *Placenta* 18:3–8 (1997)). In addition, each of these factors is involved with the regulation of gonadotropin biosynthesis and secretion, ovarian and placental steroidogenesis, and oocyte and spermatogonial maturation (Halvorson, L. M. and DeCherney, A. H. *Fertil. Steril.* 65:459–469 (1996)).

FSH is a vital component of the regulatory cascade governing development of human oocytes. Primary oocytes in newborns are arrested in the prophase stage of Meiosis I and are surrounded by a 1–2 cell thick layer of follicle cells constituting a structure termed the primordial follicle. In concert with other factors, stimulation of the primordial follicle with FSH initiates its progression to the more complex structures designated the developing and antral follicles (Ueno, N., et al., *Proc. Natl. Acad. Sci. USA* 84:8282–8286 (1987); Robertson, D. M., et al., *Biochem. Biophys. Res. Comm.* 149:744–749 (1987)). The antral follicle consists of an enlarged oocyte surrounded by an increased number of follicle cells, a zona pellucida, cortical granules, and a fluid-filled cavity termed the antrum. It is in this state that thousands of developing oocytes are maintained until puberty. Each month following this point, a surge in the local concentration of several additional hormones and other factors, primarily leuteinizing hormone (LH), stimulates accelerates the growth of roughly 15–20 of the developing follicles in the ovary. Only one of these structures will ultimately complete the developmental progression of its enclosed oocyte to the metaphase stage of Meiosis 11. The single stimulated follicle will then continue to enlarge until it bursts at the surface of the ovary and releases the oocyte, still surrounded with a coating of follicle cells, for potential fertilization (Bornslaeger, E. A., et al., *Dev. Biol.* 114:453–462 (1986); Masui, Y. and Clarke, H. J. *Int. Rev. Cytol.* 57:185–282 (1979); Richards, J. S. *Recent Prog. Horm. Res.* 35:343–373 (1979)).

Follistatin also plays a central role in the above-described process of follicle development. Follistatin binds stoichiometrically to activins and, as a result, inhibits the activin-induced augmentation of FSH-release from cultured pituitary cells (Kogawa, K., et al., *Endocrinology* 128:1434–1440 (1991)). Further evidencing a feedback 5 mechanism, cultured granulosa cells produce and secrete follistatin in response to treatment with FSH (Saito, S., et al., *Biochem. Biophys. Res. Comm.* 176:413–422 (1991); Klein, R., et al., *Endocrinology* 128:1048–1056 (1991)). Furthermore, it has been determined by synthesizing the results of a number of studies, that follistatin, activin, FSH, LH, and other factors function in concert in a variety of interrelated mechanisms to regulate many developmental processes, including the development of follicles. For example, in the presence of FSH, activin can augment both LH receptor expression and progesterone production by rat granulosa cells (Sugino, H., et al., *Biochem. Biophys. Res. Comm.* 153:281–288 (1988)). In addition, activin can significantly enhance the ability of granulosa cells to express FSH receptor and produce inhibin even in the absence of FSH (Nakamura, T., et al., *Biochim. Biophys. Acta* 1135:103–109 (1992); Sugino, H., et al., supra; Hasegawa, Y., et al., *Biochem. Biophys. Res. Comm.* 156:668–674 (1988)). These and other studies provide support for the idea that follistatin and activin play important roles in the regulation of granulosa cellular differentiation.

In addition to the many well-characterized effects which follistatin, activin, and inhibin elicit on the regulation of various developmental processes in the reproductive system, a large number of studies have more recently begun to define regulatory roles for these molecules in a variety of other tissues and systems. For example, during early embryonic development in Xenopus laevis, the action of activin A in developing targets of ciliary ganglion neurons is regulated by localized expression of follistatin (Hemmati-Brivanlou, A. and Melton, D. A. *Nature* 359:609–614 (1992); Hemmati-Brivanlou, A. and Melton, D. A. *Cell* 77:273–281 (1994)). In addition, overexpression of follistatin leads to induction of neural tissue (Hemmati-Brivanlou, A., et al., *Cell* 77:283–295 (1994)). In the mouse, follistatin mRNA is first detected on embryonic day 5.5 in the deciduum, and, subsequently, in the developing hindbrain, somites, vibrissae, teeth, epidermis, and muscle (van den Eihnden-van Raaij, A. J. M., et al., *Dev. Biol.* 154:356–365 (1992); Albano, R. M., et al., *Development* 120:803–813 (1994); Feijen, A., et al, *Development* 120:3621–3637(1994)). Evidence of the relative importance of such a varied expression of follistatin is provided by Matzuk and colleagues (*Nature* 374:360–363 (1995)) who demonstrate that follistatin-deficient mice are retarded in their growth, have decreased mass of the diaphragm and intercostal muscles, shiny taut skin, skeletal defects of the hard palate and the thirteenth pair of fibs, their whisker and tooth development is abnormal, they fail to breathe, and die within hours of birth. Since the defects in mice deficient in follistatin are far more widespread than in mice deficient in activin, Matzuk and coworkers (supra) suggest that follistatin may modulate the cell growth and differentiation regulatory actions of additional members of the TGF-beta superfamily.

Thus, there is a need for polypeptides that function as regulators of reproductive development, embryonic development, and cell growth and differentiation since disturbances of such regulation may be involved in disorders relating to reproduction and the regulation of cell growth and differentiation. Therefore, there is a need for identification and characterization of such human polypeptides which can play a role in detecting, preventing, ameliorating or correcting such disorders.

SUMMARY OF THE INVENTION

The present invention provides isolated nucleic acid molecules comprising a polynucleotide encoding at least a portion of the follistatin-3 polypeptide having the complete amino acid sequence shown in SEQ ID NO:2 or the complete amino acid sequence encoded by the cDNA clone deposited as plasmid DNA as ATCC® Deposit Number 209199 on Aug. 8, 1997. The nucleotide sequence determined by sequencing the deposited follistatin-3 clone, which is shown in FIGS. 1A, 1B, and 1C (SEQ ID NO:1), contains an open reading frame encoding a complete polypeptide of 263 amino acid residues, including an initiation codon encoding an N-terminal methionine at nucleotide positions 19–21, and a predicted molecular weight of about 27.7 kDa. Nucleic acid molecules of the invention include those encoding the complete amino acid sequence excepting the N-terminal methionine shown in SEQ ID NO:2, or the complete amino acid sequence excepting the N-terminal methionine encoded by the cDNA clone in ATCC® Deposit Number 209199, which molecules also can encode additional amino acids fused to the N-terminus of the follistatin-3 amino acid sequence.

Thus, one aspect of the invention provides an isolated nucleic acid molecule comprising a polynucleotide comprising a nucleotide sequence selected from the group consisting of: (a) a nucleotide sequence encoding the follistatin-3 polypeptide having the complete amino acid sequence in SEQ ID NO:2 (i.e., positions –26 to 237 of SEQ ID NO:2); (b) a nucleotide sequence encoding the follistatin-3 polypeptide having the complete amino acid sequence in SEQ ID NO:2 excepting the N-terminal methionine (i.e., positions –25 to 237 of SEQ ID NO:2); (c) a nucleotide sequence encoding the predicted mature follistatin-3 polypeptide having the amino acid sequence at positions 1 to 237 in SEQ ID NO:2; (d) a nucleotide sequence encoding the follistatin-3 polypeptide having the complete amino acid sequence encoded by the cDNA clone contained in ATCC® Deposit No. 209199; (e) a nucleotide sequence encoding the follistatin-3 polypeptide having the complete amino acid sequence excepting the N-terminal methionine encoded by the cDNA clone contained in ATCC® Deposit No. 209199; (f) a nucleotide sequence encoding the mature follistatin-3 polypeptide having the amino acid sequence encoded by the cDNA clone contained in ATCC® Deposit No. 209199; and (g) a nucleotide sequence complementary to any of the nucleotide sequences in (a), (b), (c), (d), (e) or (f) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f) or (g), above, or a polynucleotide which hybridizes under stringent hybridization conditions to a polynucleotide in (a), (b), (c), (d), (e), (f) or (g), above. This polynucleotide which hybridizes does not hybridize under stringent hybridization conditions to a polynucleotide having a nucleotide sequence consisting of only A residues or of only T residues.

An additional nucleic acid embodiment of the invention relates to an isolated nucleic acid molecule comprising a polynucleotide which encodes the amino acid sequence of an epitope-bearing portion of a follistatin-3 polypeptide having an amino acid sequence in (a), (b), (c), (d), (e) or (f), above. A further embodiment of the invention relates to an isolated nucleic acid molecule comprising a polynucleotide which encodes the amino acid sequence of a follistatin-3 polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polynucleotide which encodes the amino acid sequence of a follistatin-3 polypeptide to have an amino acid sequence which contains not more than 10, 9, 8, 7, 6, 5, 4, 3, 2 or 1 amino acid substitutions. Conservative substitutions are preferable.

The present invention also relates to recombinant vectors, which include the isolated nucleic acid molecules of the present invention, and to host cells containing the recombinant vectors, as well as to methods of making such vectors and host cells and for using them for production of follistatin-3 polypeptides or peptides by recombinant techniques.

In accordance with a further aspect of the present invention, there is provided a process for producing such polypeptide by recombinant techniques comprising culturing recombinant prokaryotic and/or eukaryotic host cells, containing a follistatin-3 nucleic acid sequence, under conditions promoting expression of said protein and subsequent recovery of said protein.

The invention further provides an isolated follistatin-3 polypeptide comprising an amino acid sequence selected from the group consisting of: (a) the amino acid sequence of the full-length follistatin-3 polypeptide having the complete amino acid sequence shown in SEQ ID NO:2 (i.e., positions –26 to 237 of SEQ ID NO:2); (b) the amino acid sequence of the full-length follistatin-3 polypeptide having the complete amino acid sequence shown in SEQ ID NO:2 excepting the N-terminal methionine (i.e., positions –25 to 237 of SEQ ID NO:2); (c) the amino acid sequence of the predicted mature follistatin-3 polypeptide having the amino acid sequence at positions 1 to 237 in SEQ ID NO:2; (d) the amino acid sequence of the full-length follistatin-3 polypeptide having the complete amino acid sequence encoded by the cDNA clone contained in ATCC® Deposit No. 209199; (e) the amino acid sequence of the full-length follistatin-3 polypeptide having the complete amino acid sequence excepting the N-terminal methionine encoded by the cDNA clone contained in ATCC® Deposit No. 209199; and (f) the amino acid sequence of the mature follistatin-3 polypeptide having the amino acid sequence encoded by the cDNA clone contained in ATCC® Deposit No. 209199. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e) or (f) above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a follistatin-3 polypeptide having an amino acid sequence described in (a), (b), (c), (d), (e) or (f) above. Peptides or polypeptides having the amino acid sequence of an epitope-bearing portion of a follistatin-3 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

A further embodiment of the invention relates to a polypeptide which comprises the amino acid sequence of a follistatin-3 polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of a follistatin-3 polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIGS. 1A and 1B, FIGS. 2A and 2B, or fragments thereof (e.g., the mature form and/or other fragments described herein), is 1–5, 5–10, 5–25, 5–50, 10–50 or 50–150, conservative amino acid substitutions are preferable.

In another embodiment, the invention provides an isolated antibody that binds specifically to a follistatin-3 polypeptide having an amino acid sequence described in (a), (b), (c), (d), (e) or (f) above. The invention further provides methods for isolating antibodies that bind specifically to a follistatin-3 polypeptide having an amino acid sequence as described herein. Such antibodies are useful diagnostically or therapeutically as described below.

The invention also provides for pharmaceutical compositions comprising follistatin-3 polypeptides, particularly human follistatin-3 polypeptides, which may be employed, for instance, to treat cancers and other cellular growth and differentiation disorders, as well as disorders of the reproductive system. Methods of treating individuals in need of follistatin-3 polypeptides are also provided.

The invention further provides compositions comprising a follistatin-3 polynucleotide or a follistatin-3 polypeptide for administration to cells in vitro, to cells ex vivo and to cells in vivo, or to a multicellular organism. In certain particularly preferred embodiments of this aspect of the invention, the compositions comprise a follistatin-3 polynucleotide for expression of a follistatin-3 polypeptide in a host organism for treatment of disease. Particularly preferred in this regard is expression in a human patient for treatment of a dysfunction associated with aberrant endogenous activity of follistatin-3.

The present invention also provides a screening method for identifying compounds capable of enhancing or inhibiting a biological activity of the follistatin-3 polypeptide, which involves contacting a ligand which is inhibited by the follistatin-3 polypeptide with the candidate compound in the presence of a follistatin-3 polypeptide, assaying receptor-binding activity of the ligand in the presence of the candidate compound and of follistatin-3 polypeptide, and comparing the ligand activity to a standard level of activity, the standard being assayed when contact is made between the ligand itself in the presence of the follistatin-3 polypeptide and the absence of the candidate compound. In this assay, an increase in ligand activity over the standard indicates that the candidate compound is an agonist of follistatin-3 activity and a decrease in ligand activity compared to the standard indicates that the compound is an antagonist of follistatin-3 activity.

In another aspect, a screening assay for agonists and antagonists is provided which involves determining the effect a candidate compound has on follistatin-3 binding to activin or an activin-like molecule. In particular, the method involves contacting the activin or an activin-like molecule with a follistatin-3 polypeptide and a candidate compound and determining whether follistatin-3 polypeptide binding to the activin or an activin-like molecule is increased or decreased due to the presence of the candidate compound. In this assay, an increase in binding of follistatin-3 over the standard binding indicates that the candidate compound is an agonist of follistatin-3 binding activity and a decrease in follistatin-3 binding compared to the standard indicates that the compound is an antagonist of follistatin-3 binding activity.

It has been discovered that follistatin-3 is expressed not only in Hodgkin's Lymphoma but also in synovial fibroblasts, gall bladder, resting and serum-induced smooth muscle, testes, Merkel cells, HEL cells, hippocampus, TNF-alpha- and IFN-induced epithelial cells, keratinocyte, amygdala depression, HL-60 cells, hepatoma, progesterone-treated epidermal cells, endothelial cells, HSC172 cells, epitheliold sarcoma, activated T-cells, breast lymph node, pancreatic carcinoma, fetal dura mater, fetal lung, epididymis, placenta, dendritic cells, rejected kidney, and uterine cancer. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the reproductive system, or disorders of the regulation of cell growth and differentiation, significantly higher or lower levels of follistatin-3 gene expression may be detected in certain tissues (e.g., cancerous and wounded tissues) or bodily fluids (e.g., serum, plasma, urine, synovial fluid or spinal fluid) taken from an individual having such a disorder, relative to a "standard" follistatin-3 gene expression level, i.e., the follistatin-3 expression level in healthy tissue from an individual not having the reproductive system or regulation of cell growth and differentiation disorder. Thus, the invention provides a diagnostic method useful during diagnosis of such a disorder, which involves: (a) assaying follistatin-3 gene expression level in cells or body fluid of an individual; (b) comparing the follistatin-3 gene expression level with a standard follistatin-3 gene expression level, whereby an increase or decrease in the assayed follistatin-3 gene expression level compared to the standard expression level is indicative of disorder in the reproductive system or of a disorder of the regulation of cell growth and differentiation.

An additional aspect of the invention is related to a method for treating an individual in need of an increased level of follistatin-3 activity in the body comprising administering to such an individual a composition comprising a therapeutically effective amount of an isolated follistatin-3 polypeptide of the invention or an agonist thereof.

A still further aspect of the invention is related to a method for treating an individual in need of a decreased level of follistatin-3 activity in the body comprising, administering to such an individual a composition comprising a therapeutically effective amount of an follistatin-3 antagonist. Preferred antagonists for use in the present invention are follistatin-3-specific antibodies.

BRIEF DESCRIPTION OF THE FIGURES

FIGS. 1A, 1B, and 1C show the nucleotide sequence (SEQ ID NO:1) and deduced amino acid sequence (SEQ ID NO:2) of follistatin-3.

Figure 3:
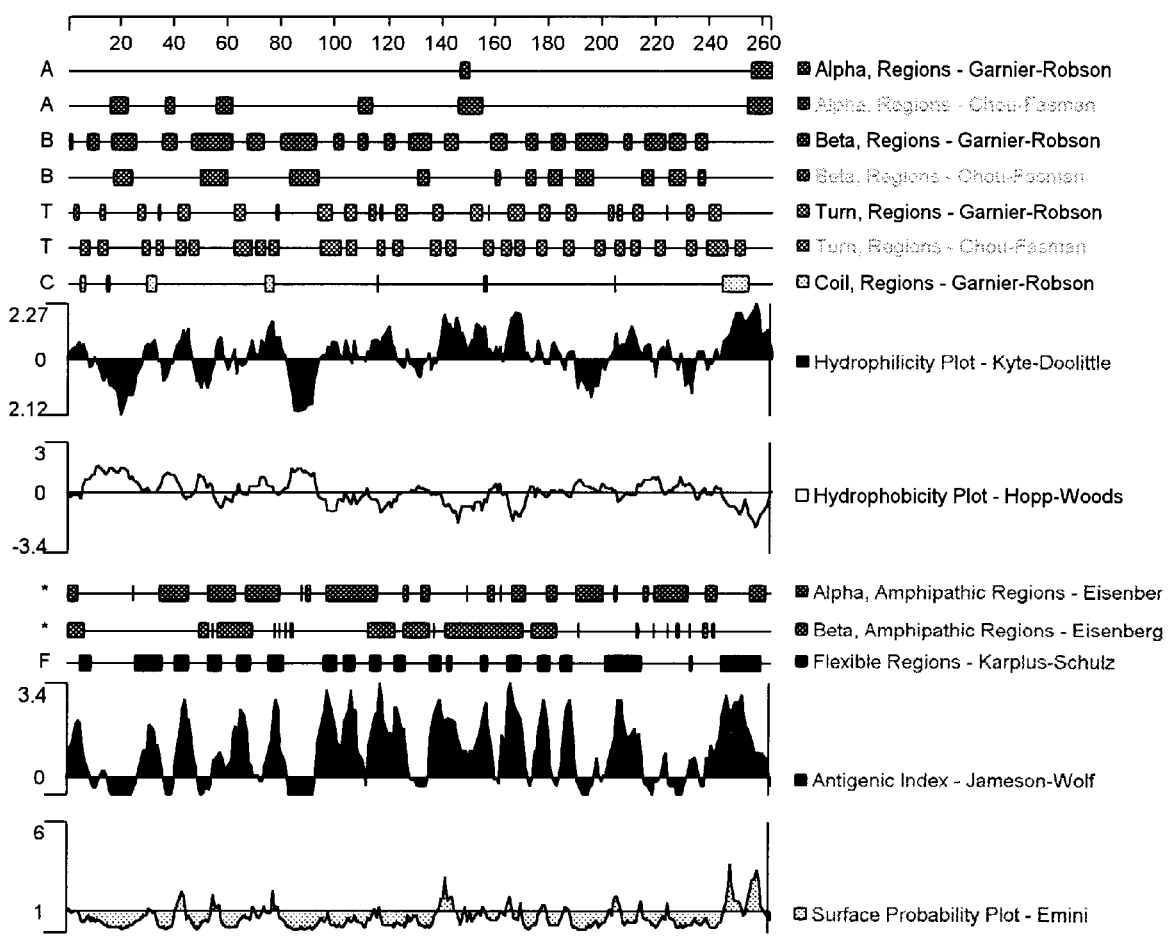

The predicted leader sequence of about 26 amino acids is underlined. Note that the methionine residue at the beginning of the leader sequence in FIG. 1A is shown in position number (positive) 1, whereas the leader positions in the corresponding sequence of SEQ ID NO:2 are designated with negative position numbers. Thus, the leader sequence positions 1 to 26 in FIG. 1A correspond to positions −26 to −1 in SEQ ID NO:2.

Two potential asparagine-linked glycosylation sites are marked in the amino acid sequence of follistatin-3. The sites are asparagine-73 and asparagine-215 in FIG. 1A (asparagine-47 and asparagine-179 in SEQ ID NO:2), and are with the bold pound symbol (#) above the nucleotide sequence coupled with a bolded one letter abbreviation for the asparagine (N) in the amino acid sequence in FIG. 1A; that is, the actual asparagine residues which are potentially glycosylated is bolded in FIG. 1A. The potential N-linked glycosylation sequences are found at the following locations in the follistatin-3 amino acid sequence: N-73 through H-76 (N-73, L-74, T-75, H-76) and N-215 through Y-218 (N-215, V-216, T-217, Y-218). A potential Protein Kinase C (PKC) phosphorylation site is also marked in FIG. 1A with a bolded tyrosine symbol (T) in the follistatin-3 amino acid sequence and an asterisk (*) above the first nucleotide encoding that tyrosine residue in the follistatin-3 nucleotide sequence. The potential PKC phosphorylation sequence is found in the follistatin-3 amino acid sequence from residue T-141 through residue R-143 (T-141, Y-142, R-143). Potential Casein Kinase II (CK2) phosphorylation sites are also marked in FIG. 1A with a bolded tyrosine or serine symbol (T or S) in the follistatin-3 amino acid sequence and an asterisk (*) above the first nucleotide encoding the appropriate tyrosine or serine residue in the follistatin-3 nucleotide sequence. Potential CK2 phosphorylation sequences are found at the following locations in the follistatin-3 amino acid sequence: T-57 through E-60 (T-57, R-58, A-59, E-60); T-141 through D-144 (T-141, Y-142, R-143, D-144); T-246 through E-249 (T-246, P-247, E-248, E-249); and S-255 through E-258 (S-255, A-256, E-257, E-258). Ten potential myristylation sites are found in the follistatin-3 amino acid sequence shown in FIG. 1A. Potential myristylation sites are marked in FIG. 1A with a double underline delineating the amino acid residues representing each potential myristolation site in the follistatin-3 amino acid sequence. The potential myristolation sites are located in the following postions in the follistatin-3 amino acid sequence: G-43 through C-48 (G-43, Q-44, E-45, A-46, T-47, C-48); G-65 through A-70 (G-65, N-66, I-67, D-68, T-69, A-70); G-78 through L-83 (G-78, N-79, K-80, I-81, N-82, L-83); G-88 through L-93 (G-88, L-89, V-90, H-91, C-92, L-93); G-136 through T-141 (G-136, S-137, D-138, G-139, A-140, T-141); G-188 through V-193 (G-188, S-189, A-190, H-191, C-192, V-193); G-207 through G-212 (G-207, Q-208, E-209, L-210, C-211, G-212); G-236 through G-241 (G-236, V-237, R-238, H-239, A-240, G-241); G-241 through T-246 (G-241, S-242, C-243, A-244, G-245, T-246); and G-252 through E-257 (G-252, G-253, E-254, S-255, A-256, E-257).

FIG. 2 shows the regions of identity between the amino acid sequences of the follistatin-3 protein and translation product of the human mRNA for follistatin-1 (SEQ ID NO:3), determined by the computer program Bestfit (Wisconsin Sequence Analysis Package, Version 8 for Unix, Genetics Computer Group, University Research Park, 575 Science Drive, Madison, Wis. 53711) using the default parameters.

FIG. 3 shows an analysis of the follistatin-3 amino acid sequence. Alpha, beta, turn and coil regions; hydrophilicity and hydrophobicity; amphipathic regions; flexible regions; antigenic index and surface probability, as predicted using default parameters, are shown.

In the "Antigenic Index or Jameson-Wolf" graph, the positive peaks indicate locations of the highly antigenic regions of the follistatin-3 protein, i.e., regions from which epitope-bearing peptides of the invention can be obtained. Non-limiting examples of antigenic polypeptides or peptides that can be used to generate follistatin-3-specific antibodies include: a polypeptide comprising amino acid residues from about Lys-54 to about Asp-62, from about Val-91 to about Leu-99, from about Lys-100 to about Gln-108, from about Cys-116 to about Pro-124, from about Gln-140 to about Leu-148, from about Trp-156 to about Ser-164, from about Arg-170, to about Gln-181, from about Cys-212 to about Phe-224, from about Tyr-239, to about Thr-247, from about Pro-251, to about Met-259, and from about Asp-263, to about His-271.

The data presented in FIG. 3 are also represented in tabular form in Table I. The columns are labeled with the headings "Res", "Position", and Roman Numerals I–XIV. The column headings refer to the following features of the amino acid sequence presented in FIG. 3 and Table I: "Res": amino acid residue of SEQ ID NO:2 or FIG. 1A (which is the identical sequence shown in SEQ ID NO:2, with the exception that the residues are numbered 1–263 in FIG. 1A and −18 through 348 in SEQ ID NO:4); "Position": position of the corresponding residue within SEQ ID NO:2 or FIGS. 2A and 2B (which is the identical sequence shown in SEQ ID NO:4, with the exception that the residues are numbered 1–366 in FIGS. 2A and 2B and −18 through 348 in SEQ ID NO:4); I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf, and XIV: Surface Probability Plot—Emini.

DETAILED DESCRIPTION

The present invention provides isolated nucleic acid molecules comprising a polynucleotide encoding a follistatin-3 polypeptide having the amino acid sequence shown in SEQ ID NO:2, which was determined by sequencing a cloned cDNA. The nucleotide sequence shown in FIGS. 1A, 1B, and 1C (SEQ ID NO:1) was obtained by sequencing the HDTAH85 clone, which was deposited on Aug. 8, 1997 at the American Type Culture Collection, 10801 University Boulevard, Manassas, Va. 20110–109, and given accession number ATCC® 209199. The deposited clone is contained in the pBluescript SK(–) plasmid (Stratagene, La Jolla, Calif.).

The follistatin-3 protein of the present invention sequence homology with the translation product of the human mRNA for follistatin-1 (FIG. 2; SEQ ID NO:3). Follistatin-1 is thought to be an important factor in the regulation of follicle development and spermatogenesis in the reproductive systems. Follistatin-1 acts as an antagonist of activin by stoichiometrically binding to activin and preventing interaction with the activin receptor. It is thought that, in addition to activin, follistatin-1 may act in a similar manner by targeting additional members of the TGF-beta superfamily.

NUCLEIC ACID MOLECULES

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A, 1B, and 1C (SEQ ID NO:1), a nucleic acid molecule of the present invention encoding a follistatin-3 polypeptide may be obtained using standard cloning and screening procedures, such as those for cloning cDNAs using mRNA as starting material. Illustrative of the invention, the nucleic acid molecule described in FIGS. 1A, 1B, and 1C (SEQ ID NO:1) was discovered in a cDNA library derived from Hodgkin's Lymphoma.

Additional clones of the same gene were also identified in cDNA libraries from the following cells and tissues: synovial fibroblasts, gall bladder, resting and serum-induced smooth muscle, testes, Merkel cells, HEL cells, hippocampus, TNF-alpha- and IFN-induced epithelial cells, keratinocyte, amygdala depression, HL-60 cells, hepatoma, progesterone-treated epidermal cells, endothelial cells, HSC172 cells, epithelioid sarcoma, activated T-cells, breast lymph node, pancreatic carcinoma, fetal dura mater, fetal lung, epididymis, placenta, dendritic cells, rejected kidney, and uterine cancer.

The determined nucleotide sequence of the follistatin-3 cDNA of FIGS. 1A, 1B, and 1C (SEQ ID NO:1) contains an open reading frame encoding a protein of 263 amino acid residues, with an initiation codon at nucleotide positions 19–21 of the nucleotide sequence in FIG. 1A (SEQ ID NO:1), and a deduced molecular weight of about 27.7 kDa. The amino acid sequence of the follistatin-3 protein shown in SEQ ID NO:2 is about 43.2% identical to human mRNA for follistatin-1 (FIG. 2; Shimasaki, S., el al., *Proc. Natl. Acad. Sci. U.S.A.* 85:4218–4222 (1988); GenBank Accession No. J03771).

The open reading frame of the follistatin-3 gene shares sequence homology with the translation product of the human mRNA for follistatin-1 (FIG. 2; SEQ ID NO:3). The homology between follistatin-1 and follistatin-3 indicates that follistatin-3 may also be involved in a physiological regulation of cell growth and differentiation, particularly with regard to cells of the reproductive system.

As one of ordinary skill would appreciate, due to the possibilities of sequencing errors discussed above, the actual complete follistatin-3 polypeptide encoded by the deposited cDNA, which comprises about 263 amino acids, may be somewhat longer or shorter. More generally, the actual open reading frame may be anywhere in the range of ±20 amino acids, more likely in the range of ±10 amino acids, of that predicted from either the methionine codon from the N-terminus shown in FIG. 1A (SEQ ID NO:1). It will further be appreciated that, depending on the analytical criteria used for identifying various functional domains, the exact "address" of the mature form of the follistatin-3 polypeptide may differ slightly from the predicted positions above. For example, the exact location of the cleavage site of the precursor form of the mature follistatin-3 molecule shown in SEQ ID NO:2 may vary slightly (e.g., the address may "shift" by about 6 residues, depending on the criteria used to define the cleavage site. In this case, the ends of the signal peptide and the beginning of the mature follistatin-3 molecule were predicted using the HGSI SignalP computer algorithm. One of skill in the art will realize that another widely accepted computer algorithm used to predict potential sites of polypeptide cleavage, PSORT, will predict the cleavage of an N-terminal signal peptide from the follistatin-3 polypeptide at a point slightly different from that predicted by the HGSI SignalP algorithm. In either case, as discussed further below, the invention further provides polypeptides having various residues deleted from the N-terminus of the complete polypeptide, including polypeptides corresponding to either of the predicted mature follistatin-3 polypeptides described herein.

The amino acid sequence of the complete follistatin-3 protein includes a leader sequence and a mature protein, as shown in SEQ ID NO:2. More in particular, the present invention provides nucleic acid molecules encoding a mature form of the follistatin-3 protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature follistatin-3 polypeptide having the amino acid sequence encoded by the cDNA clone contained in the host identified as ATCC® Deposit No. 209199. By the "mature follistatin-3 polypeptide having the amino acid sequence encoded by the cDNA clone in ATCC® Deposit No. 209199" is meant the mature form(s) of the follistatin-3 protein produced by expression in a mammalian cell (e.g., COS cells, as described below) of the complete open reading frame encoded by the human DNA sequence of the clone contained in the vector in the deposited host.

In addition, methods for predicting whether a protein has a secretory leader as well as the cleavage point for that leader sequence are available. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues –13 to +2 where +1 indicates the amino terminus of the mature protein. The accuracy of predicting the cleavage points of known mammalian secretory proteins for each of these methods is in the range of 75–80% (von Heinje, supra). However, the two methods do not always produce the same predicted cleavage point(s) for a given protein.

In the present case, the deduced amino acid sequence of the complete follistatin-3 polypeptide was analyzed by a variation of the computer program "PSORT", available from Dr. Kenta Nakai of the Institute for Chemical Research, Kyoto University (Nakai, K. and Kanehisa, M. *Genomics* 14:897–911 (1992)), which is an expert system for predicting the cellular location of a protein based on the amino acid sequence. As part of this computational prediction of localization, the methods of McGeoch and von Heinje are incorporated. Thus, the computation analysis above predicted a single cleavage site within the complete amino acid sequence shown in SEQ ID NO:2 (see above discussion).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 19–21 of the nucleotide sequence shown in FIG. 1A (SEQ ID NO:1).

Also included are DNA molecules comprising the coding sequence for the predicted mature follistatin-3 protein shown at positions 1–237 of SEQ ID NO:2.

In addition, isolated nucleic acid molecules of the invention include DNA molecules which comprise a sequence substantially different from those described above but which, due to the degeneracy of the genetic code, still encode the follistatin-3 protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding the follistatin-3 polypeptide having an amino acid sequence encoded by the cDNA clone contained in the plasmid deposited as ATCC® Deposit No. 209199 on Aug. 8, 1997.

Preferably, this nucleic acid molecule will encode the mature polypeptide encoded by the above-described deposited cDNA clone.

The invention further provides an isolated nucleic acid molecule having the nucleotide sequence shown in FIGS. 1A, 1B, and 1C (SEQ ID NO:1) or the nucleotide sequence of the follistatin-3 cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the follistatin-3 gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–810 of SEQ ID NO:1.

In addition, the invention provides nucleic acid molecules having nucleotide sequences related to extensive portions of SEQ ID NO:1 which have been determined from the following related cDNA clones: HHPDX66R (SEQ ID NO:4), HDTAH61R (SEQ ID NO:5), HSBAV55R (SEQ ID NO:6), HUKFS32R (SEQ ID NO:7), HOOAD78R (SEQ ID NO:8), HAQAG52R (SEQ ID NO:9), HTLEJ56R (SEQ ID NO:10), HLMNX90R (SEQ ID NO:11).

Further, the invention includes a polynucleotide comprising any portion of at least about 30 nucleotides, preferably at least about 50 nucleotides, of SEQ ID NO:1 from residue 1 to 500. More preferably, the invention includes a polynucleotide comprising nucleotide residues 100–500, 200–500, 300–500, 400–500, 100–400, 200–400, 300–400, 100–300, 200–300, 100–200, 100–2495, 250–2495, 500–2495, 1000–2495, 1500–2495, 2000–2495, 100–2000, 250–2000, 500–2000, 1000–2000, 1500–2000, 100–1500, 250–1500, 500–1500, 1000–1500, 100–1000, 250–1000, and 500–1000.

More generally, by a fragment of an isolated nucleic acid molecule having the nucleotide sequence of the deposited cDNA or the nucleotide sequence shown in FIGS. 1A, 1B, and 1C (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A, 1B, and 1C (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A, 1B, and 1C (SEQ ID NO:1). Preferred nucleic acid fragments of the present invention include nucleic acid molecules encoding epitope-bearing portions of the follistatin-3 polypeptide as identified in FIG. 3 and described in more detail below.

In specific embodiments, the polynucleotide fragments of the invention encode a polypeptide which demonstrates a functional activity. By a polypeptide demonstrating "functional activity" is meant, a polypeptide capable of displaying one or more known functional activities associated with a complete, mature or active form of the follistatin-3 polypeptide. Such functional activities include, but are not limited to, biological activity ((e.g., modulating the follicle stimulating hormone (FSH) synthetic pathway, increasing estradiol production, binding activin, stimulator of gonadotropin biosynthesis and secretion, regulator of ovarian and placental steroidogenesis, and oocyte and spermatogonial maturation factor)), antigenicity [ability to bind (or compete with a follistatin-3 polypeptide for binding) to an anti-follistatin-3 antibody], immunogenicity (ability to generate antibody which binds to a follistatin-3 polypeptide), the ability to form polymers with other follistatin-3 or inhibin or TGF-beta polypeptides, and ability to bind to a receptor or ligand for a follistatin-3 polypeptide.

Preferred nucleic acid fragments of the present invention also include nucleic acid molecules encoding one or more of the following domains of follistatin-3: amino acid residues 7–16, 34–45, 78–86, 91–100, 108–122, 131–145, 156–169, 184–192, and 196–210 of SEQ ID NO:2.

In specific embodiments, the polynucleotide fragments of the invention encode antigenic regions. Non-limiting examples of antigenic polypeptides or peptides that can be used to generate follistatin-3-specific antibodies include: a polypeptide comprising amino acid residues from about Leu-14 to about Ala-20, from about Ser-46 to about Ile-55, from about Gly-88 to about Pro-97, from about Gly-113 to about Leu-133, from about Arg-138 to about Glu-146, from about Pro-177 to about Thr-191, from about Gly-219 to about Val-237.

In additional embodiments, the polynucleotides of the invention encode functional attributes of follistatin-3. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of follistatin-3.

The data representing the structural or functional attributes of follistatin-3 set forth in FIG. 3 and/or Table I, as described above, was generated using the various modules and algorithms of the DNA*STAR set on default parameters. In a preferred embodiment, the data presented in columns VIII, IX, XIII, and XIV of Table I can be used to determine regions of follistatin-3 which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region.

The above-mentioned preferred regions set out in FIG. 3 and in Table I include, but are not limited to, regions of the aforementioned types identified by analysis of the amino acid sequence set out in FIGS. 1A, 1B, and 1C. As set out in FIG. 3 and in Table I, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE I

| Res | Position | I | II | III | IV | V | VI | VII | VIII | IX | X | XI | XII | XIII | XIV |
|-----|----------|---|----|----|----|---|----|----|------|-----|---|----|----|------|------|
| Met | 1  | . | .  | B  | .  | . | .  | .  | 0.31 | −0.24 | * | * | . | 1.07 | 1.11 |
| Arg | 2  | . | .  | B  | .  | . | .  | .  | 0.49 | −0.17 | * | * | . | 1.13 | 0.88 |
| Pro | 3  | . | .  | .  | .  | T | .  | .  | 0.53 | −0.17 | * | * | . | 1.89 | 1.06 |
| Gly | 4  | . | .  | .  | .  | T | .  | .  | 0.71 | −0.17 | * | * | . | 2.10 | 1.06 |
| Ala | 5  | . | .  | .  | .  | . | T  | C  | 0.29 | −0.36 | . | * | F | 1.89 | 0.84 |
| Pro | 6  | . | .  | .  | .  | . | T  | C  | 0.60 | 0.33  | . | * | F | 1.08 | 0.45 |
| Gly | 7  | . | .  | .  | .  | . | T  | C  | 0.28 | 0.81  | . | * | F | 0.57 | 0.48 |
| Pro | 8  | . | .  | B  | .  | . | T  | .  | −0.32 | 0.81 | . | . | F | 0.16 | 0.73 |
| Leu | 9  | . | .  | B  | .  | . | .  | .  | −0.19 | 1.00 | . | . | F | −0.25 | 0.39 |
| Trp | 10 | . | .  | B  | .  | . | .  | .  | 0.11 | 1.00  | . | . | . | −0.40 | 0.61 |
| Pro | 11 | . | .  | B  | .  | . | .  | .  | −0.02 | 1.49 | . | . | . | −0.40 | 0.41 |
| Leu | 12 | . | .  | B  | .  | . | T  | .  | −0.27 | 1.49 | . | . | . | −0.20 | 0.49 |
| Pro | 13 | . | .  | .  | .  | T | T  | .  | −0.87 | 1.30 | . | . | . | 0.20 | 0.48 |
| Trp | 14 | . | .  | .  | .  | T | T  | .  | −0.64 | 1.07 | . | . | . | 0.20 | 0.25 |
| Gly | 15 | . | .  | .  | .  | . | T  | C  | −0.64 | 1.14 | . | . | . | 0.00 | 0.31 |
| Ala | 16 | . | A  | .  | .  | . | .  | C  | −1.02 | 1.37 | . | . | . | −0.40 | 0.21 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 17 | . | A | B | . | . | . | . | −1.07 | 1.44 | . | . | . | −0.60 | 0.20 |
| Ala | 18 | . | A | B | B | . | . | . | −1.20 | 1.17 | . | . | . | −0.60 | 0.15 |
| Trp | 19 | . | A | B | B | . | . | . | −1.61 | 1.17 | . | . | . | −0.60 | 0.15 |
| Ala | 20 | . | A | B | B | . | . | . | −2.12 | 1.46 | . | . | . | −0.60 | 0.16 |
| Val | 21 | . | A | B | B | . | . | . | −1.83 | 1.41 | . | . | . | −0.60 | 0.11 |
| Gly | 22 | . | A | B | B | . | . | . | −1.32 | 1.30 | . | . | . | −0.60 | 0.15 |
| Phe | 23 | . | . | B | B | . | . | . | −1.33 | 0.77 | . | . | . | −0.60 | 0.19 |
| Val | 24 | . | . | B | B | . | . | . | −1.39 | 0.89 | . | . | . | −0.60 | 0.26 |
| Ser | 25 | . | . | B | . | . | . | . | −1.10 | 0.67 | * | . | . | −0.40 | 0.26 |
| Ser | 26 | . | . | B | . | . | . | . | −0.59 | 0.63 | . | . | F | −0.25 | 0.40 |
| Met | 27 | . | . | . | . | T | . | . | −0.24 | 0.27 | . | . | F | 0.45 | 0.53 |
| Gly | 28 | . | . | . | . | T | T | . | 0.24 | 0.03 | . | . | F | 0.82 | 0.64 |
| Ser | 29 | . | . | . | . | T | T | . | 0.51 | 0.07 | . | . | F | 0.99 | 0.74 |
| Gly | 30 | . | . | . | . | . | T | C | 0.60 | 0.19 | . | . | F | 0.96 | 0.76 |
| Asn | 31 | . | . | . | . | . | T | C | 0.56 | −0.00 | . | . | F | 1.88 | 1.18 |
| Pro | 32 | . | . | . | . | . | . | C | 0.81 | −0.00 | . | . | F | 1.70 | 0.87 |
| Ala | 33 | . | . | . | . | . | T | C | 0.30 | 0.04 | . | . | F | 1.13 | 0.87 |
| Pro | 34 | . | . | . | . | T | T | . | −0.07 | 0.26 | . | . | F | 1.16 | 0.40 |
| Gly | 35 | . | . | . | . | T | T | . | −0.01 | 0.43 | * | . | F | 0.69 | 0.14 |
| Gly | 36 | . | . | B | . | . | T | . | −0.82 | 0.91 | * | . | F | 0.12 | 0.15 |
| Val | 37 | . | A | B | . | . | . | . | −0.61 | 1.10 | * | . | . | −0.60 | 0.08 |
| Cys | 38 | . | A | B | . | . | . | . | −0.02 | 1.07 | * | . | . | −0.60 | 0.14 |
| Trp | 39 | . | A | B | . | . | . | . | −0.16 | 1.04 | * | . | . | −0.60 | 0.24 |
| Leu | 40 | . | A | B | . | . | . | . | 0.19 | 1.04 | * | . | . | −0.32 | 0.32 |
| Gln | 41 | . | . | B | . | . | T | . | 0.53 | 0.80 | * | . | F | 0.66 | 1.02 |
| Gln | 42 | . | . | . | . | T | T | . | 0.80 | 0.23 | * | . | F | 1.64 | 1.68 |
| Gly | 43 | . | . | . | . | T | T | . | 1.16 | −0.19 | * | . | F | 2.52 | 2.06 |
| Gln | 44 | . | . | . | . | T | T | . | 0.78 | −0.39 | * | . | F | 2.80 | 1.72 |
| Glu | 45 | . | . | . | . | T | . | . | 1.29 | −0.21 | * | . | F | 2.17 | 0.53 |
| Ala | 46 | . | . | . | . | T | T | . | 0.48 | −0.23 | * | . | F | 2.09 | 0.72 |
| Thr | 47 | . | . | B | . | . | T | . | −0.38 | 0.03 | * | . | . | 0.66 | 0.34 |
| Cys | 48 | . | . | B | . | . | T | . | −0.84 | 0.27 | * | . | . | 0.38 | 0.15 |
| Ser | 49 | . | . | B | . | . | T | . | −0.84 | 0.96 | . | . | . | −0.20 | 0.12 |
| Leu | 50 | . | . | B | B | . | . | . | −1.16 | 0.86 | . | * | . | −0.60 | 0.14 |
| Val | 51 | . | . | B | B | . | . | . | −0.57 | 0.86 | . | * | . | −0.60 | 0.39 |
| Leu | 52 | . | . | B | B | . | . | . | −1.11 | 0.29 | . | * | . | −0.30 | 0.48 |
| Gln | 53 | . | . | B | B | . | . | . | −0.76 | 0.54 | * | * | F | −0.45 | 0.43 |
| Thr | 54 | . | . | B | B | . | . | . | −0.34 | 0.34 | * | . | F | −0.15 | 0.85 |
| Asp | 55 | . | . | B | B | . | . | . | −0.12 | −0.30 | * | * | F | 0.60 | 2.01 |
| Val | 56 | . | A | B | B | . | . | . | 0.73 | −0.49 | * | . | F | 0.60 | 1.17 |
| Thr | 57 | . | A | B | B | . | . | . | 0.88 | −0.89 | * | * | F | 0.90 | 1.41 |
| Arg | 58 | . | A | B | B | . | . | . | 0.21 | −0.80 | * | * | F | 0.75 | 0.45 |
| Ala | 59 | . | A | B | B | . | . | . | −0.07 | −0.23 | * | * | . | 0.30 | 0.33 |
| Glu | 60 | . | A | B | B | . | . | . | −0.37 | −0.37 | * | * | . | 0.30 | 0.23 |
| Cys | 61 | . | A | B | . | . | . | . | 0.14 | −0.47 | * | * | . | 0.55 | 0.16 |
| Cys | 62 | . | . | . | . | T | T | . | 0.46 | −0.04 | * | * | . | 1.60 | 0.15 |
| Ala | 63 | . | . | . | . | T | T | . | −0.54 | −0.14 | * | * | . | 1.85 | 0.14 |
| Ser | 64 | . | . | . | . | T | T | . | 0.04 | 0.54 | . | * | F | 1.35 | 0.19 |
| Gly | 65 | . | . | . | . | T | T | . | −0.27 | −0.03 | . | * | F | 2.50 | 0.58 |
| Asn | 66 | . | . | . | . | T | T | . | −0.19 | −0.11 | . | * | F | 2.25 | 0.83 |
| Ile | 67 | . | . | B | . | . | T | . | 0.19 | −0.11 | * | * | F | 1.60 | 0.62 |
| Asp | 68 | . | . | B | . | . | T | . | 0.48 | 0.41 | * | * | F | 0.45 | 0.66 |
| Thr | 69 | . | . | B | . | . | T | . | 0.78 | 0.37 | * | * | F | 0.50 | 0.55 |
| Ala | 70 | . | . | B | . | . | . | . | 0.31 | 0.37 | * | * | . | 0.05 | 1.26 |
| Trp | 71 | . | . | B | . | . | T | . | −0.00 | 0.37 | * | . | . | 0.10 | 0.62 |
| Ser | 72 | . | . | B | . | . | T | . | 0.86 | 0.86 | * | . | . | −0.20 | 0.62 |
| Asn | 73 | . | . | B | . | . | T | . | 0.64 | 0.87 | * | . | . | −0.20 | 0.84 |
| Leu | 74 | . | . | . | . | . | T | C | 0.61 | 0.80 | * | . | . | 0.43 | 1.24 |
| Thr | 75 | . | . | . | . | . | . | C | 1.20 | 0.31 | * | . | . | 0.66 | 0.91 |
| His | 76 | . | . | . | . | . | T | C | 1.53 | 0.33 | * | . | F | 1.29 | 0.91 |
| Pro | 77 | . | . | . | . | . | T | C | 0.94 | −0.07 | * | . | F | 2.32 | 2.22 |
| Gly | 78 | . | . | . | . | T | T | . | 0.94 | −0.07 | * | * | F | 2.80 | 1.08 |
| Asn | 79 | . | . | . | . | T | T | . | 0.94 | −0.16 | * | . | F | 2.52 | 1.27 |
| Lys | 80 | . | . | B | . | . | . | . | 0.44 | 0.03 | * | * | F | 0.89 | 0.68 |
| Ile | 81 | . | . | B | . | . | . | . | 0.13 | 0.29 | . | . | F | 0.61 | 0.57 |
| Asn | 82 | . | . | B | . | . | . | . | −0.36 | 0.29 | . | * | . | 0.18 | 0.35 |
| Leu | 83 | . | . | B | B | . | . | . | −0.82 | 0.67 | . | . | . | −0.60 | 0.15 |
| Leu | 84 | . | . | B | B | . | . | . | −1.17 | 1.36 | . | * | . | −0.60 | 0.18 |
| Gly | 85 | . | . | B | B | . | . | . | −2.02 | 1.10 | . | * | . | −0.60 | 0.11 |
| Phe | 86 | . | . | B | B | . | . | . | −1.99 | 1.39 | . | . | . | −0.60 | 0.11 |
| Leu | 87 | . | . | B | B | . | . | . | −2.02 | 1.34 | . | . | . | −0.60 | 0.10 |
| Gly | 88 | . | . | B | B | . | . | . | −1.88 | 1.16 | * | . | . | −0.60 | 0.13 |
| Leu | 89 | . | . | B | B | . | . | . | −1.88 | 1.30 | . | . | . | −0.60 | 0.08 |
| Val | 90 | . | . | B | B | . | . | . | −1.74 | 1.20 | * | . | . | −0.60 | 0.08 |
| His | 91 | . | . | B | B | . | . | . | −1.71 | 0.94 | * | . | . | −0.60 | 0.13 |
| Cys | 92 | . | . | B | B | . | . | . | −0.86 | 1.09 | . | . | . | −0.60 | 0.08 |
| Leu | 93 | . | . | B | B | . | . | . | −0.51 | 0.40 | . | . | . | 0.01 | 0.23 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 94 | . | . | . | B | T | . | . | −0.00 | −0.24 | . | . | . | 1.32 | 0.28 |
| Cys | 95 | . | . | . | . | . | T | T | . | 0.19 | −0.36 | . | . | 2.03 | 0.70 |
| Lys | 96 | . | . | . | . | . | T | T | . | 0.22 | −0.36 | . | . | F | 2.49 | 0.46 |
| Asp | 97 | . | . | . | . | . | T | T | . | 0.54 | −1.04 | * | . | F | 3.10 | 0.49 |
| Ser | 98 | . | . | . | . | . | T | T | . | 0.50 | −1.04 | * | . | F | 2.79 | 0.91 |
| Cys | 99 | . | . | . | . | . | T | T | . | 0.71 | −0.97 | * | . | F | 2.48 | 0.34 |
| Asp | 100 | . | . | B | . | . | . | T | . | 0.71 | −0.97 | * | . | F | 1.77 | 0.35 |
| Gly | 101 | . | . | B | . | . | . | T | . | 0.32 | −0.40 | * | . | F | 1.47 | 0.14 |
| Val | 102 | . | . | B | . | . | . | T | . | 0.11 | −0.36 | * | . | . | 1.32 | 0.26 |
| Glu | 103 | . | . | B | . | . | . | . | . | 0.07 | −0.50 | * | . | . | 1.73 | 0.24 |
| Cys | 104 | . | . | . | . | T | . | . | . | 0.78 | −0.07 | * | . | F | 2.29 | 0.24 |
| Gly | 105 | . | . | . | . | T | T | . | . | 0.19 | −0.50 | * | . | F | 3.10 | 0.64 |
| Pro | 106 | . | . | . | . | T | T | . | . | −0.13 | −0.64 | * | . | F | 2.79 | 0.38 |
| Gly | 107 | . | . | . | . | T | T | . | . | 0.83 | −0.07 | * | . | F | 2.18 | 0.38 |
| Lys | 108 | . | . | . | . | T | T | . | . | 0.23 | −0.64 | * | . | F | 2.17 | 0.74 |
| Ala | 109 | . | A | B | . | . | . | . | . | 0.09 | −0.46 | * | . | . | 0.61 | 0.48 |
| Cys | 110 | . | A | B | . | . | . | . | . | 0.09 | −0.20 | * | . | . | 0.30 | 0.40 |
| Arg | 111 | . | A | B | . | . | . | . | . | −0.04 | −0.20 | * | . | . | 0.30 | 0.20 |
| Met | 112 | . | A | B | . | . | . | . | . | 0.41 | 0.23 | * | . | . | −0.30 | 0.19 |
| Leu | 113 | . | A | . | . | T | . | . | . | 0.16 | −0.27 | * | * | . | 1.04 | 0.70 |
| Gly | 114 | . | A | . | . | T | . | . | . | 0.86 | −0.41 | * | * | F | 1.53 | 0.55 |
| Gly | 115 | . | . | . | . | T | . | . | . | 0.86 | −0.41 | * | * | F | 2.22 | 1.10 |
| Arg | 116 | . | . | . | . | . | T | C | . | 0.74 | −0.46 | * | * | F | 2.41 | 0.71 |
| Pro | 117 | . | . | . | . | T | T | . | . | 0.68 | −1.14 | . | * | F | 3.40 | 1.25 |
| Arg | 118 | . | . | . | . | T | T | . | . | 0.90 | −1.00 | . | * | F | 2.91 | 0.68 |
| Cys | 119 | . | . | B | . | . | T | . | . | 1.03 | −0.93 | . | * | . | 2.02 | 0.35 |
| Glu | 120 | . | . | B | . | . | . | . | . | 1.38 | −0.50 | . | * | . | 1.73 | 0.35 |
| Cys | 121 | . | . | B | . | . | . | . | . | 0.60 | −0.93 | . | * | . | 1.64 | 0.30 |
| Ala | 122 | . | . | B | . | . | T | . | . | 0.51 | −0.36 | . | * | . | 1.45 | 0.30 |
| Pro | 123 | . | . | . | . | T | T | . | . | 0.06 | −0.54 | . | * | F | 2.55 | 0.23 |
| Asp | 124 | . | . | . | . | T | T | . | . | −0.09 | −0.11 | . | . | F | 2.50 | 0.43 |
| Cys | 125 | . | . | . | . | T | T | . | . | −0.30 | −0.00 | . | . | F | 2.25 | 0.35 |
| Ser | 126 | . | . | . | . | T | . | . | . | −0.22 | −0.07 | * | * | F | 1.80 | 0.35 |
| Gly | 127 | . | . | . | . | T | . | . | . | 0.48 | −0.00 | * | * | F | 1.55 | 0.21 |
| Leu | 128 | . | . | B | . | . | . | . | . | −0.12 | −0.00 | * | * | . | 0.75 | 0.77 |
| Pro | 129 | . | . | B | . | . | . | . | . | −0.12 | 0.11 | . | * | . | −0.10 | 0.47 |
| Ala | 130 | . | . | B | . | . | . | . | . | −0.31 | 0.13 | . | * | . | −0.10 | 0.83 |
| Arg | 131 | . | . | B | B | . | . | . | . | −0.68 | 0.34 | . | * | . | −0.30 | 0.74 |
| Leu | 132 | . | . | B | B | . | . | . | . | −0.68 | 0.23 | . | * | . | −0.30 | 0.26 |
| Gln | 133 | . | . | B | B | . | . | . | . | −0.17 | 0.23 | * | * | . | −0.30 | 0.25 |
| Val | 134 | . | . | B | B | . | . | . | . | 0.04 | 0.11 | * | * | . | −0.30 | 0.17 |
| Cys | 135 | . | . | B | B | . | . | . | . | 0.29 | 0.11 | * | * | . | −0.02 | 0.35 |
| Gly | 136 | . | . | B | . | . | T | . | . | −0.41 | −0.14 | * | * | F | 1.41 | 0.20 |
| Ser | 137 | . | . | . | . | T | T | . | . | 0.09 | −0.04 | . | . | F | 2.09 | 0.27 |
| Asp | 138 | . | . | . | . | T | T | . | . | −0.16 | −0.20 | . | * | F | 2.37 | 0.73 |
| Gly | 139 | . | . | . | . | T | T | . | . | 0.81 | −0.01 | . | . | F | 2.80 | 1.16 |
| Ala | 140 | . | . | . | . | T | . | . | . | 1.48 | −0.44 | . | . | F | 2.32 | 1.70 |
| Thr | 141 | . | . | B | . | . | . | . | . | 1.82 | −0.83 | . | . | . | 1.99 | 1.70 |
| Tyr | 142 | . | . | B | . | . | T | . | . | 1.46 | −0.83 | . | * | . | 2.11 | 2.97 |
| Arg | 143 | . | . | B | . | . | T | . | . | 1.46 | −0.69 | . | * | F | 2.18 | 1.57 |
| Asp | 144 | . | . | B | . | . | T | . | . | 0.99 | −1.19 | . | * | F | 2.10 | 1.89 |
| Glu | 145 | . | . | B | . | . | T | . | . | 1.69 | −0.99 | . | * | . | 2.00 | 0.99 |
| Cys | 146 | . | A | B | . | . | . | . | . | 1.41 | −1.74 | . | * | . | 1.40 | 0.99 |
| Glu | 147 | A | A | . | . | . | . | . | . | 1.07 | −1.24 | . | * | . | 1.20 | 0.60 |
| Leu | 148 | A | A | . | . | . | . | . | . | 1.07 | −0.74 | . | * | . | 1.00 | 0.35 |
| Arg | 149 | A | A | . | . | . | . | . | . | 0.40 | −0.74 | . | * | . | 0.95 | 1.28 |
| Ala | 150 | A | A | . | . | . | . | . | . | 0.51 | −0.74 | * | * | . | 0.60 | 0.40 |
| Ala | 151 | . | A | . | . | T | . | . | . | 0.83 | −0.74 | . | * | . | 1.00 | 0.94 |
| Arg | 152 | . | A | . | . | T | . | . | . | 0.80 | −1.00 | . | * | . | 1.00 | 0.48 |
| Cys | 153 | . | A | . | . | T | . | . | . | 1.40 | −0.50 | . | * | . | 1.27 | 0.64 |
| Arg | 154 | . | A | . | . | T | . | . | . | 1.29 | −0.57 | . | * | . | 1.54 | 0.98 |
| Gly | 155 | . | A | . | . | T | . | . | . | 1.07 | −1.07 | . | * | F | 1.96 | 0.84 |
| His | 156 | . | . | . | . | . | T | C | . | 1.36 | −0.39 | . | * | F | 2.28 | 1.29 |
| Pro | 157 | . | . | . | . | . | T | C | . | 0.39 | −0.57 | . | * | F | 2.70 | 0.88 |
| Asp | 158 | . | . | . | . | T | . | . | . | 0.46 | 0.07 | * | * | F | 1.73 | 0.66 |
| Leu | 159 | . | . | B | . | . | T | . | . | 0.10 | 0.26 | * | * | . | 0.91 | 0.48 |
| Ser | 160 | . | . | B | B | . | . | . | . | 0.56 | 0.51 | * | * | . | −0.06 | 0.49 |
| Val | 161 | . | . | B | B | . | . | . | . | 0.24 | 0.09 | . | * | . | −0.03 | 0.57 |
| Met | 162 | . | . | B | B | . | . | . | . | 0.57 | 0.51 | * | * | . | −0.26 | 0.69 |
| Tyr | 163 | . | . | B | . | . | T | . | . | −0.10 | −0.17 | * | * | . | 1.53 | 1.00 |
| Arg | 164 | . | . | B | . | . | T | . | . | 0.82 | 0.01 | . | * | . | 1.12 | 0.72 |
| Gly | 165 | . | . | . | . | T | T | . | . | 1.17 | −0.63 | . | * | F | 3.06 | 1.43 |
| Arg | 166 | . | . | . | . | T | T | . | . | 1.72 | −1.24 | . | * | F | 3.40 | 1.83 |
| Cys | 167 | . | . | . | . | T | . | . | . | 1.66 | −1.61 | * | * | F | 2.86 | 1.25 |
| Arg | 168 | . | . | . | . | T | T | . | . | 1.90 | −1.04 | * | * | F | 2.57 | 0.68 |
| Lys | 169 | . | . | . | . | T | T | . | . | 1.76 | −1.47 | * | * | F | 2.23 | 0.60 |
| Ser | 170 | . | . | . | . | T | T | . | . | 1.24 | −0.97 | * | * | F | 2.04 | 1.52 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Cys | 171 | . | . | . | . | T | T | . | 0.28 | −0.90 | * | * | . | 1.40 | 0.58 |
| Glu | 172 | . | . | B | B | . | . | . | 0.28 | −0.26 | * | . | . | 0.30 | 0.21 |
| His | 173 | . | . | B | B | . | . | . | −0.04 | 0.31 | . | . | . | −0.30 | 0.09 |
| Val | 174 | . | . | B | B | . | . | . | 0.02 | 0.36 | . | * | . | −0.02 | 0.25 |
| Val | 175 | . | . | B | B | . | . | . | 0.11 | −0.21 | . | * | . | 0.86 | 0.28 |
| Cys | 176 | . | . | B | . | . | T | . | 0.78 | 0.21 | . | * | . | 0.94 | 0.32 |
| Pro | 177 | . | . | . | . | T | T | . | 0.48 | 0.11 | . | * | F | 1.77 | 0.74 |
| Arg | 178 | . | . | . | . | T | T | . | −0.16 | −0.14 | . | * | F | 2.80 | 1.34 |
| Pro | 179 | . | . | . | . | T | T | . | −0.16 | −0.21 | . | * | F | 2.52 | 1.34 |
| Gln | 180 | . | . | . | B | T | . | . | −0.16 | −0.14 | * | * | F | 1.69 | 0.64 |
| Ser | 181 | . | . | B | B | . | . | . | 0.51 | 0.07 | * | * | F | 0.41 | 0.24 |
| Cys | 182 | . | . | B | B | . | . | . | 0.72 | 0.07 | * | * | . | −0.02 | 0.26 |
| Val | 183 | . | . | B | B | . | . | . | 0.30 | 0.04 | * | * | . | −0.30 | 0.26 |
| Val | 184 | . | . | B | B | . | . | . | 0.17 | 0.13 | . | . | . | −0.02 | 0.28 |
| Asp | 185 | . | . | B | B | . | . | . | −0.13 | 0.17 | . | . | F | 0.41 | 0.52 |
| Gln | 186 | . | . | B | . | . | T | . | −0.42 | −0.01 | . | . | F | 1.69 | 0.94 |
| Thr | 187 | . | . | . | . | T | T | . | 0.21 | −0.16 | . | . | F | 2.52 | 1.28 |
| Gly | 188 | . | . | . | . | T | T | . | 0.40 | −0.30 | . | . | F | 2.80 | 1.04 |
| Ser | 189 | . | . | . | . | T | T | . | 0.40 | 0.27 | . | . | F | 1.77 | 0.32 |
| Ala | 190 | . | . | B | B | T | . | . | −0.46 | 0.51 | . | . | . | 0.64 | 0.17 |
| His | 191 | . | . | B | B | . | . | . | −1.12 | 0.67 | * | . | . | −0.04 | 0.12 |
| Cys | 192 | . | . | B | B | . | . | . | −0.70 | 0.81 | * | * | . | −0.32 | 0.05 |
| Val | 193 | . | . | B | B | . | . | . | −0.94 | 0.43 | * | . | . | −0.60 | 0.10 |
| Val | 194 | . | . | B | B | . | . | . | −1.23 | 0.43 | * | . | . | −0.60 | 0.07 |
| Cys | 195 | . | . | B | B | . | . | . | −0.86 | 0.43 | * | . | . | −0.60 | 0.14 |
| Arg | 196 | . | . | B | B | . | . | . | −1.49 | 0.29 | * | . | . | −0.30 | 0.28 |
| Ala | 197 | . | . | B | B | . | . | . | −1.03 | 0.21 | * | . | . | −0.30 | 0.20 |
| Ala | 198 | . | . | B | . | . | T | . | −1.03 | −0.00 | * | . | . | 0.70 | 0.59 |
| Pro | 199 | . | . | B | . | . | T | . | −0.39 | 0.07 | * | . | . | 0.10 | 0.22 |
| Cys | 200 | . | . | B | . | . | T | . | −0.02 | 0.50 | * | . | . | −0.20 | 0.34 |
| Pro | 201 | . | . | B | . | . | T | . | −0.43 | 0.39 | * | . | . | 0.10 | 0.45 |
| Val | 202 | . | . | B | . | . | . | . | −0.06 | 0.27 | . | . | F | 0.05 | 0.39 |
| Pro | 203 | . | . | . | . | T | . | . | 0.19 | 0.27 | . | . | F | 0.88 | 1.13 |
| Ser | 204 | . | . | . | . | T | . | . | 0.40 | 0.13 | . | . | F | 1.01 | 0.72 |
| Ser | 205 | . | . | . | . | . | T | C | 1.07 | 0.10 | * | . | F | 1.44 | 1.69 |
| Pro | 206 | . | . | . | . | T | T | . | 0.47 | −0.54 | * | . | F | 2.82 | 1.89 |
| Gly | 207 | . | . | . | . | T | T | . | 0.66 | −0.29 | . | . | F | 2.80 | 1.16 |
| Gln | 208 | . | . | B | . | . | T | . | 0.52 | −0.10 | . | . | F | 1.97 | 0.47 |
| Glu | 209 | . | . | B | . | . | . | . | 0.82 | −0.06 | . | . | F | 1.49 | 0.30 |
| Leu | 210 | . | . | B | . | . | . | . | 1.12 | −0.09 | . | . | F | 1.37 | 0.48 |
| Cys | 211 | . | . | B | . | . | T | . | 1.33 | −0.11 | . | . | F | 1.45 | 0.45 |
| Gly | 212 | . | . | . | . | T | T | . | 0.82 | −0.11 | . | . | F | 1.73 | 0.42 |
| Asn | 213 | . | . | . | . | T | T | . | 0.51 | 0.53 | . | * | F | 0.99 | 0.38 |
| Asn | 214 | . | . | . | . | T | T | . | 0.27 | 0.33 | . | * | F | 1.60 | 1.01 |
| Asn | 215 | . | . | . | B | T | . | . | 0.19 | 0.51 | . | . | F | 0.74 | 1.60 |
| Val | 216 | . | . | B | B | . | . | . | 0.56 | 0.77 | * | . | . | −0.12 | 0.70 |
| Thr | 217 | . | . | B | B | . | . | . | 0.60 | 0.76 | * | . | . | −0.28 | 0.58 |
| Tyr | 218 | . | . | B | B | . | . | . | −0.07 | 0.74 | . | . | . | −0.44 | 0.48 |
| Ile | 219 | . | . | B | B | . | . | . | −0.10 | 0.91 | . | . | . | −0.60 | 0.35 |
| Ser | 220 | . | . | B | . | . | T | . | −0.70 | 0.77 | * | * | . | −0.20 | 0.33 |
| Ser | 221 | . | . | B | . | . | T | . | 0.27 | 0.90 | * | . | . | −0.20 | 0.21 |
| Cys | 222 | . | . | B | . | . | T | . | 0.58 | 0.14 | * | . | . | 0.10 | 0.58 |
| His | 223 | . | . | B | . | . | T | . | 0.23 | −0.14 | * | . | . | 0.70 | 0.75 |
| Met | 224 | . | . | . | . | T | . | . | 0.81 | −0.03 | * | . | . | 0.90 | 0.57 |
| Arg | 225 | . | . | B | B | . | . | . | 0.44 | 0.07 | * | * | . | −0.15 | 1.53 |
| Gln | 226 | . | . | B | B | . | . | . | 0.04 | 0.07 | * | . | . | −0.30 | 0.60 |
| Ala | 227 | . | . | B | B | . | . | . | −0.10 | 0.36 | * | . | . | −0.30 | 0.53 |
| Thr | 228 | . | . | B | B | . | . | . | −0.41 | 0.43 | * | * | . | −0.60 | 0.22 |
| Cys | 229 | . | . | B | B | . | . | . | 0.30 | 0.86 | * | * | . | −0.60 | 0.13 |
| Phe | 230 | . | . | B | B | . | . | . | −0.11 | 0.46 | * | . | . | −0.60 | 0.25 |
| Leu | 231 | . | . | B | B | . | . | . | −1.00 | 0.34 | * | . | . | −0.30 | 0.23 |
| Gly | 232 | . | . | . | . | T | T | . | −0.76 | 0.54 | * | . | . | 0.20 | 0.30 |
| Arg | 233 | . | . | . | . | T | T | . | −1.30 | 0.40 | . | * | F | 0.65 | 0.34 |
| Ser | 234 | . | . | . | . | T | T | . | −0.52 | 0.26 | . | . | F | 0.65 | 0.31 |
| Ile | 235 | . | . | B | . | . | T | . | 0.14 | −0.43 | . | . | . | 0.70 | 0.61 |
| Gly | 236 | . | . | B | B | . | . | . | 0.37 | −0.36 | . | . | . | 0.30 | 0.42 |
| Val | 237 | . | . | B | B | . | . | . | 0.37 | 0.14 | . | . | . | −0.30 | 0.32 |
| Arg | 238 | . | . | B | B | . | . | . | −0.04 | 0.19 | . | * | . | −0.30 | 0.45 |
| His | 239 | . | . | B | . | . | T | . | −0.41 | −0.11 | * | * | . | 0.70 | 0.61 |
| Ala | 240 | . | . | . | . | T | T | . | −0.11 | 0.03 | * | * | . | 0.50 | 0.44 |
| Gly | 241 | . | . | . | . | T | T | . | −0.11 | −0.11 | * | . | . | 1.10 | 0.23 |
| Ser | 242 | . | . | . | . | T | T | . | 0.43 | 0.31 | * | * | . | 0.80 | 0.16 |
| Cys | 243 | . | . | . | . | T | T | . | 0.11 | 0.30 | * | . | . | 1.10 | 0.24 |
| Ala | 244 | . | . | . | . | T | T | . | 0.14 | 0.23 | . | . | . | 1.40 | 0.37 |
| Gly | 245 | . | . | . | . | . | T | C | 0.73 | −0.20 | . | . | F | 2.25 | 0.47 |
| Thr | 246 | . | . | . | . | . | T | C | 0.87 | −0.59 | . | . | F | 3.00 | 1.53 |
| Pro | 247 | . | . | . | . | . | . | C | 0.96 | −0.73 | . | . | F | 2.50 | 2.35 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 248 | . | . | . | . | . | . | C | 1.28 | −0.80 | . | . | F | 2.50 | 3.67 |
| Glu | 249 | . | . | . | . | . | . | C | 1.52 | −0.80 | . | . | F | 2.50 | 2.52 |
| Pro | 250 | . | . | . | . | . | T | C | 1.87 | −0.86 | . | . | F | 2.70 | 1.61 |
| Pro | 251 | . | . | . | . | . | T | C | 1.88 | −1.29 | . | . | F | 2.70 | 1.61 |
| Gly | 252 | . | . | . | . | . | T | C | 1.50 | −0.90 | . | . | F | 3.00 | 1.25 |
| Gly | 253 | . | . | . | . | . | T | C | 1.50 | −0.40 | . | . | F | 2.25 | 0.81 |
| Glu | 254 | . | A | . | . | . | . | C | 1.50 | −0.83 | . | . | F | 1.85 | 0.91 |
| Ser | 255 | . | A | . | . | . | . | C | 1.71 | −1.26 | . | . | F | 1.70 | 1.60 |
| Ala | 256 | A | A | . | . | . | . | . | 1.92 | −1.69 | * | . | F | 1.20 | 2.79 |
| Glu | 257 | A | A | . | . | . | . | . | 2.27 | −2.11 | * | . | F | 0.90 | 2.79 |
| Glu | 258 | A | A | . | . | . | . | . | 1.91 | −1.71 | * | . | F | 0.90 | 3.35 |
| Glu | 259 | A | A | . | . | . | . | . | 1.06 | −1.31 | * | . | F | 0.90 | 2.87 |
| Glu | 260 | A | A | . | . | . | . | . | 0.97 | −1.17 | * | . | F | 0.90 | 1.23 |
| Asn | 261 | A | A | . | . | . | . | . | 1.17 | −0.74 | * | . | . | 0.60 | 0.91 |
| Phe | 262 | A | A | . | . | . | . | . | 0.78 | −0.31 | . | . | . | 0.30 | 0.67 |
| Val | 263 | A | A | . | . | . | . | . | 0.39 | 0.11 | . | . | . | −0.30 | 0.49 |

Among highly preferred fragments in this regard are those that comprise regions of follistatin-3 that combine several structural features, such as several of the features set out above.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC® Deposit No. 209199. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A, 1B, and 1C (SEQ ID NO:1)). Of course, a polynucleotide which hybridizes only to a poly A sequence (such as the 3' terminal poly(A) tract of the follistatin-3 cDNA shown in FIGS. 1A, 1B, and 1C (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

In preferred embodiments, polynucleotides which hybridize to the reference polynucleotides disclosed herein encode polypeptides which either retain substantially the same biological function or activity as the mature form of the follistatin-3 polypeptide encoded by the polynucleotide sequence depicted in FIGS. 1A, 1B, and 1C (SEQ ID NO:1) or the clone contained in the deposit (HDTAH85).

Alternative embodiments are directed to polynucleotides which hybridize to the reference polynucleotide (i.e., a polynucleotide sequence disclosed herein), but do not retain biological activity. While these polynucleotides do not retain biological activity, they have uses, such as, for example, as probes for the polynucleotides of SEQ ID NO:1, for recovery of the polynucleotides, as diagnostic probes, and as PCR primers.

As indicated, nucleic acid molecules of the present invention which encode a follistatin-3 polypeptide may include, but are not limited to those encoding the amino acid sequence of the mature polypeptide, by itself; and the coding sequence for the mature polypeptide and additional sequences, such as those encoding the about 26 amino acid leader or secretory sequence, such as a pre-, or pro- or prepro-protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described by Gentz and colleagues (*Proc. Natl. Acad. Sci. USA* 86:821–824 (1989)), for instance, hexa-histidine provides for convenient purification of the fusion protein. The "HA" tag is another peptide useful for purification which corresponds to an epitope derived from the influenza hemagglutinin protein, which has been described by Wilson and coworkers (*Cell* 37:767 (1984)). As discussed below, other such fusion proteins include the follistatin-3 fused to Fc at the N- or C-terminus.

The present invention further relates to variants of the nucleic acid molecules of the present invention, which encode portions, analogs or derivatives of the follistatin-3 protein. Variants may occur naturally, such as a natural allelic variant. By an "allelic variant" is intended one of several alternate forms of a gene occupying a given locus on a chromosome of an organism (*Genes II*, Lewin, B., ed., John Wiley & Sons, New York (1985)). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the follistatin-3 protein or portions thereof Also especially preferred in this regard are conservative substitutions.

Most highly preferred are nucleic acid molecules encoding the mature protein having the amino acid sequence shown in SEQ ID NO:2 or the mature follistatin-3 amino acid sequence encoded by the deposited cDNA clone.

Further embodiments include an isolated nucleic acid molecule comprising a polynucleotide having a nucleotide sequence at least 90% identical, and more preferably at least 95%, 96%, 97%, 98% or 99% identical to a polynucleotide selected from the group consisting of: (a) a nucleotide sequence encoding the follistatin-3 polypeptide having the complete amino acid sequence in SEQ ID NO:2 (i.e., positions −26 to 237 of SEQ ID NO:2); (b) a nucleotide sequence encoding the follistatin-3 polypeptide having the complete amino acid sequence in SEQ ID NO:2 excepting the N-terminal methionine (i.e., positions −25 to 237 of SEQ ID NO:2); (c) a nucleotide sequence encoding the predicted mature follistatin-3 polypeptide having the amino acid sequence at positions 1 to 237 in SEQ ID NO:2; (d) a nucleotide sequence encoding the follistatin-3 polypeptide having the complete amino acid sequence encoded by the cDNA clone contained in ATCC® Deposit No. 209199; (e) a nucleotide sequence encoding the follistatin-3 polypeptide having the complete amino acid sequence excepting the N-terminal methionine encoded by the cDNA clone contained in ATCC® Deposit No. 209199; (f) a nucleotide sequence encoding the mature follistatin-3 polypeptide having the amino acid sequence encoded by the cDNA clone contained in ATCC® Deposit No. 209199; and (g) a nucleotide sequence complementary to any of the nucleotide sequences in (a), (b), (c), (d), (e) or (f) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d), (e), (f) or (g), above, or a polynucleotide which hybridizes under stringent hybridization conditions to a polynucleotide in (a), (b), (c), (d), (e), (f) or (g), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a follistatin-3 polypeptide having an amino acid sequence in (a), (b), (c), (d), (e) or (f), above. A further nucleic acid embodiment of the invention relates to an isolated nucleic acid molecule comprising a polynucleotide which encodes the amino acid sequence of a follistatin-3 polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a polynucleotide which encodes the amino acid sequence of a follistatin-3 polypeptide to have an amino acid sequence which contains not more than 7–10, 5–10, 3–7, 3–5, 2–5, 1–5, 1–3, 10, 9, 8, 7, 6, 5, 4, 3, 2 or 1 conservative amino acid substitutions.

The present invention also relates to recombinant vectors, which include the isolated nucleic acid molecules of the present invention, and to host cells containing the recombinant vectors, as well as to methods of making such vectors and host cells and for using them for production of follistatin-3 polypeptides or peptides by recombinant techniques.

By a polynucleotide having a nucleotide sequence at least, for example, 95% "identical" to a reference nucleotide sequence encoding a follistatin-3 polypeptide is intended that the nucleotide sequence of the polynucleotide is identical to the reference sequence except that the polynucleotide sequence may include up to five point mutations per each 100 nucleotides of the reference nucleotide sequences encoding the follistatin-3 polypeptides. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A, 1B, and 1C, or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman to find the best segment of homology between two sequences (*Advances in Applied Mathematics* 2:482–489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. A preferred method for determing the best overall match between a query sequence (a sequence of the present invention) and a subject sequence, also referred to as a global sequence alignment, can be determined using the FASTDB computer program based on the algorithm of Brutlag and colleagues (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is becuase the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignement of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The present application is directed to nucleic acid molecules at least 90%, 95%, 96%, 97%, 98% or 99% identical to the nucleic acid sequence shown in FIGS. 1A, 1B, and 1C (SEQ ID NO:1) or to the nucleic acid sequence of the deposited cDNA, irrespective of whether they encode a polypeptide having follistatin-3 activity. This is because even where a particular nucleic acid molecule does not encode a polypeptide having follistatin-3 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having follistatin-3 activity include, inter alia, (1) isolating the follistatin-3 gene or allelic variants thereof in a cDNA library; (2) in situ hybridization (e.g., "FISH") to metaphase chromosomal spreads to provide precise chromosomal location of the follistatin-3 gene, as described by Verma and colleagues (*Human Chromosomes. A Manual of Basic Techniques*, Pergamon Press, New York (1988)); and Northern Blot analysis for detecting follistatin-3 mRNA expression in specific tissues.

Preferred, however, are nucleic acid molecules having sequences at least 90%, 95%, 96%, 97%, 98% or 99% identical to the nucleic acid sequence shown in FIGS. 1A, 1B, and 1C (SEQ ID NO:1) or to the nucleic acid sequence of the deposited cDNA which do, in fact, encode a polypeptide having follistatin-3 protein activity. By "a polypeptide having follistatin-3 activity" is intended polypeptides exhibiting activity similar, but not necessarily identical, to an activity of the mature follistatin-3 protein of the invention, as measured in a particular biological assay. For example, the follistatin-3 protein of the present invention inhibits the binding of activin to the activin receptor. An activin receptor-binding inhibition assay is described by Hashimoto and colleagues (*J. Biol. Chem.* 272:13835–13842 (1997)). Briefly, the assay involves culturing rat pituitary cells ($5\times10^5$ cells) in 24-well plates in the presence of [$^{125}$I]-activin A (40 ng/mL; activin A is labeled using the chloramine-T method as described by Hasegawa and coworkers (*Endocrinol. Japan* 33:645–654 (1986)) and follistatin-3 or a mutein thereof (200 ng/mL). A baseline of activin-binding is determined by affinity cross-linking [$^{125}$I]-activin A to the pituitary cells using the bifunctional chemical cross-linker disuccinimidyl suberate (DSS) in the absence of follistatin-3. Cross-linking is achieved by washing cells once with binding buffer (DMEM containing 25 mM HEPES (pH 7.4) and 0.2% bovine serum albumen) and incubating on ice for 2 h with 40 ng/mL [$^{125}$I]-activin A in the binding buffer. Following incubation, cells are washed 3 times with ice-cold PBS and incubated in PBS containing I mM DSS for 20 min on ice. The reaction is then quenched with PBS. The cells are removed from the culture dish by scraping, rinsed with a Tris solution (20 mM Tris-HCl (pH 7.2) containing 2 mM EDTA, 5 mM benzamidine, 2 mM phenylmethylsulfonyl fluoride (PMSF), 2 mM N-ethylaleimide, and 2 mM diisopropyl fluorophosphate), centrifuged, and resuspended in solubilization buffer (50 mM Tris-HCl (pH 7.2) containing 150 mM NaCl, 2 mM EDTA, 5 mM benzamidine, 2 mM PMSF, 2 mM N-ethylaleimide, 2 mM diisopropyl fluorophosphate, 1% Triton X-100, and 10% glycerol), and stirred gently on ice for 1 h. The cell lysates are introduced into 2% SDS and boiled at 100° C. for 10 min. The resulting affinity-labeled lysates are then subject to SDS-PAGE (7.5 or 8% gels). Following SDS-PAGE, gels are fixed, stained with 0.25% Coomassie Brilliant Blue R-250, destained, air-dried, and then visualized by autoradiography. Inhibition of activin binding of the activin receptor is analyzed in samples with which follistatin-3 or a mutein thereof (200 ng/mL) are incubated with labeled activin in the binding buffer incubation described above. The degree to which the formation of affinity cross-linked activin/activin receptor complexes is decreased correlates with the ability of follistatin-3 or a mutein thereof to bind to labeled activin protein. As such, the relative binding affinity of activin for its receptor versus follistatin-3 or a mutein thereof can be quantitated. Such activity is useful for regulating the effective amount of activin present in a given system.

Follistatin-3 protein binds to activin in a dose-dependent manner in the above-described assay. Thus, "a polypeptide having follistatin-3 protein activity" includes polypeptides that also exhibit any of the same binding activities in the above-described assays in a dose-dependent manner. Although the degree of dose-dependent activity need not be identical to that of the follistatin-3 protein, preferably, "a polypeptide having follistatin-3 protein activity" will exhibit substantially similar dose-dependence in a given activity as compared to the follistatin-3 protein (i.e., the candidate polypeptide will exhibit greater activity or not more than about 25-fold less and, preferably, not more than about tenfold less activity relative to the reference follistatin-3 protein).

Like follistatin-1, follistatin-3 inhibits the secretion of FSH. An assay for measuring the suppression of spontaneous FSH release from primary cultured rat pituitary cells is well known in the art (Hasegawa, Y., et al., *Endocrinol. Jpn.* 33:645–654 (1986)). Briefly, freshly isolated pituitary cells are suspended in DMEM containing gentamicin (35 µg/mL), fungizone (1 µg/mL), 0.05% glutamine, 0.1% sodium bicarbonate, 10% horse serum, and 2.5% fetal bovine serum at a density of $3\times10^5$ cells/mL, and plated in 96-well culture plates ($6\times10^4$ cells/0.2 mL/well). Various amounts (0.1–100 ng/mL) of follistatin-3 are then added to the culture medium. After culturing for 3 days at 37° C. (5% $CO_2$), cultured media are assayed for quantity of secreted FSH by a double antibody RIA method using an RIA kit and plotted as FSH Secreted (ng/mL/72 h) versus Protein Added (ng/mL).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A, 1B, and 1C (SEQ ID NO:1) will encode a polypeptide "having follistatin-3 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having follistatin-3 protein activity. This is because the skilled artisan is fully aware of amino acid substitutions that are either less likely or not likely to significantly effect protein function (e.g., replacing one aliphatic amino acid with a second aliphatic amino acid), as further described below.

The present invention also relates to vectors which include the isolated DNA molecules of the present invention, host cells which are genetically engineered with the recombinant vectors, and the production of follistatin-3 polypeptides or fragments thereof by recombinant techniques. The vector may be, for example, a phase, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Vectors preferred for use in bacteria include pQE70, pQE60 and pQE-9 (QIAGEN, Inc., supra); pBS vectors, Phagescript vectors, Bluescript vectors, pNH8A, pNH16a, pNH18A, pNH46A (Stratagene); and ptrc99a, pKK223-3, pKK233-3, pDR540, pRIT5 (Pharmacia). Among preferred eukaryotic vectors are pWLNEO, pSV2CAT, pOG44, pXT1, and pSG (Stratagene); and pSVK3, pBPV, pMSG and pSVL (Pharmacia). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., *Basic Methods In Molecular Biology* (1986)).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5 (Bennett, D., et al., *J. Molecular Recognition* 8:52–58 (1995); Johanson, K., et al., *J . Biol. Chem.* 270:9459–9471 (1995)).

The follistatin-3 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

POLYPEPTIDES AND FRAGMENTS

The invention further provides an isolated follistatin-3 polypeptide having the amino acid sequence encoded by the deposited cDNA, or the amino acid sequence in SEQ ID NO:2, or a peptide or polypeptide comprising a portion of the above polypeptides.

To improve or alter the characteristics of follistatin-3 polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced.activity or increased stability. In addition, they may be purified in higher yields and show better solubility than the corresponding natural polypeptide, at least under certain purification and storage conditions.

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.*, 268:2984–2988 (1993)) reported modified KGF proteins that had heparin binding activity even if 3, 8, or 27 N-terminal amino acid residues were missing. In the present case, since the protein of the invention is a member of the inhibin-related polypeptide family, deletions of N-terminal amino acids up to the cysteine at position 12 of SEQ ID NO:2 may retain some biological activity such as binding activin or an activin-like molecule. Polypeptides having further N-terminal deletions including the cysteine-12 residue in SEQ ID NO:2 would not be expected to retain such biological activities because it is known that this residue is likely required for forming a disulfide bridge to provide structural stability which is needed for protein-protein interaction and is in the beginning of the conserved domain required for biological activities.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the follistatin-3 shown in SEQ ID NO:2, up to the cysteine residue at position number 12, and polynucleotides encoding such polypeptides. In particular, the present invention provides polypeptides comprising the amino acid sequence of residues $n^1$-237 of SEQ ID NO:2, where $n^1$ is an integer in the range of –26–12, and 12 is the position of the first residue from the N-terminus of the complete follistatin-3 polypeptide (shown in SEQ ID NO:2) believed to be required for activin-binding or activin-like protein-binding activity of the follistatin-3 protein.

More in particular, the invention provides polynucleotides encoding polypeptides having the amino acid sequence of residues of –26–237, –25–237, –24–237, –23–237, –22–237, –21–237, –20–237, –19–237, –18–237, –17–237, –16–237, –15–237, –14–237, –13–237, –12–237, –10–237, –9–237, –8–237, –7–237, –6–237, –5–237, –4–237, –3–237, –2–237, –1–237, 1–237, 2–237, 3–237, 4–237, 5–237, 6–237, 7–237, 8–237, 9–237, 10–237, 11–237, and 12–237 of SEQ ID NO:2. Polypeptides encoded by these polynucleotides also are provided. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the follistatin-3 polypeptides described above, and the polypeptides encoded thereby.

The present invention also encompasses the above polynucleotide sequences fused to a heterologous polynucleotide sequence, and the polypeptides encoded thereby.

Similarly, many examples of biologically functional C-terminal deletion muteins are known. For instance, Interferon gamma shows up to ten times higher activities by deleting 8–10 amino acid residues from the carboxy terminus of the protein (Dobeli, et al., *J. Biotechnology* 7:199–216 (1988)). In the present case, since the protein of the invention is a member of the activin-related polypeptide family, deletions of C-terminal amino acids up to the cysteine at position 217 of SEQ ID NO:2 may retain some biological activity such as binding activin or an activin-like molecule. Polypeptides having further C-terminal deletions including the cysteine residue at position 217 of SEQ ID NO:2 would not be expected to retain such biological activities because it is known that this residue is likely required for forming a disulfide bridge to provide structural stability which is needed for protein-protein interactions and is the beginning of the conserved domain required for biological activities.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature form of the protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the follistatin-3 shown in SEQ ID NO:2, up to the cysteine residue at position 217 of SEQ ID NO:2, and polynucleotides encoding such polypeptides. In particular, the present invention provides polypeptides having the amino acid sequence of residues $-26-m^1$ of the amino acid sequence in SEQ ID NO:2, where $m^1$ is any integer in the range of 217 to 237, and residue 217 is the position of the first residue from the C-terminus of the complete follistatin-3 polypeptide (shown in SEQ ID NO:2) believed to be required for the activin-binding or activin-like protein-binding of the follistatin-3 protein.

More in particular, the invention provides polynucleotides encoding polypeptides having the amino acid sequence of residues –26–217, –26–218, –26–219, –26–220, –26–221, –26–222, –26–223, –26–224, –26–225, –26–226, –26–227, –26–228, –26–229, –26–230, –26–231, –26–232, –26–233, –26–234, –26–235, –26–236, and –26–237 of SEQ NO:2. Polypeptides encoded by these polynucleotides also are provided. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the follistatin-3 polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini, which may be described generally as having residues $n^1-m^1$ of SEQ ID NO:2, where $n^1$ and $m^1$ are integers as described above.

Also included are a nucleotide sequence encoding a polypeptide consisting of a portion of the complete follistatin-3 amino acid sequence encoded by the cDNA clone contained in ATCC® Deposit No. 209199, where this portion excludes from 1 to about 37 amino acids from the amino terminus of the complete amino acid sequence encoded by the cDNA clone contained in ATCC® Deposit No. 209199, or from 1 to about 20 amino acids from the carboxy terminus, or any combination of the above amino terminal and carboxy terminal deletions, of the complete amino acid sequence encoded by the cDNA clone contained in ATCC® Deposit No. 209199. Polynucleotides encoding all of the above deletion mutant polypeptide forms also are provided.

As mentioned above, even if deletion of one or more amino acids from the N-terminus of a protein results in modification of loss of one or more biological functions of the protein, other biological activities may still be retained. Thus, the ability of the shortened follistatin-3 mutein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that a follistatin-3 mutein with a large number of deleted N-terminal amino acid residues may retain some biological or immungenic activities. In fact, peptides composed of as few as six follistatin-3 amino acid residues may often evoke an immune response.

Accordingly, the present invention further provides polypeptides having one or more residues deleted from the amino terminus of the follistatin-3 amino acid sequence shown in SEQ ID NO:2, up to the glutamic acid residue at position number 258 and polynucleotides encoding such polypeptides. In particular, the present invention provides polypeptides comprising the amino acid sequence of residues $n^2-263$ of FIG. 1A (SEQ ID NO:2), where $n^2$ is an integer in the range of 2 to 258, and 259 is the position of the first residue from the N-terminus of the complete follistatin-3 polypeptide believed to be required for at least immunogenic activity of the follistatin-3 protein.

More in particular, the invention provides polynucleotides encoding polypeptides comprising, or alternatively consisting of, the amino acid sequence of residues of R-2 to V-263; P-3 to V-263; G-4 to V-263; A-5 to V-263; P-6 to V-263; G-7 to V-263; V-263; L-9 to V-263; W-10 to V-263; P-11 to V-263; L-12 to V-263; P-13 to V-263; W-14 to V-263; G-15 to V-263; A-16 to V-263; L-17 to V-263; A-18 to V-263; W-19 to V-263, A-20 to V-263; V-21 to V-263; G-22 to V-263; F-23 to V-263; V-24 to V-263; S-25 to V-263; S-26 to V-263; M-27 to V-263; G-28 to V-263; S-29 to V-263; G-30 to V-263; N-31 to V-263; P-32 to V-263; A-33 to V-263; P-34 to V-263; G-35 to V-263; G-36 to V-263; V-37 to V-263; C-38 to V-263; W-39 to V-263; L-40 to V-263; Q-41 to V-263; Q-42 to V-263; G-43 to V-263; Q-44 to V-263; E-45 to V-263; A-46 to V-263; T-47 to V-263; C-48 to V-263; S-49 to V-263; L-50 to V-263; V-51 to V-263; L-52 to V-263; Q-53 to V-263; T-54 to V-263; D-55 to V-263; V-56 to V-263; T-57 to V-263; R-58 to V-263; A-59 to V-263; E-60 to V-263; C-61 to V-263; C-62 to V-263; A-63 to V-263; S-64 to V-263; G-65 to V-263; N-66 to V-263; I-67 to V-263; D-68 to V-263; T-69 to V-263; A-70 to V-263; W-71 to V-263; S-72 to V-263; N-73 to V-263; L-74 to V-263; T-75 to V-263; H-76 to V-263; P-77 to V-263; G-78 to V-263; N-79 to V-263; K-80 to V-263; I-81 to V-263; N-82 to V-263; L-83 to V-263; L-84 to V-263; G-85 to V-263; F-86 to V-263; L-87 to V-263; G-88 to V-263, L-89 to V-263; V-90 to V-263; H-91 to V-263; C-92 to V-263; L-93 to V-263; P-94 to V-263; C-95 to V-263; K-96 to V-263; D-97 to V-263; S-98 to V-263; C-99 to V-263, D-100 to V-263; G-101 to V-263; V-102 to V-263; E-103 to V-263; C-104 to V-263; G-105 to V-263; P-106 to V-263; G-107 to V-263; K-108 to V-263; A-109 to V-263; C-110 to V-263; R-111 to V-263; M-112 to V-263; L-113 to V-263; G-114 to V-263; G-115 to V-263; R-116 to V-263; P-117 to V-263; R-118 to V-263; C-119 to V-263; E-120 to V-263; C-121 to V-263; A-122 to V-263; P-123 to V-263; D-124 to V-263; C-125 to V-263; S-126 to V-263, G-127 to V-263; L-128 to V-263; P-129 to V-263; A-130 to V-263; R-131 to V-263, L-132 to Y-263, Q-133 to V-263, V-134 to V-263, C-135 to V-263; G-136 to V-263; S-137 to V-263; D-138 to V-263; G-139 to V-263; A-140 to V-263; T-141 to V-263; Y-142 to V-263; R-143 to V-263; D-144 to V-263; E-145 to V-263; C-146 to V-263; E-147 to V-263; L-148 to V-263; R-149 to V-263; A-150 to V-263; A-151 to V-263; R-152 to V-263; C-153 to V-263; R-154 to V-263; G-155 to V-263; H-156 to V-263; P-157 to V-263; D-158 to V-263; L-159 to V-263; S-160 to V-263; V-161 to V-263; M-162 to V-263; Y-163 to V-263; R-164 to V-263; G-165 to V-263; R-166 to V-263; C-167 to V-263; R-168 to V-263; K-169 to V-263, S-170 to V-263; C-171 to V-263; E-172 to V-263; H-173 to V-263; V-174 to V-263; V-175 to V-263; C-176 to V-263; P-177 to V-263; R-178 to V-263; P-179 to V-263; Q-180 to V-263; S-181 to V-263; C-182 to V-263; V-183 to V-263; V-184 to V-263; D-l85 to V-263; Q-186 to V-263; T-187 to V-263; G-188 to V-263; S-189 to V-263; A-190 to V-263; H-191 to V-263; C-192 to V-263; V-193 to V-263; V-194 to V-263; C-195 to V-263; R-196 to V-263; A-197 to V-263; A-198 to V-263; P-199 to V-263; C-200 to V-263; P-201 to V-263; V-202 to V-263; P-203 to V-263; S-204 to V-263; S-205 to V-263; P-206 to V-263; G-207 to V-263; Q-208 to V-263; E-209 to V-263; L-210 to V-263; C-211 to V-263; G-212 to V-263; N-213 to V-263; N-214 to V-263; N-215 to V-263; V-216 to V-263; T-217 to V-263; Y-218 to V-263; I-219 to V-263; S-220 to V-263; S-221 to V-263; C-222 to V-263; H-223 to V-263; M-224 to V-263; R-225 to V-263; Q-226 to V-263; A-227 to V-263; T-228 to V-263; C-229 to V-263; F-230 to V-263; L-231 to V-263; G-232 to V-263; R-233 to V-263; S-234 to V-263; I-235 to V-263; G-236 to V-263; V-237 to V-263; R-238 to V-263; H-239 to V-263; A-240 to V-263; G-241 to V-263; S-242 to V-263; C-243 to V-263; A-244 to V-263; G-245 to V-263; T-246 to V-263; P-247 to V-263; E-248 to V-263; E-249 to V-263; P-250 to V-263; P-251 to V-263; G-252 to V-263; G-253 to V-263, E-254 to V-263; S-255 to V-263; A-256 to V-263; E-257 to V-263; and E-258 to V-263 of the follistatin-3 amino acid sequence shown in FIG. 1A (which is identical to the sequence shown as SEQ ID NO:2, with the exception that the amino acid residues in FIG. 1A are numbered consecutively from 1 through 263 from the N-terminus to the C-terminus, while the amino acid residues in SEQ ID NO:2 are numbered consecutively from –26 through 237 to reflect the position of the predicted signal peptide). Polypeptides encoded by these polynucleotides also are provided. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the follistatin-3 polypeptides described above, and the polypeptides encoded thereby. The present invention also encompasses the above polynucleotide sequences fused to a heterologous polynucleotide sequence, and the polypeptides encoded thereby.

Also as mentioned above, even if deletion of one or more amino acids from the C-terminus of a protein results in modification of loss of one or more biological functions of the protein, other biological activities may still be retained. Thus, the ability of the shortened follistatin-3 mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a follistatin-3 mutein with a large number of deleted C-terminal amino acid residues may retain some biological or immungenic activities. In fact, peptides composed of as few as six follistatin-3 amino acid residues may often evoke an immune response.

Accordingly, the present invention further provides polypeptides having one or more residues deleted from the carboxy terminus of the amino acid sequence of the follistatin-3 shown in SEQ ID NO:2, up to the proline residue at position number 6, and polynucleotides encoding such polypeptides. In particular, the present invention provides polypeptides comprising the amino acid sequence of residues $1-m^2$ of SEQ ID NO:2, where $m^2$ is an integer in the range of 6 to 262, and 6 is the position of the first residue from the C-terminus of the complete follistatin-3 polypeptide believed to be required for at least immunogenic activity of the follistatin-3 protein.

More in particular, the invention provides polynucleotides encoding polypeptides comprising, or alternatively consisting of, the amino acid sequence of residues M-1 to F-262; M-1 to N-261; M-1 to E-260; M-1 to E-259; M-1 to E-258; M-1 to E-257; M-1 to A-256, M-1 to S-255; M-1 to E-254, M-1 to G-253; M-1 to G-252; M-1 to P-251; M-1 to P-250; M-1 to E-249; M-1 to E-248; M-1 to P-247; M-1 to T-246; M-1 to G-245; M-1 to A-244; M-1 to C-243; M-1 to S-242; M-1 to G-241; M-1 to A-240, M-1 to H-239; M-1 to R-238; M-1 to V-237; M-1 to G-236; M-1 to I-235; M-1 to S-234; M-1 to R-233; M-1 to G-232; M-1 to L-231; M-1 to F-230; M-1 to C-229; M-1 to T-228; M-1 to A-227; M-1 to Q-226; M-1 to R-225; M-1 to M-224; M-1 to H-223; M-1 to C-222; M-1 to S-221; M-1 to S-220; M-1 to 1–219; M-1 to Y-218; M-1 to T-217; M-1 to V-216; M-1 to N-215; M-1 to N-214; M-1 to N-213; M-1 to G-212; M-1 to C-211; M-1 to L-210; M-1 to E-209; M-1 to Q-208; M-1 to G-207; M-1 to P-206; M-1 to S-205; M-1 to S-204; M-1 to P-203; M-1 to V-202; M-1 to P-201; M-1 to C-200; M-1 to P-199; M-1 to A-198; M-1 to A-197; M-1 to R-196; M-1 to C-195; M-1 to V-194; M-1 to V-193; M-1 to C-192; M-1 to H-191, M-1 to A-190; M-1 to S-189; M-1 to G-188; M-1 to T-187; M-1 to Q-186; M-1 to D-185; M-1 to V-184; M-1 to V-183; M-1 to C-182; M-1 to S-181; M-1 to Q-180; M-1 to P-179; M-1 to R-178; M-1 to P-177; M-1 to C-176; M-1 to V-175; M-1 to V-174; M-1 to H-173; M-1 to E-172; M-1 to C-171; M-1 to S-170; M-1 to K-169; M-1 to R-168; M-1 to C-167; M-1 to R-166; M-1 to G-165; M-1 to R-164; M-1 to Y-163; M-1 to M-162; M-1 to V-161; M-1 to S-160; M-1 to L-159; M-1 to D-158; M-1 to P-157; M-1 to H-156; M-1 to G-155; M-1 to R-154; M-1 to C-153; M-1 to R-152; M-1 to A-151; M-1 to A-150; M-1 to R-149; M-1 to L-148; M-1 to E-147; M-1 to C-146; M-1 to E-145; M-1 to D-144; M-1 to R-143; M-1 to Y-142; M-1 to T-141; M-1 to A-140; M-1 to G-139; M-1 to D-138; M-1 to S-137; M-1 to G-136; M-1 to C-135; M-1 to V-134; M-1 to Q-133; M-1 to L-132; M-1 to R-131; M-1 to A-130; M-1 to P-129; M-1 to L-128, M-1 to G-127; M-1 to S-126; M-1 to C-125; M-1 to D-124; M-1 to P-123; M-1 to A-122; M-1 to C-121; M-1 to E-120; M-1 to C-119; M-1 to R-118; M-1 to P-117; M-1 to R-116; M-1 to G-115; M-1 to G-114; M-1 to L-113; M-1 to M-112; M-1 to R-111; M-1 to C-110; M-1 to A-109; M-1 to K-108; M-1 to G-107; M-1 to P-106; M-1 to G-105; M-1 to C-104; M-1 to E-103; M-1 to V-102; M-1 to G-101; M-1 to D-100; M-1 to C-99; M-1 to S-98; M-1 to D-97; M-1 to K-96; M-1 to C-95; M-1 to P-94; M-1 to L-93, M-1 to C-92; M-1 to H-91; M-1 to V-90; M-1 to L-89; M-1 to G-88; M-1 to L-87; M-1 to F-86; M-1 to G-85; M-1 to L-84; M-1 to L-83; M-1 to N-82; M-1 to I-81; M-1 to K-80; M-1 to N-79; M-1 to G-78; M-1 to P-77; M-1 to H-76; M-1 to T-75; M-1 to L-74; M-1 to N-73; M-1 to S-72; M-1 to W-71; M-1 to A-70; M-1 to T-69; M-1 to D-68; M-1 to I-67; M-1 to N-66; M-1 to G-65; M-1 to S-64; M-1 to A-63; M-1 to C-62; M-1 to C-61; M-1 to E-60; M-1 to A-59; M-1 to R-58; M-1 to T-57, M-1 to V-56; M-1 to D-55; M-1 to T-54; M-1 to Q-53; M-1 to L-52; M-1 to V-51; M-1 to L-50; M-1 to S-49; M-1 to C-48; M-1 to T-47; M-1 to A-46; M-1 to E-45, M-1 to Q-44; M-1 to G-43; M-1 to Q-42; M-1 to Q-41; M-1 to L-40; M-1 to W-39; M-1 to C-38; M-1 to V-37; M-1 to G-36; M-1 to G-35; M-1 to P-34; M-1 to A-33; M-1 to P-32; M-1 to N-31; M-1 to G-30; M-1 to S-29; M-1 to G-28; M-1 to M-27; M-1 to S-26; M-1 to S-25; M-1 to V-24; M-1 to F-23; M-1 to G-22; M-1 to V-21; M-1 to A-20; M-1 to W-19; M-1 to A-18; M-1 to L-17; M-1 to A-16; M-1 to G-15; M-1 to W-14; M-1 to P-13; M-1 to L-12; M-1 to P-11; M-1 to W-10; M-1 to L-9; M-1 to P-8; M-1 to G-7; M-1 to P-6 of the sequence of the follistatin-3 sequence shown in FIG. 1A (which is identical to the sequence shown as SEQ ID NO:2, with the exception that the amino acid residues in FIG. 1A are numbered consecutively from 1 through 263 from the N-terminus to the C-terminus, while the amino acid residues in SEQ ID NO:2 are numbered consecutively from −26 through 237 to reflect the position of the predicted signal peptide). Polypeptides encoded by these polynucleotides also are provided. The present invention is also directed to nucleic acid molecules comprising, or alternatively, consisting of, a polynucleotide sequence at least 80%, 85%, 90%, 92%, 94%, 95%, 96%, 97%, 98% or 99% identical to the polynucleotide sequences encoding the follistatin-3 polypeptides described above, and the polypeptides encoded thereby. The present invention also encompasses the above polynucleotide sequences fused to a heterologous polynucleotide sequence, and the polypeptides encoded thereby.

The invention also provides polypeptides having one or more amino acids deleted from both the amino and the carboxyl termini of a follistatin-3 polypeptide, which may be described generally as having residues $n^2-m^2$ of FIG. 1A (SEQ ID NO:2), where $n^2$ and $m^2$ are integers as described above.

In addition to terminal deletion forms of the protein discussed above, it also will be recognized by one of ordinary skill in the art that some amino acid sequences of the follistatin-3 polypeptide can be varied without significant effect of the structure or function of the protein. If such differences in sequence are contemplated, it should be remembered that there will be critical areas on the protein which determine activity.

Thus, the invention further includes variations of the follistatin-3 polypeptide which show substantial follistatin-3 polypeptide activity or which include regions of follistatin-3 protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided wherein the authors indicate that there are two main approaches for studying the tolerance of an amino acid sequence to change (Bowie, J. U., et al., *Science* 247:1306–1310 (1990)). The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described by Bowie and coworkers (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the follistatin-3 of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table II).

TABLE II

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Embodiments of the invention are directed to polypeptides which comprise the amino acid sequence of a follistatin-3 polypeptide descrubed hereub, but having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still even more preferably, not more than 20 conservative amino acid substitutions, when compared with the follistatin-3 polynucleotide sequence described herein. Of course, in order of ever-increasing preference, it is highly preferable for a peptide or polypeptide to have an amino acid sequence which comprises the amino acid sequence of a follistatin-3 polypeptide, which contains at least one, but not more than 10, 9, 8, 7, 6, 5, 4, 3, 2 or 1 conservative amino acid substitutions.

In further specific embodiments, the number of substitutions, additions or deletions in the amino acid sequence of FIGS. 1A, 1B, and 1C (SEQ ID NO:2), a polypeptide sequence encoded by the deposited clones, and/or any of the polypeptide fragments described herein is 75, 70, 60, 50, 40, 35, 30, 25, 20, 15, 10, 9, 8, 7, 6, 5, 4, 3, 2, 1 or 150–50, 100–50, 50–20, 30–20, 20–15, 20–10, 15–10, 10–1, 5–10, 1–5, 1–3 or 1–2.

To improve or alter the characteristics of follistatin-3 polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Thus, the invention also encompasses follistatin-3 derivatives and analogs that have one or more amino acid residues deleted, added, or substituted to generate follistatin-3 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to acheive, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the follistatin-3 polypeptides of the invention, and/or an amino acid deletion at the second position of any one or more such recognition sequences will prevent glycosylation of the follistatin-3 polypeptide at the modified tripeptide sequence (see, e.g., Miyajima, A., et al., *EMBO. J.* 5(6):1193–1197 (1986)).

Amino acids in the follistatin-3 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard, et al., *Clin. Exp. Immunol.* 2:331–340 (1967); Robbins, et al., *Diabetes* 36:838–845 (1987); Cleland, et al., *Crit. Rev. Therapeutic Drug Carrier Systems* 10:307–377 (1993)).

A mutational analysis of the two N-linked glycosylation sites (Asn-95 and Asn-259) of follistatin-1 was conducted by Inouye and colleagues (*Biochem. Biophys. Res. Comm.* 179:352–358 (1991)). As described in the analysis, disruption of either or both of the N-linked glycosylation sites (by mutation of Thr-97 and Thr-261 to alanine) had no discernable effect on activin-binding and FSH secretion. However, results of the same study suggest that insertion of two amino acid residues (lysine and leucine) between residues Asn-2 and Cys-3 of follistatin-1 completely abolishes its inhibitory activity on FSH secretion from the pituitary, as well as its ability to bind activin. The asparagine and surrounding residues described in this analysis are weakly conserved between follistatin-1 and follistatin-3. There are however, two potential N-linked glycosylation sites in the sequence of follistatin-3 (N-73 and N-215; see FIG. 1A). In addition, 4 out of 5 amino acids making up the sequence near the amino terminus, at which point Inouye and coworkers made their two amino acid insertion (supra), are conserved. Consequently, the extreme amino terminal region of the predicted mature follistatin-3 polypeptide may have a high potential for exhibiting a deleterious effect through mutation.

The polypeptides of the present invention are preferably provided in an isolated form, and preferably are substantially purified. A recombinantly produced version of the follistatin-3 polypeptide can be substantially purified by the one-step method described by Smith and Johnson (*Gene* 67:31–40 (1988)). Polypeptides of the invention also can be purified from natural or recombinant sources using anti-Follistatin-3 antibodies of the invention in methods which are well known in the art of protein purification.

The invention further provides an isolated follistatin-3 polypeptide comprising an amino acid sequence selected from the group consisting of: (a) the amino acid sequence of the full-length follistatin-3 polypeptide having the complete amino acid sequence shown in SEQ ID NO:2 (i.e., positions −26 to 237 of SEQ ID NO:2); (b) the amino acid sequence of the full-length follistatin-3 polypeptide having the complete amino acid sequence shown in SEQ ID NO:2 excepting the N-terminal methionine (i.e., positions −25 to 237 of SEQ ID NO:2); (c) the amino acid sequence of the predicted mature follistatin-3 polypeptide having the amino acid sequence at positions 1 to 237 in SEQ ID NO:2; (d) the amino acid sequence of the full-length follistatin-3 polypeptide having the complete amino acid sequence encoded by the cDNA clone contained in ATCC® Deposit No. 209199; (e) the amino acid sequence of the full-length follistatin-3 polypeptide having the complete amino acid sequence excepting the N-terminal methionine encoded by the cDNA clone contained in ATCC® Deposit No. 209199; and (f) the amino acid sequence of the mature follistatin-3 polypeptide having the amino acid sequence encoded by the cDNA clone contained in ATCC® Deposit No. 209199. The polypeptides of the present invention also include polypeptides having an amino acid sequence at least 80% identical, more preferably at least 90% identical, and still more preferably 95%, 96%, 97%, 98% or 99% identical to those described in (a), (b), (c), (d), (e) or (f) above, as well as polypeptides having an a mino acid sequence with at least 90% similarity, and more preferably at least 95% similarity, to those above.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a follistatin-3 polypeptide is intended that the amino acid sequence of the polypeptide is identical to the reference sequence except that the polypeptide sequence may include up to five amino acid alterations per each 100 amino acids of the reference amino acid of the follistatin-3 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1A (SEQ ID NO:2), the amino acid sequence encoded by deposited cDNA clone HDTAH85, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty= 0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The invention also encompasses fusion proteins in which the full-length follistatin-3 polypeptide or fragment, variant, derivative, or analog thereof is fused to an unrelated protein. These fusion proteins can be routinely designed on the basis of the follistatin-3 nucleotide and polypeptide sequences disclosed herein. For example, as one of skill in the art will appreciate, follistatin-3 polypeptides and fragments (including epitope-bearing fragments) thereof described herein can be combined with parts of the constant domain of immunoglobulins (IgG), resulting in chimeric (fusion) polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et al., *Nature* 331:84–86 (1988)). Fusion proteins that have a disulfide-linked dimeric structure due to the IgG part can also be more efficient in binding and neutralizing other molecules than the monomeric follistatin-3 polypeptide or polypeptide fragments alone (Fountoulakis, et al., *J. Biochem.* 270:3958–3964 (1995)). Examples of follistatin-3 fusion proteins that are encompassed by the invention include, but are not limited to, fusion of the follistatin-3 polypeptide sequences to any amino acid sequence that allows the fusion proteins to be displayed on the cell surface (e.g. the IgG Fc domain); or fusions to an enzyme, fluorescent protein, or luminescent protein which provides a marker function.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting follistatin-3 protein expression as described below or as agonists and antagonists capable of enhancing or inhibiting follistatin-3 protein function. Further, such polypeptides can be used in the yeast two-hybrid system to "capture" follistatin-3 protein binding proteins which are also candidate agonists and antagonists according to the present invention. The yeast two hybrid system is described by Fields and Song (*Nature* 340:245–246 (1989)).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope". The number of immunogenic epitopes of a protein generally is less than the number of antigenic epitopes (see, for instance, Geysen, et al., *Proc. Natl. Acad. Sci. USA* 81:3998–4002 (1983)).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (see, for instance, Sutcliffe, J. G., et al., *Science* 219:660–666 (1983)). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention (see, for instance, Wilson, et al., *Cell* 37:767–778 (1984)).

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate follistatin-3-specific antibodies include: a polypeptide comprising amino acid residues from about Leu-14 to about Ala-20, from about Ser-46 to about Ile-55, from about Gly-88 to about Pro-97, from about Gly-113 to about Leu-133, from about Arg-138 to about Glu-146, from about Pro-177 to about Thr-191, from about Gly-219 to about Val-237. These polypeptide fragments have been determined to bear antigenic epitopes of the follistatin-3 protein by the analysis of the Jameson-Wolf antigenic index, as shown in FIG. 3 and Table I, above.

The epitope-bearing peptides and polypeptides of the invention may be produced by any conventional means (see, for example, Houghten, R. A., et al., *Proc. Natl. Acad. Sci. USA* 82:5131–5135 (1985); and U.S. Pat. No. 4,631,211 to Houghten, et al. (1986)).

Epitope-bearing peptides and polypeptides of the invention are used to induce antibodies according to methods well known in the art (see, for instance, Sutcliffe, et al., supra; Wilson, et al., supra; Chow, M., et al., *Proc. Natl. Acad. Sci. USA* 82:910–914; and Bittle, F. J., et al., *J. Gen. Virol.* 66:2347–2354 (1985)). Immunogenic epitope-bearing peptides of the invention, i.e., those parts of a protein that elicit an antibody response when the whole protein is the immunogen, are identified according to methods known in the art (see, for instance, Geysen, et al., supra). Further still, U.S. Pat. No. 5,194,392, issued to Geysen, describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, issued to Geysen, describes a method of detecting or determining a sequence of monomers which is a topographical equivalent of a ligand which is complementary to the ligand binding site of a particular receptor of interest. Similarly, U.S. Pat. No. 5,480,971, issued to Houghten and colleagues, on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, follistatin-3 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et al., *Nature* 331:84–86 (1988)). Fusion proteins that have a disulfide-linked dimeric structure due to the IgG part can also be more efficient in binding and neutralizing other molecules than the monomeric follistatin-3 protein or protein fragment alone (Fountoulakis, et al., *J. Biochem.* 270:3958–3 964 (1995)).

Follistatin-3 protein-specific antibodies for use in the present invention can be raised against the intact follistatin-3 protein or an antigenic polypeptide fragment thereof, which may be presented together with a carrier protein, such as an albumin, to an animal system (such as rabbit or mouse) or, if it is long enough (at least about 25 amino acids), without a carrier.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody,"

as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., *J. Immunol.* 147:60–69 (1991); U.S. Pat. Nos. 4,474,893; 4,714,681; 4,925,648; 5,573,920; 5,601,819; Kostelny et al., *J. Immunol.* 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO. 96/40281; U.S. Pat. No. 5,811,097, Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7): 3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies s may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438, WO 89/12624; U.S. Pat. No. 5,314,995, and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 20). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC®. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., Bio Techniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5): 489–498 (1991); Studnicka et al., Protein Engineering 7(6) :805–814 (1994), Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633, 425; 5,569,825; 5,661,016; 5,545,806; 5,814,318; 5,885, 793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science242:1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., $E.$ $coli$, $B.$ $subtilis$) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5 K promoter). Preferably, bacterial cells such as $Escherichia$ $coli$, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the $E.$ $coli$ expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in $Spodoptera$ $frugiperda$ cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12;488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification.

One reported example describes chimeric.proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriaziny-lamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5): 155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody, alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989), Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994), Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment, this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J.Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk,. silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^3$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level, and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Reproductive System- and Cell Growth and Differentiation-Related Disorders Diagnosis The present inventors have discovered that follistatin-3 is expressed not only in Hodgkin's Lymphoma, but also in synovial fibroblasts, gall bladder, resting and serum-induced smooth muscle, testes, Merkel cells, HEL cells, hippocampus, TNF-alpha- and IFN-induced epithelial cells, keratinocyte, amygdala depression, HL-60 cells, hepatoma, progesterone-treated epidermal cells, endothelial cells, HSC172 cells, epithelioid sarcoma, activated T-cells, breast lymph node, pancreatic carcinoma, fetal dura mater, fetal lung, epididymis, placenta, dendritic cells, rejected kidney, and uterine cancer. For a number of reproductive system-related disorders and disorders related to the regulation of cell growth and differentiation, substantially altered (increased or decreased) levels of follistatin-3 gene expression can be detected in reproductive system tissue or other cells or bodily fluids (e.g., sera, plasma, urine, synovial fluid or spinal fluid) taken from an individual having such a disorder, relative to a "standard" follistatin-3 gene expression level, that is, the follistatin-3 expression level in reproductive system tissues or bodily fluids from an individual not having the reproductive system or cell growth and differentiation disorder. Thus, the invention provides a diagnostic method useful during diagnosis of a reproductive system or cell growth and differentiation disorder, which involves measuring the expression level of the gene encoding the follistatin-3 protein in reproductive system tissue or other cells or body fluid from an individual and comparing the measured gene expression level with a standard follistatin-3 gene expression level, whereby an increase or decrease in the gene expression level compared to the standard is indicative of a reproductive or cell growth and differentiation system disorder.

In particular, it is believed that certain tissues in mammals with cancer of various cells and tissues of the reproductive or other systems express significantly reduced levels of the follistatin-3 protein and mRNA encoding the follistatin-3 protein when compared to a corresponding "standard" level. Further, it is believed that enhanced levels of the follistatin-3 protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of reproductive system or cell growth and differentiation disorders, including cancers of these systems, which involves measuring the expression level of the gene encoding the follistatin-3 protein in reproductive system tissue or other cells or body fluid from an individual and comparing the measured gene expression level with a standard follistatin-3 gene expression level, whereby an increase or decrease in the gene expression level compared to the standard is indicative of a reproductive system disorder or a disorder of the regulation of cell growth and differentiation.

Where a diagnosis of a disorder in the reproductive or other system including diagnosis of a tumor, has already been made according to conventional methods, the present invention is useful as a prognostic indicator, whereby patients exhibiting depressed follistatin-3 gene expression will experience a worse clinical outcome relative to patients expressing the gene at a level nearer the standard level.

By "assaying the expression level of the gene encoding the follistatin-3 protein" is intended qualitatively or quantitatively measuring or estimating the level of the follistatin-3 protein or the level of the mRNA encoding the follistatin-3 protein in a first biological sample either directly (e.g., by determining or estimating absolute protein level or mRNA level) or relatively (e.g., by comparing to the follistatin-3 protein level or mRNA level in a second biological sample). Preferably, the follistatin-3 protein level or mRNA level in the first biological sample is measured or estimated and compared to a standard follistatin-3 protein level or mRNA level, the standard being taken from a second biological sample obtained from an individual not having the disorder or being determined by averaging levels from a population of individuals not having a disorder of the reproductive system or of regulation of cell growth and differentiation. As will be appreciated in the art, once a standard follistatin-3 protein level or mRNA level is known, it can be used repeatedly as a standard for comparison.

By "biological sample" is intended any biological sample obtained from an individual, body fluid, cell line, tissue culture, or other source which contains follistatin-3 protein or mRNA. As indicated, biological samples include body fluids (such as sera, plasma, urine, synovial fluid and spinal fluid) which contain free follistatin-3 protein, reproductive system tissue, and other tissue sources found to express complete or mature follistatin-3 or a follistatin-3 receptor. Methods for obtaining tissue biopsies and body fluids from mammals are well known in the art. Where the biological sample is to include mRNA, a tissue biopsy is the preferred source.

The present invention is useful for diagnosis or treatment of various reproductive system-related disorders and disorders of the regulation of cell growth and differentiation in mammals, preferably humans. Such disorders include tumors, cancers, interstitial lung disease, and any disregulation of the growth and differentiation patterns of cell function including, but not limited to, autoimmunity, arthritis, leukemias, lymphomas, immunosuppression, immunity, humoral immunity, inflammatory bowel disease, myelosuppression and the like.

Total cellular RNA can be isolated from a biological sample using any suitable technique such as the single-step guanidinium-thiocyanate-phenol-chloroform method described by Chomczynski and Sacchi (*Anal Biochem.* 162:156–159 (1987)). Levels of mRNA encoding the follistatin-3 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying follistatin-3 protein levels in a biological sample can occur using antibody-based techniques. For example, follistatin-3 protein expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting follistatin-3 protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}I$, $^{121}I$), carbon ($^{14}C$), sulfur ($^{35}S$), tritium ($^{3}H$), indium ($^{112}In$), and technetium ($^{99m}Tc$), and fluorescent labels, such as fluorescein and rhodamine, and biotin.

In addition to assaying follistatin-3 protein levels in a biological sample obtained from an individual, follistatin-3 protein can also be detected in vivo by imaging. Antibody labels or markers for in vivo imaging of follistatin-3 protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A follistatin-3 protein-specific antibody or antibody fragment which has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled antibody or antibody fragment will then preferentially accumulate at the location of cells which contain follistatin-3 protein. In vivo tumor imaging is described by Burchiel and coworkers (Chapter 13 in *Tumor Imaging: The Radiochemical Detection of Cancer*, Burchiel, S. W. and Rhodes, B. A., eds., Masson Publishing Inc. (1982)).

Treatment

As noted above, follistatin-3 polynucleotides and polypeptides are useful for diagnosis of conditions involving abnormally high or low expression of follistatin-3 activities. Given the cells and tissues where follistatin-3 is expressed as well as the activities modulated by follistatin-3, it is readily apparent that a substantially altered (increased or decreased) level of expression of follistatin-3 in an individual compared to the standard or "normal" level produces pathological conditions related to the bodily system(s) in which follistatin-3 is expressed and/or is active.

It will also be appreciated by one of ordinary skill that, since the follistatin-3 protein of the invention is a member of the inhibin-related protein family the mature secreted form of the protein may be released in soluble form from the cells which express the follistatin-3 by proteolytic cleavage. Therefore, when follistatin-3 mature form is added from an exogenous source to cells, tissues or the body of an individual, the protein will exert its physiological activities on its target cells of that individual.

Therefore, it will be appreciated that conditions caused by a decrease in the standard or normal level of Follistatin-3 activity in an individual, particularly disorders of the reproductive system, can be treated by administration of follistatin-3 polypeptide (in the form of the mature protein). Thus, the invention also provides a method of treatment of an individual in need of an increased level of follistatin-3 activity comprising administering to such an individual a pharmaceutical composition comprising an amount of an isolated follistatin-3 polypeptide of the invention, particularly a mature form of the follistatin-3 protein of the invention, effective to increase the follistatin-3 activity level in such an individual.

Follistatin-3 may be used to treat male sterility by its innate ability to bind activin and, as a result, prevent activin-binding to its receptor. Activin receptor-binding results in a suppression of FSH secretion. Increased levels of FSH, in turn, result in an increase in spermatogenesis (Ying, S.-Y. *Etidocrine Rev.* 9:267–293 (1988)). Thus, a decrease in the effective concentration of activin will result in an FSH-mediated increase in spermatogenesis. In addition, since activin elicits a number of biological effects including the modulation of gonadal androgen biosynthesis (Hsueh, A. J. W., et al., *Proc. Natl. Acad. Sci. USA* 84:5082–5086 (1987)), the attenuation of growth hormone secretion (Bilezikjian, L. M., et al., *Endocrinology* 126:2369–2376 (1990), the promotion of erythroid cell differentiation (Eto, Y., et al., *Biochem. Biophys. Res. Comm.* 142:1095–1103 (1987)), the induction of mesoderm formation (Smith, J. C., et al., *Nature* 345:729–731 (1990)), and the maintenance of nerve cell survival (Schubert, D., et al., *Nature* 344:868–870 (1990)), and since follistatin-3 directly inhibits activin acitivity, follistatin-3 may be used to therapeutically regulate, as well as diagnostically evaluate, the conditions and events listed above. Follistatin-3 may also be used to inhibit the activin-induced differentiation of follicular granulosa cells (Nakamura, T., et al., *Biochim. Biophys. Acta* 1135:103–109 (1992)). Follistatin-3 may be used therapeutically to regulate autocrine endothelial cell activity and, as a result, induce angiogenesis (Kozian, D. H., et al., *Lab. Invest.* 76:267–276 (1997)). Follistatin-3 may also be used to inhibit the activity of activin and thereby prevent the observed activin-mediated inhibition of basal and androgen-stimulated proliferation and induction of apoptosis (Wang, Q. F., et al., *Endocrinology* 137:5476–5483 (1996)). Treatment to increase the expression or the presence of follistatin-3 protein may be used to inhibit the progression of gonadotroph adenomas, osteosarcomas, hepatomas, and other tumors and cancers including bone, breast, colon, lymphomas, leukemias, epithelial carcinomas, pancreatic, stomach, liver, lung, melanoma, prostate, ovarian, uterine, bladder, gliomas, retinoblastomas, sarcomas, and the like (Penabad, J. L., et al., *J. Clin. Endocrinol Metab.* 81:3397–3403 (1996); Kato, M. V., et al., *Oncogene* 12:1361–1364 (1996)). Follistatin-3 may also be employed to stimulate wound healing. In this same manner, follistatin-3 may also be employed to treat other fibrotic disorders, including liver cirrhosis, osteoarthritis and pulmonary fibrosis. Follistatin-3 also increases the presence of eosinophils which have the distinctive function of killing the larvae of parasites that invade tissues, as in schistosomiasis, trichinosis and ascariasis. It may also be employed to regulate hematopoiesis, by regulating the activation and differentiation of various hematopoietic progenitor cells, for example, to release mature leukocytes from the bone marrow following chemotherapy, i.e., in stem cell mobilization. Follistatin-3 may also be employed to treat sepsis. Follistatin-3 may also be used to treat a number of disease states known to those of skill in the art which may be therapeutically regulated by exploiting the prohibitive interation of follistatin-3 with the activin molecule.

In certain embodiments, follistatin-3 and/or agonists or antagonists of follistatin-3 may be used to treat cancers including, but not limited to those described herein. In one embodiment, the cancer is B cell chronic lymphocytic leukemia. In a further embodiment, the cancer is a non-Hodgkin lymphoma.

Formulations

The follistatin-3 polypeptide composition will be formulated and dosed in a fashion consistent with good medical practice, taking into account the clinical condition of the individual patient (especially the side effects of treatment with follistatin-3 polypeptide alone), the site of delivery of the follistatin-3 polypeptide composition, the method of administration, the scheduling of administration, and other factors known to practitioners. The "effective amount" of follistatin-3 polypeptide for purposes herein is thus determined by such considerations.

As a general proposition, the total pharmaceutically effective amount of follistatin-3 polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the follistatin-3 polypeptide is typically administered at a dose rate. of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the follistatin-3 of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The follistatin-3 polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U., et al., *Biopolymers* 22:547–556 (1983)), poly (2-hydroxyethyl methacrylate; Langer, R., et al., *J. Biomed. Mater. Res.* 15:167–277 (1981), and Langer, R., *Chem. Tech.* 12:98–105 (1982)), ethylene vinyl acetate (Langer, R., et al., Id.) or poly-D-(-)-3-hydroxybutyric acid (EP 133,988). Sustained-release follistatin-3 polypeptide compositions also include liposomally entrapped follistatin-3 polypeptide. Liposomes containing follistatin-3 polypeptide are prepared by methods known in the art (DE 3,218,121; Epstein, et al., *Proc. Natl. Acad. Sci.* (*USA*) 82:3688–3692 (1985); Hwang, et al., *Proc. Natl. Acad. Sci.* (*USA*) 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324). Ordinarily, the liposomes are of the small (about 200–800 Angstroms) unilamellar type in which the lipid content is greater than about 30 mol. percent cholesterol, the selected proportion being adjusted for the optimal follistatin-3 polypeptide therapy.

For parenteral administration, in one embodiment, the follistatin-3 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the follistatin-3 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The follistatin-3 polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of follistatin-3 polypeptide salts.

Follistatin-3 polypeptide to be used for therapeutic administration must be sterile. Sterility is readily accomplished by filtration through sterile filtration membranes (e.g., 0.2 micron membranes). Therapeutic follistatin-3 polypeptide compositions generally are placed into a container having a sterile access port, for example, an intravenous solution bag or vial having a stopper pierceable by a hypodermic injection needle.

Follistatin-3 polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous follistatin-3 polypeptide solution, and the resulting mixture is lyophilized. The infusion solution is prepared by reconstituting the lyophilized follistatin-3 polypeptide using bacteriostatic water-for-injection (WFI).

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of follistatin-3 on cells, such as its interaction with follistatin-3-binding molecules such as activin, an activin-like molecule, or a follistatin-3 receptor molecule. An agonist is a compound which increases the natural biological functions of follistatin-3 or which functions in a manner similar to follistatin-3, while antagonists decrease or eliminate such functions.

In another aspect of this embodiment the invention provides a method for identifying an activin-like molecule or a receptor protein or other ligand-binding protein which binds specifically to a follistatin-3 polypeptide. For example, a cellular compartment, such as a membrane or a preparation thereof, may be prepared from a cell that expresses a molecule that binds follistatin-3. The preparation is incubated with labeled follistatin-3 and complexes of follistatin-3 bound to the activin-like molecule, receptor or other binding protein are isolated and characterized according to routine methods known in the art. Alternatively, the follistatin-3 polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds follistatin-3, such as a molecule of a signaling or regulatory pathway modulated by follistatin-3. The preparation is incubated with labeled follistatin-3 in the absence or the presence of a candidate molecule which may be a follistatin-3 agonist or antagonist. The ability of the candidate molecule to bind the binding molecule is reflected in decreased binding of the labeled ligand. Molecules which bind gratuitously, i.e., without inducing the effects of follistatin-3 on binding the follistatin-3 binding molecule, are most likely to be good antagonists. Molecules that bind well and elicit effects that are the same as or closely related to follistatin-3 are agonists.

Follistatin-3-like effects of potential agonists and antagonists may by measured, for instance, by determining activity of a second messenger system following interaction of the candidate molecule with a cell or appropriate cell preparation, and comparing the effect with that of follistatin-3 or molecules that elicit the same effects as follistatin-3. Second messenger systems that may be useful in this regard include but are not limited to AMP guanylate cyclase, ion channel or phosphoinositide hydrolysis second messenger systems.

Another example of an assay for follistatin-3 antagonists is a competitive assay that combines follistatin-3 and a potential antagonist with membrane-bound follistatin-3 receptor molecules or recombinant follistatin-3 receptor molecules under appropriate conditions for a competitive inhibition assay. Follistatin-3 can be labeled, such as by radioactivity, such that the number of follistatin-3 molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing follistatin-3-induced activities, thereby preventing the action of follistatin-3 by excluding follistatin-3 from binding.

Other potential antagonists include antisense molecules. Antisense technology can be used to control gene expression through antisense DNA or RNA or through triple-helix formation. Antisense techniques are discussed in a number of studies (for example, Okano, *J. Neurochem.* 56:560 (1991); "Oligodeoxynucleotides as Antisense Inhibitors of Gene Expression." CRC Press, Boca Raton, Fla. (1988)). Triple helix formation is discussed in a number of studies, as well (for instance, Lee, et al., *Nucleic Acids Research* 6:3073 (1979); Cooney, et al., *Science* 241:456 (1988); Dervan, et al., *Science* 251:1360 (1991)). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of follistatin-3. The antisense RNA oligonucleotide hybridizes to the mRNA in vivo and blocks translation of the mRNA molecule into follistatin-3 polypeptide. The oligonucleotides described above can also be delivered to cells such that the antisense RNA or DNA may be expressed in vivo to inhibit production of follistatin-3 protein.

The agonists and antagonists may be employed in a composition with a pharmaceutically acceptable carrier, e.g., as described above.

Antagonists of follistatin-3 may be employed, for instance, to treat a deficiency in FSH, estrogen, and other hormones. Follistatin-1 and follistatin-3 are potent inhibitors of FSH and estrogen production and secretion. As a result, a deficiency of these or related hormones may be corrected or ameliorated through the use of a follistatin-3 antagonist. A follistatin-3 antagonist may be used to prevent or inhibit or reduce the production of spermatozoa by inhibiting the interaction of follistatin-3 with activin. Antagonists of follistatin-3 may also be used to modulate gonadal androgen biosynthesis, attenuate growth hormone secretion, promote the differentiation of follicular granulosa, erythroid, and other cell types, induce mesoderm formation, and increase the survival of nerve cells. A follistatin-3 antagonist may be used to inhibit angiogenesis related to or independent of tumorigenesis. Follistatin-3 antagonists may also be useful in increasing the activity of activin and thereby increasing the observed activin-mediated inhibition of basal and androgen-stimulated proliferation and induction of apoptosis. Antagonists of follistatin-3 may be used to regulate the hormonal and growth factor environment, and consequently, the activity of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by alterring the activation state of mononuclear phagocytes. They may also be employed to treat idiopathic hyper-eosinophilic syndrome by preventing eosinophil production and activation. Endotoxic shock may also be treated by the antagonists by preventing the activation of macrophages. Any of the above antagonists may be employed in a composition with a pharmaceutically acceptable carrier, e.g., as hereinafter described.

Gene Mapping

The nucleic acid molecules of the present invention are also valuable for chromosome identification. The sequence is specifically targeted to and can hybridize with a particular location on an individual human chromosome, Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a follistatin-3 protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp (for a review of this technique, see Verma, et al., *Human Chromosomes: A Manual Of Basic Techniques*, Pergamon Press, New York (1988)).

Once a sequence has been mapped to a precise chromosomal location, the physical position of the sequence on the chromosome can be correlated with genetic map data. Such data are found, for example, on the World Wide Web (McKusick, V. Mendelian Inheritance In Man, available on-line through Johns Hopkins University, Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Exemplary Uses of the Follistatin-3 Polynucleotides

The follistatin-3 polynucleotides identified herein can be used in numerous ways as reagents. The following description should be considered exemplary and utilizes known techniques.

There exists an ongoing need to identify new chromosome markers, since few chromosome marking reagents, based on actual sequence data (repeat polymorphisms), are presently available.

Briefly, sequences can be mapped to chromosomes by preparing PCR primers (preferably 15–25 bp) from the sequences shown in SEQ ID NO:1. Primers can be selected using computer analysis so that primers do not span more than one predicted exon in the genomic DNA. These primers are then used for PCR screening of somatic cell hybrids containing individual human chromosomes. Only those hybrids containing the human follistatin-3 gene corresponding to the SEQ ID NO:1 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the follistatin-3 polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the follistatin-3 polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the follistatin-3 polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50–500 potential causative genes.

Thus, once coinheritance is established, differences in the follistatin-3 polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the follistatin-3 polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using follistatin-3 polynucleotides. Any of these alterations (altered expression, chromosomal rearrangement, or mutation) can be used as a diagnostic or prognostic marker.

In addition to the foregoing, a follistatin-3 polynucleotide can be used to control gene expression through triple helix formation or antisense DNA or RNA. Both methods rely on binding of the polynucleotide to DNA or RNA. For these techniques, preferred polynucleotides are usually 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself(antisense—Okano, J. Neurochem. 56:560 (1991); Oligodeoxy-nucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat disease.

Follistatin-3 polynucleotides are also useful in gene therapy. One goal of gene therapy is to insert a normal gene into an organism having a defective gene, in an effort to correct the genetic defect. Follistatin-3 offers a means of targeting such genetic defects in a highly accurate manner. Another goal is to insert a new gene that was not present in the host genome, thereby producing a new trait in the host cell.

The follistatin-3 polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The follistatin-3 polynucleotides can be used as additional DNA markers for RFLP.

The follistatin-3 polynucleotides can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, follistatin-3 polynucleotides can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from follistatin-3 sequences. Panels of such reagents can identify tissue by species and/or by organ type. In a similar fashion, these reagents can be used to screen tissue cultures for contamination.

Because follistatin-3 is found expressed in Hodgkin's lymphoma, and a variety of additional cells and tissue types detailed infra, follistatin-3 polynucleotides are useful as hybridization probes for differential identification of the tissue(s) or cell type(s) present in a biological sample. Similarly, polypeptides and antibodies directed to follistatin-3 polypeptides are useful to provide immunological probes for differential identification of the tissue(s) or cell type(s). In addition, for a number of disorders of the above tissues or cells, particularly of the reproductive systems, significantly higher or lower levels of follistatin-3 gene expression may be detected in certain tissues (e.g., cancerous and wounded tissues) or bodily fluids (e.g., serum, plasma, urine, synovial fluid or spinal fluid) taken from an individual having such a disorder, relative to a "standard" follistatin-3 gene expression level, i.e., the follistatin-3 expression level in healthy tissue from an individual not having the reproductive system disorder.

Thus, the invention provides a diagnostic method of a disorder, which involves: (a) assaying follistatin-3 gene expression level in cells or body fluid of an individual; (b) comparing the follistatin-3 gene expression level with a standard follistatin-3 gene expression level, whereby an increase or decrease in the assayed follistatin-3 gene expression level compared to the standard expression level is indicative of disorder in the reproductive system.

In the very least, the follistatin-3 polynucleotides can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Exemplary Uses of Follistatin-3 Polypeptides

Follistatin-3 polypeptides can be used in numerous ways. The following description should be considered exemplary and utilizes known techniques.

Follistatin-3 polypeptides can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S.W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of follistatin-3 polypeptide in cells or body fluid of an individual; (b) comparing the level of gene expression with a standard gene expression level, whereby an increase or decrease in the assayed follistatin-3 polypeptide gene expression level compared to the standard expression level is indicative of a disorder.

Moreover, follistatin-3 polypeptides can be used to treat disease. For example, patients can be administered follistatin-3 polypeptides in an effort to replace absent or decreased levels of the follistatin-3 polypeptide (e.g., insulin), to supplement absent or decreased levels of a different polypeptide (e.g., hemoglobin S for hemoglobin B), to inhibit the activity of a polypeptide (e.g., an oncogene), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth).

Similarly, antibodies directed to follistatin-3 polypeptides can also be used to treat disease. For example, administration of an antibody directed to a follistatin-3 polypeptide can bind and reduce overproduction of the polypeptide. Similarly, administration of an antibody can activate the polypeptide, such as by binding to a polypeptide bound to a membrane (receptor).

At the very least, the follistatin-3 polypeptides can be used as molecular weight markers on SDS-PAGE gels or on molecular sieve gel filtration columns using methods well known to those of skill in the art. Follistatin-3 polypeptides can also be used to raise antibodies, which in turn are used to measure protein expression from a recombinant cell, as a way of assessing transformation of the host cell. Moreover, follistatin-3 polypeptides can be used to test the following biological activities.

Gene Therapy Methods

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of the follistatin-3 polypeptide of the present invention. This method requires a polynucleotide which codes for a follistatin-3 polypeptide operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a follistatin-3 polynucleotide ex vivo, with the engineered cells then being provided to a patient to be treated with the polypeptide. Such methods are well-known in the art. For example, see Belldegrun, A., et al., J. Natl. Cancer Inst. 85: 207–216 (1993); Ferrantini, M. et al., Cancer Research 53: 1107–1112 (1993); Ferrantini, M. et al., J. Immunology 153: 4604–4615 (1994), Kaido, T., et al., Int. J. Cancer 60: 221–229 (1995); Ogura, H., et al., Cancer Research 50: 5102–5106 (1990); Santodonato, L., et al., Human Gene Therapy 7:1–10 (1996); Santodonato, L., et al., Gene Therapy 4:1246–1255 (1997); and Zhang, J.-F. et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the follistatin-3 polynucleotide constructs can be delivered by any method that delivers injectable materials to the cells of an animal, such as, injection into the interstitial space of tissues (heart, muscle, skin, lung, liver, and the like). The follistatin-3 polynucleotide constructs may be delivered in a pharmaceutically acceptable liquid or aqueous carrier.

In one embodiment, the follistatin-3 polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the follistatin-3 polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The follistatin-3 polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of follistatin-3 DNA. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter, retroviral LTRs; the b-actin promoter; and human growth hormone promoters. The promoter also may be the native promoter for follistatin-3.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The follistatin-3 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked follistatin-3 DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

As is evidenced in the Examples, naked follistatin-3 nucleic acid sequences can be administered in vivo results in the successful expression of follistatin-3 polypeptide in the femoral arteries of rabbits.

The constructs may also be delivered with delivery vehicles such as viral sequences, viral particles, liposome formulations, lipofectin, precipitating agents, etc. Such methods of delivery are known in the art.

In certain embodiments, the follistatin-3 polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA (1987) 84:7413–7416, which is herein incorporated by reference); mRNA (Malone et al., Proc. Natl. Acad. Sci. USA (1989) 86:6077–6081, which is herein incorporated by reference); and purified transcription factors (Debs et al., J. Biol. Chem. (1990) 265:10189–10192, which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIFBCO BRL, Grand Island, N.Y. (See, also, Feigner et al., Proc. Natl. Acad. Sci. USA (1987) 84:7413–7416, which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Feigner et al., Proc. Natl. Acad. Sci. USA 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology (1983), 101:512–527, which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable. complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta (1975) 394:483; Wilson et al., Cell (1979) 17:77); ether injection (Deamer, D. and Bangham, A., Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); detergent dialysis (Enoch, H. and Strittmatter, P., Proc. Natl. Acad. Sci. USA (1979) 76:145); and reverse-phase evaporation (REV) (Fraley et al., J. Biol. Chem. (1980) 255:10431; Szoka, F. and Papahadjopoulos, D., Proc. Natl. Acad. Sci. USA (1978) 75:145; Schaefer-Ridder et al., Science (1982) 215:166), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are be engineered, ex vivo or in vivo, using a retroviral particle containing RNA which comprises a sequence encoding follistatin-3. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19–14X, VT-19–17-H2, RCRE, RCRIP, GP+E-86, GP+envAm 12, and DAN cell lines as described in Miller, Human Gene Therapy 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding follistatin-3. Such retroviral vector particles then may be employed, to transduce eukaryotic cells, either in vitro or in vivo. The transduced eukaryotic cells will express follistatin-3.

In certain other embodiments, cells are engineered, ex vivo or in vivo, with follistatin-3 polynucleotide contained in an adenovirus vector. Adenovirus can be manipulated such that it encodes and expresses follistatin-3, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. (1974) Am. Rev. Respir. Dis. 109:233–238). Finally, adenovirus.mediated gene transfer has been demonstrated in a number of instances including transfer of alpha-1-antitrypsin and CFTR to the lungs of cotton rats (Rosenfeld, M. A. et al. (1991) Science 252:431–434; Rosenfeld et al., (1992) Cell 68:143–155). Furthermore, extensive studies to attempt to establish adenovirus as a causative agent in human cancer were uniformly negative (Green, M. et al. (1979) Proc. Natl. Acad. Sci. USA 76:6606).

Suitable adenoviral vectors useful in the present invention are described, for example, in Kozarsky and Wilson, Curr.

Opin. Genet. Devel. 3:499–503 (1993); Rosenfeld et al., Cell 68:143–155 (1992); Engelhardt et al., Human Genet. Ther. 4:759–769 (1993); Yang et al., Nature Genet. 7:362–369 (1994); Wilson et al., Nature 365:691–692 (1993); and U.S. Pat. No. 5,652,224, which are herein incorporated by reference. For example, the adenovirus vector Ad2 is useful and can be grown in human 293 cells. These cells contain the E 1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, for example, the HARP promoter of the present invention, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The follistatin-3 polynucleotide construct is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the follistatin-3 polynucleotide construct. These viral particles are then used to transduce eukaryotic cells, either ex vivo or in vivo. The transduced cells will contain the follistatin-3 polynucleotide construct integrated into its genome, and will express follistatin-3.

Another method of gene therapy involves operably associating heterologous control regions and endogenous polynucleotide sequences (e.g. encoding follistatin-3) via homologous recombination (see, e.g., U.S. Pat. No. 5,641,670, issued Jun. 24, 1997, International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the follistatin-3 desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous follistatin-3 sequence is placed under the control of the promoter. The promoter then drives the expression of the endogenous follistatin-3 sequence.

The polynucleotides encoding follistatin-3 may be administered along with other polynucleotides encoding other angiongenic proteins. Angiogenic proteins include, but are not limited to, acidic and basic fibroblast growth factors, VEGF-1, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding follistatin-3 contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers (Kaneda et al., Science 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities of Follistatin-3

Follistatin-3 polynucleotides or polypeptides, or agonists or antagonists of follistatin-3, can be used in assays to test for one or more biological activities. If follistatin-3 polynucleotides or polypeptides, or agonists or antagonists of follistatin-3, do exhibit activity in a particular assay, it is likely that follistatin-3 may be involved in the diseases associated with the biological activity. Therefore, follistatin-3 could be used to treat the associated disease.

Immune Activity

Follistatin-3 polynucleotides or polypeptides, or agonists or antagonists of follistatin-3 may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, follistatin-3 polynucleotides or polypeptides, or agonists or antagonists of follistatin-3, can be used as a marker or detector of a particular immune system disease or disorder.

Follistatin-3 polynucleotides or polypeptides, or agonists or antagonists of follistatin-3, may be useful in treating or detecting deficiencies or disorders of hematopoietic cells. Follistatin-3 polynucleotides or polypeptides, or agonists or antagonists of follistatin-3, could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, follistatin-3 polynucleotides or polypeptides, or agonists or antagonists of follistatin-3, can also be used to modulate hemostatic (the stopping of bleeding) or thrombolytic activity (clot formation). For example, by increasing hemostatic or thrombolytic activity, follistatin-3 polynucleotides or polypeptides, or agonists or antagonists of follistatin-3, could be used to treat blood coagulation disorders (e.g., afibrinogenemia, factor deficiencies), blood platelet disorders (e.g. thrombocytopenia), or wounds resulting from trauma, surgery, or other causes. Alternatively, follistatin-3 polynucleotides or polypeptides, or agonists or antagonists of follistatin-3, that can decrease hemostatic or thrombolytic activity could be used to inhibit or dissolve clotting, important in the treatment of heart attacks (infarction), strokes, or scarring.

Follistatin-3 polynucleotides or polypeptides, or agonists or antagonists of follistatin-3, may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of follistatin-3 polynucleotides or polypeptides, or agonists or antagonists of follistatin-3, that can inhibit an immune response, particularly the proliferation, differentiation, or chemotaxis of T-cells, may be an effective therapy in preventing autoimmune disorders.

Examples of autoimmune disorders that can be treated or detected include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by follistatin-3 polynucleotides or polypeptides, or agonists or antagonists of follistatin-3. Moreover, these molecules can be used to treat anaphylaxis, hypersensitivity to an antigenic molecule, or blood group incompatibility.

Follistatin-3 polynucleotides or polypeptides, or agonists or antagonists of follistatin-3, may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of follistatin-3 polynucleotides or polypeptides, or agonists or antagonists of follistatin-3, that inhibits an immune response, particularly the proliferation, differentiation, or chemotaxis of T-cells, may be an effective therapy in preventing organ rejection or GVHD.

Similarly, follistatin-3 polynucleotides or polypeptides, or agonists or antagonists of follistatin-3, may also be used to modulate inflammation. For example, follistatin-3 polynucleotides or polypeptides, or agonists or antagonists of follistatin-3, may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

Follistatin-3 polynucleotides or polypeptides, or agonists or antagonists of follistatin-3, can be used to treat or detect hyperproliferative disorders, including neoplasms. Follistatin-3 polynucleotides or polypeptides, or agonists or antagonists of follistatin-3, may inhibit the proliferation of the disorder through direct or indirect interactions. Alternatively, follistatin-3 polynucleotides or polypeptides, or agonists or antagonists of follistatin-3, may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by follistatin-3 polynucleotides or polypeptides, or agonists or antagonists of follistatin-3, include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by follistatin-3 polynucleotides or polypeptides, or agonists or antagonists of follistatin-3. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Cardiovascular Disorders

Follistatin-3 polynucleotides or polypeptides, or agonists or antagonists of follistatin-3, encoding follistatin-3 may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Follistatin-3 polynucleotides or polypeptides, or agonists or antagonists of follistatin-3, are especially effective for the treatment of critical limb ischemia and coronary disease. As shown in the Examples, administration of follistatin-3 polynucleotides and polypeptides to an experimentally induced ischemia rabbit hindlimb may restore blood pressure ratio, blood flow, angiographic score, and capillary density.

Follistatin-3 polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Follistatin-3 polypeptides may be administered as part of a pharmaceutical composition, described in more detail below. Methods of delivering follistatin-3 polynucleotides are described in more detail herein.

Angiogenesis

The naturally occurring balance between endogenous stimulators and inhibitors of angiogenesis is one in which inhibitory influences predominate. Rastinejad et al., Cell 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., Biotech. 9:630–634 (1991); Folkman et al., N. Engl. J. Med., 333:1757–1763 (1995); Auerbach et al, J. Microvasc. Res. 29:401–411 (1985); Folkman, Advances in Cancer Research, eds. Klein and Weinhouse, Academic Press, New York, pp. 175–203 (1985); Patz, Am. J. Opthalmol. 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, Science 235:442–447 (1987).

The present invention provides for treatment of diseases or disorders associated with neovascularization by administration of the follistatin-3 polynucleotides and/or polypeptides of the invention, as well as agonists or antagonists of follistatin-3. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)):

Ocular disorders associated with neovascularization which can be treated with the follistatin-3 polynucleotides and polypeptides of the present invention (including follistatin-3 agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. OphIhal.* 22:291–312 (1978).

Additionally, disorders which can be treated with the follistatin-3 polynucleotides and polypeptides of the present invention (including follistatin-3 agonist and/or antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated with be treated with the follistatin-3 polynucleotides and polypeptides of the present invention (including follistatin-3 agonist and/or antagonists) include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (*Rochele minalia quintosa*), ulcers (*Helicobacter pylori*), Bartonellosis and bacillary angiomatosis.

Diseases at the Cellular Level

Diseases associated with increased cell survival or the inhibition of apoptosis that could be treated or detected by follistatin-3 polynucleotides or polypeptides, as well as antagonists or agonists of follistatin-3, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, follistatin-3 polynucleotides, polypeptides, and/or antagonists of the invention are used to inhibit growth, progression, and/or metasis of cancers, in particular those listed above.

Additional diseases or conditions associated with increased cell survival that could be treated or detected by follistatin-3 polynucleotides or polypeptides, or agonists or antagonists of follistatin-3, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by follistatin-3 polynucleotides or polypeptides, as well as agonists or antagonists of follistatin-3, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing follistatin-3 polynucleotides or polypeptides, as well as agonists or antagonists of follistatin-3, for therapeutic purposes, for example, to stimulate epithelial cell proliferation and basal keratinocytes for the purpose of wound healing, and to stimulate hair follicle production and healing of dermal wounds. follistatin-3 polynucleotides or polypeptides, as well as agonists or antagonists of follistatin-3, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associed with systemic treatment with steroids, radiation therapy and antineoplastic drugs and antimetabolites. Follistatin-3 polynucleotides or polypeptides, as well as agonists or antagonists of follistatin-3, could be used to promote dermal reestablishment subsequent to dermal loss Follistatin-3 polynucleotides or polypeptides, as well as agonists or antagonists of follistatin-3, could be used to increase the adherence of skin grafts to a wound bed and to stimulate re-epithelialization from the wound bed. The following are types of grafts that follistatin-3 polynucleotides or polypeptides, agonists or antagonists of follistatin-3, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. follistatin-3 polynucleotides or polypeptides, as well as agonists or antagonists of follistatin-3, can be used to promote skin strength and to improve the appearance of aged skin.

It is believed that follistatin-3 polynucleotides or polypeptides, as well as agonists or antagonists of follistatin-3, will also produce changes in hepatocyte proliferation, and epithelial cell proliferation in the lung, breast, pancreas, stomach, small intesting, and large intestine. Follistatin-3 polynucleotides or polypeptides, as well as agonists or antagonists of follistatin-3, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. Follistatin-3 polynucleotides or polypeptides, agonists or antagonists of follistatin-3, may promote proliferation of endothelial cells, keratinocytes, and basal keratinocytes.

Follistatin-3 polynucleotides or polypeptides, as well as agonists or antagonists of follistatin-3, could also be used to reduce the side effects of gut toxicity that result from radiation, chemotherapy treatments or viral infections. Follistatin-3 polynucleotides or polypeptides, as well as agonists or antagonists of follistatin-3, may have a cytoprotective effect on the small intestine mucosa. Follistatin-3 polynucleotides or polypeptides, as well as agonists or antagonists of follistatin-3, may also stimulate healing of mucositis (mouth ulcers) that result from chemotherapy and viral infections.

Follistatin-3 polynucleotides or polypeptides, as well as agonists or antagonists of follistatin-3, could further be used in full regeneration of skin in full and partial thickness skin defects, including burns, (i.e., repopulation of hair follicles, sweat glands, and sebaceous glands), treatment of other skin defects such as psoriasis: Follistatin-3 polynucleotides or polypeptides, as well as agonists or antagonists of follistatin-3, could be used to treat epidermolysis bullosa, a defect in adherence of the epidermis to the underlying dermis which results in frequent, open and painful blisters by accelerating reepithelialization of these lesions. Follistatin-3 polynucleotides or polypeptides, as well as agonists or antagonists of follistatin-3, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, follistatin-3 polynucleotides or polypeptides, as well as agonists or antagonists of follistatin-3, could be used to promote the resurfacing of the mucosal surface to aid more rapid healing and to prevent progression of inflammatory bowel disease. Treatment with follistatin-3 polynucleotides or polypeptides, agonists or antagonists of follistatin-3, is expected to have a significant effect on the production of mucus throughout the gastrointestinal tract and could be used to protect the intestinal mucosa from injurious substances that are ingested or following surgery. Follistatin-3 polynucleotides or polypeptides, as well as agonists or antagonists of follistatin-3, could be used to treat diseases associate with the under expression of follistatin-3.

Moreover, follistatin-3 polynucleotides or polypeptides, as well as agonists or antagonists of follistatin-3, could be used to prevent and heal damage to the lungs due to various pathological states. A growth factor such as follistatin-3 polynucleotides or polypeptides, as well as agonists or antagonists of follistatin-3, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated using follistatin-3 polynucleotides or polypeptides, agonists or antagonists of follistatin-3. Also, follistatin-3 polynucleotides or polypeptides, as well as agonists or antagonists of follistatin-3, could be used to stimulate the proliferation of and differentiation of type II pneumocytes, which may help treat or prevent disease such as hyaline membrane diseases, such as infant respiratory distress syndrome and bronchopulmonary displasia, in premature infants.

Follistatin-3 polynucleotides or polypeptides, as well as agonists or antagonists of follistatin-3, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, follistatin-3 polynucleotides or polypeptides, as well as agonists or antagonists of follistatin-3, could be used treat or prevent the onset of diabetes mellitus. In patients with newly diagnosed Types I and II diabetes, where some islet cell function remains, follistatin-3 polynucleotides or polypeptides, as well as agonists or antagonists of follistatin-3, could be used to maintain the islet function so as to alleviate, delay or prevent permanent manifestation of the disease. Also, follistatin-3 polynucleotides or polypeptides, as well as agonists or antagonists of follistatin-3, could be used as an auxiliary in islet cell transplantation to improve or promote islet cell function.

Infectious Disease

Follistatin-3 polynucleotides or polypeptides, or agonists or antagonists of follistatin-3, can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, follistatin-3 polynucleotides or polypeptides, or agonists or antagonists of follistatin-3, may also directly inhibit the infectious agent, without necessarily eliciting an immune response.

Viruses are one example of an infectious agent that can cause disease or symptoms that can be treated or detected by follistatin-3 polynucleotides or polypeptides, or agonists or antagonists of follistatin-3. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. Follistatin-3 polynucleotides or polypeptides, or agonists or antagonists of follistatin-3, can be used to treat or detect any of these symptoms or diseases.

Similarly, bacterial or fungal agents that can cause disease or symptoms and that can be treated or detected by follistatin-3 polynucleotides or polypeptides, or agonists or antagonists of follistatin-3, include, but not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Klebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Follistatin-3 polynucleotides or polypeptides, or agonists or antagonists of follistatin-3, can be used to treat or detect any of these symptoms or diseases.

Moreover, parasitic agents causing disease or symptoms that can be treated or detected by follistatin-3 polynucleotides or polypeptides, or agonists or antagonists of follistatin-3, include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. Follistatin-3 polynucleotides or polypeptides, or agonists or antagonists of follistatin-3, can be used to treat or detect any of these symptoms or diseases.

Preferably, treatment using follistatin-3 polynucleotides or polypeptides, or agonists or antagonists of follistatin-3, could either be by administering an effective amount of follistatin-3 polypeptide to the patient, or by removing cells from the patient, supplying the cells with follistatin-3 polynucleotide, and returning the engineered cells to the patient (ex vivo therapy). Moreover, the follistatin-3 polypeptide or polynucleotide can be used as an antigen in a vaccine to raise an immune response against infectious disease.

Regeneration

Follistatin-3 polynucleotides or polypeptides, or agonists or antagonists of follistatin-3, can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, follistatin-3 polynucleotides or polypeptides, or agonists or antagonists of follistatin-3, may increase regeneration of tissues difficult to heal. For example, increased tendon/ligament regeneration would quicken recovery time after damage. Follistatin-3 polynucleotides or polypeptides, or agonists or antagonists of follistatin-3, of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using follistatin-3 polynucleotides or polypeptides, or agonists or antagonists of follistatin-3, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the follistatin-3 polynucleotides or polypeptides, or agonists or antagonists of follistatin-3.

Chemotaxis

Follistatin-3 polynucleotides or polypeptides, or agonists or antagonists of follistatin-3, may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

Follistatin-3 polynucleotides or polypeptides, or agonists or antagonists of follistatin-3, may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. As a chemotactic molecule, follistatin-3 could also attract fibroblasts, which can be used to treat wounds.

It is also contemplated that follistatin-3 polynucleotides or polypeptides, or agonists or antagonists of follistatin-3, may inhibit chemotactic activity. These molecules could also be used to treat disorders. Thus, follistatin-3 polynucleotides or pypeptides, or agonists or antagonists of follistatin-3, could be used as an inhibitor of chemotaxis.

Binding Activity

Follistatin-3 polypeptides may be used to screen for molecules that bind to follistatin-3 or for molecules to which follistatin-3 binds. The binding of follistatin-3 and the molecule may activate (agonist), increase, inhibit (antagonist), or decrease activity of the follistatin-3 or the molecule bound. Examples of such molecules include antibodies, oligonucleotides, proteins (e.g., receptors),or small molecules.

Preferably, the molecule is closely related to the natural ligand of follistatin-3, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which follistatin-3 binds, or at least, a fragment of the receptor capable of being bound by follistatin-3 (e.g., active site). In either case, the molecule can be rationally designed using known techniques.

Preferably, the screening for these molecules involves producing appropriate cells which express follistatin-3, either as a secreted protein or on the cell membrane. Preferred cells include cells from mammals, yeast, Drosophila, or *E. coli*. Cells expressing follistatin-3 (or cell membrane containing the expressed polypeptide) are then preferably contacted with a test compound potentially containing the molecule to observe binding, stimulation, or inhibition of activity of either follistatin-3 or the molecule.

The assay may simply test binding of a candidate compound to follistatin-3, wherein binding is detected by a label, or in an assay involving competition with a labeled competitor. Further, the assay may test whether the candidate compound results in a signal generated by binding to follistatin-3.

Alternatively, the assay can be carried out using cell-free preparations, polypeptide/molecule affixed to a solid support, chemical libraries, or natural product mixtures. The assay may also simply comprise the steps of mixing a candidate compound with a solution containing follistatin-3, measuring follistatin-3/molecule activity or binding, and comparing the follistatin-3/molecule activity or binding to a standard.

Preferably, an ELISA assay can measure follistatin-3 level or activity in a sample (e.g., biological sample) using a monoclonal or polyclonal antibody. The antibody can measure follistatin-3 level or activity by either binding, directly or indirectly, to follistatin-3 or by competing with follistatin-3 for a substrate.

Additionally, the receptor to which follistatin-3 binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of follistatin-3 thereby effectively generating agonists and antagonists of follistatin-3. See generally, U.S. Pat. Nos. 5,605,793, 5,811,238, 5,830,721, 5,834,252, and 5,837,458, and Patten, P. A., et al., *Curr. Opinion Biotechnol.* 8:724–33 (1997); Harayama, S. *Yrends Biotechnol.* 16(2):76–82 (1998); Hansson, L. O., et al., *J. Mol. Biol.* 287:265–76 (1999); and Lorenzo, M. M. and Blasco, R. *Biotechniques* 24(2):308–13 (1998) (each of these patents and publications are hereby incorporated by reference). In one embodiment, alteration of follistatin-3 polynucleotides and corresponding polypeptides may be achieved by DNA shuffling. DNA shuffling involves the assembly of two or more DNA segments into a desired follistatin-3 molecule by homologous, or site-specific, recombination. In another embodiment, follistatin-3 polynucleotides and corresponding polypeptides may be alterred by being subjected to random mutagenesis by error-prone PCR, random nucleotide insertion or other methods prior to recombination. In another embodiment, one or more components, motifs, sections, parts, domains, fragments, etc., of follistatin-3 may be recombined with one or more components, motifs, sections, parts, domains, fragments, etc. of one or more heterologous molecules. In preferred embodiments, the heterologous molecules are follistatin-3 family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active follistatin-3 fragments. Biologically active fragments are those exhibiting activity similar, but not necessarily identical, to an activity of the follistatin-3 polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and $^3$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of [$^3$H] thymidine in each case. The amount of fibroblast cell proliferation is measured by liquid scintillation chromatography which measures the incorporation of [$^3$H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the follistatin-3 receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat disease or to bring about a particular result in a patient (e.g., blood vessel growth) by activating or inhibiting the follistatin-3/molecule. Moreover, the assays can discover agents which may inhibit or enhance the production of follistatin-3 from suitably manipulated cells or tissues.

Therefore, the invention includes a method of identifying compounds which bind to follistatin-3 comprising the steps of: (a) incubating a candidate binding compound with follistatin-3; and (b) determining if binding has occurred. Moreover, the invention includes a method of identifying agonists/antagonists comprising the steps of: (a) incubating a candidate compound with follistatin-3, (b) assaying a biological activity, and (b) determining if a biological activity of follistatin-3 has been altered.

Antisense And Ribozyme Antagonists

In specific embodiments, antagonists according to the present invention are nucleic acids corresponding to the sequences contained in SEQ ID NO:1, or the complementary strand thereof, and/or to nucleotide sequences contained in the deposited clone follistatin-3. In one embodiment, antisense sequence is generated internally by the organism, in another embodiment, the antisense sequence is separately administered (see, for example, O'Connor, J., Neurochem. 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the follistatin-3 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the follistatin-3 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding follistatin-3, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise a sequence complementary to at least a portion of an RNA transcript of a follistatin-3 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded follistatin-3 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a follistatin-3 RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of follistatin-3 shown in FIGS. 1A, 1B, and 1C could be used in an antisense approach to inhibit translation of endogenous follistatin-3 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of follistatin-3 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, Bio Techniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–745 1), etc.

While antisense nucleotides complementary to the follistatin-3 coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy follistatin-3 mRNAs, the use of hammerhead ribozymes is preferred. Hammerhead ribozymes cleave mRNAs at locations dictated by flanking regions that form complementary base pairs with the target mRNA. The sole requirement is that the target m.RNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of follistatin-3 (FIGS. 1A, 1B, and 1C). Preferably, the ribozyme is engineered so that the cleavage recognition site is located near the 5' end of the follistatin-3 mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express follistatin-3 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous follistatin-3 messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery.

Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Other Activities

The polypeptide of the present invention, as a result of the ability to stimulate vascular endothelial cell growth, may be employed in treatment for stimulating revascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat and prevent neuronal damage which occurs in certain neuronal disorders or neuro-degenerative conditions such as Alzheimer's disease, Parkinson's disease, and AIDS-related complex. Follistatin-3 may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The follistatin-3 polypeptide may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The follistatin-3 polypeptide may also be employed to maintain organs before transplantation or for supporting cell culture of primary tissues.

The polypeptide of the present invention may also be employed for inducing tissue of mesodermal origin to differentiate in early embryos.

Follistatin-3 polynucleotides or polypeptides, or agonists or antagonists of follistatin-3, may also increase or decrease the differentiation or proliferation of embryonic stem cells, besides, as discussed above, hematopoietic lineage.

Follistatin-3 polynucleotides or polypeptides, or agonists or antagonists of follistatin-3, may also be used to modulate mammalian characteristics, such as body height, weight, hair color, eye color, skin, percentage of adipose tissue, pigmentation, size, and shape (e.g., cosmetic surgery). Similarly, follistatin-3 polynucleotides or polypeptides, or agonists or antagonists of follistatin-3, may be used to modulate mammalian metabolism affecting catabolism, anabolism, processing, utilization, and storage of energy.

Follistatin-3 polynucleotides or polypeptides, or agonists or antagonists of follistatin-3, may be used to change a mammal's mental state or physical state by influencing biorhythms, caricadic rhythms, depression (including depressive disorders), tendency for violence, tolerance for pain, reproductive capabilities (preferably by Activin or Inhibin-like activity), hormonal or endocrine levels, appetite, libido, memory, stress, or other cognitive qualities.

Follistatin-3 polynucleotides or polypeptides, or agonists or antagonists of follistatin-3, may also be used as a food additive or preservative, such as to increase or decrease storage capabilities, fat content, lipid, protein, carbohydrate, vitamins, minerals, cofactors or other nutritional components.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

Having generally described the invention, the same will be more readily understood by reference to the following examples, which are provided by way of illustration and are not intended as limiting.

Having generally described the invention, the same will be more readily understood by reference to the following examples, which are provided by way of illustration and are not intended as limiting.

Having generally described the invention, the same will be more readily understood by reference to the following examples, which are provided by way of illustration and are not intended as limiting.

EXAMPLES

Example 1(a)

Expression and Purification of "His-tagged" Follistatin-3 in *E. coli*

The bacterial expression vector pHE-4 is used for bacterial expression in this example. pHE-4 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the amino terminus of that polypeptide.

The DNA sequence encoding the desired portion of the follistatin-3 protein comprising the mature form of the follistatin-3 amino acid sequence is amplified from the deposited cDNA clone using PCR oligonucleotide primers which anneal to the amino terminal sequences of the desired portion of the follistatin-3 protein and to sequences in the deposited construct 3' to the cDNA coding sequence. Additional nucleotides containing restriction sites to facilitate cloning in the pHE-4 vector are added to the 5' and 3' primer sequences, respectively.

For cloning the mature form of the follistatin-3 protein, the 5' primer has the sequence 5' TCA CGC <u>CAT ATG</u> GGC TCG GGG AAC C 3' (SEQ ID NO:12) containing the underlined Nde I restriction site followed by 16 nucleotides of the amino terminal coding sequence of the mature follistatin-3 sequence in SEQ ID NO:2. One of 5 ordinary skill in the art would appreciate, of course, that the point in the protein coding sequence where the 5' primer begins may be varied to amplify a DNA segment encoding any desired portion of the complete follistatin-3 protein shorter or longer than the mature form of the protein. The 3' primer has the sequence 5' CAT CCG <u>GGT ACC</u> TTA TTA CAC GAA GTT CTC TTC CTC TTC TG 3' (SEQ ID NO:13) containing the underlined Asp 718 restriction site followed by two stop codons and 23 nucleotides complementary to the 3' end of the coding sequence of the follistatin-3 DNA sequence in FIG. 1A.

The amplified follistatin-3 DNA fragment and the vector pHE4 are digested with Nde I and Asp 718 and the digested DNAs are then ligated together. Insertion of the follistatin-3 DNA into the restricted pHE4 vector places the follistatin-3 protein coding region downstream from the IPTG-inducible promoter and in-frame with an initiating AUG and the six histidine codons.

The ligation mixture is transformed into competent *E. coli* cells using standard procedures such as those described by Sambrook and colleagues (*Molecular Cloning: a Laboratory Manual, 2nd Ed.*; Cold Spring Harbor Laboratory Press, Cold Spring Harbor, NY (1989)). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing follistatin-3 protein, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. Isopropyl-beta-D-thiogalactopyranoside ("IPTG") is then added to a final concentration of 1 mN to induce transcription from the lac repressor sensitive promoter, by inactivating the lacI repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the follistatin-3 is loaded onto a nickel-nitrilo-tri-acetic acid ("Ni-NTA") affinity resin column (QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the follistatin-3 is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1 M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

The following alternative method may be used to purify follistatin-3 expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5 M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the follistatin-3 polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded follistatin-3 polypeptide solution, a previously prepared tangential filtration unit equipped with 0.16 micrometer membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the follistatin-3 polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the follistatin-3 polypeptide (determined, for instance, by 16% SDS-PAGE) are then pooled.

The resultant follistatin-3 polypeptide exhibits greater than 95% purity after the above refolding and purification steps. No major contaminant bands are observed from Commassie blue stained 16% SDS-PAGE gel when 5 micrograms of purified protein is loaded. The purified protein is also tested for endotoxin/LPS contamination, and typically the LPS content is less than 0.1 ng/ml according to LAL assays.

Example 2

Cloning and Expression of Follistatin-3 protein in a Baculovirus Expression System In this illustrative example, the plasmid shuttle vector pA2 is used to insert the cloned DNA encoding complete protein, including its naturally associated secretory signal (leader) sequence, into a baculovirus to express the mature follistatin-3 protein, using standard methods as described by Summers and colleagues (*A Manual of Methods for Baculovirus Vectors and Insect Cell Culture Procedures*, Texas Agricultural Experimental Station Bulletin No. 1555 (1987)). This expression vector contains the strong polyhedrin promoter of the *Autographa californica* nuclear polyhedrosis virus (AcMNPV) followed by convenient restriction sites such as Bam HI, Xba I and Asp 718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, by Luckow and coworkers (Virology 170:31–39 (1989)).

The cDNA sequence encoding the full length follistatin-3 protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5' CAT CGC <u>GGA TCC</u> GCC ATC ATG CGT CCC GGG GCG CCA GGG C 3' (SEQ ID NO:14) containing the underlined Bam HI restriction enzyme site, an efficient signal for initiation of translation in eukaryotic cells (Kozak, M., *J. Mol. Biol.* 196:947–950 (1987)), followed by 22 of nucleotides of the sequence of the complete follistatin-3 protein shown in FIG. 1A, beginning with the AUG initiation codon. The 3' primer has the sequence 5' CAT CCG <u>GGT ACC</u> TCA CAC GAA GTT CTC TTC CTC TTC TG 3' (SEQ ID NO:15) containing the underlined Asp 718 restriction site followed by 23 nucleotides complementary to the 3' noncoding sequence in FIG. 1A.

The amplified fragment is isolated from a 1% agarose gel using a commercially available kit ("Geneclean," BIO 101 Inc., La Jolla, Calif.). The fragment then is digested with Bam HI and Asp 718 and again is purified on a 1% agarose gel. This fragment is designated herein F1.

The plasmid is digested with the restriction enzymes Bam HI and Asp 718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB 101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human follistatin-3 gene by digesting DNA from individual colonies using Bam HI and Asp 718 and then analyzing the digestion product by gel electrophoresis. The sequence of the cloned fragment is confirmed by DNA sequencing. This plasmid is designated herein pA2Follistatin-3.

Five µg of the plasmid pA2Follistatin-3 is co-transfected with 1.0 µg of a commercially available linearized baculovirus DNA ("BaculoGold™ baculovirus DNA", Pharmingen, San Diego, Calif.), using the lipofection method described by Feigner and colleaguew (*Proc. Natl. Acad. Sci. USA* 84:7413–7417 (1987)). One µg of BaculoGold™ virus DNA and 5 µg of the plasmid pA2Follistatin-3 are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith (supra). An agarose gel with "Blue Gal" (Life Technologies Inc., Gaithersburg) is used to allow easy identification and isolation of gal expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-Follistatin-3.

To verify the expression of the follistatin-3 gene Sf9 cells are grown in Grace's medium supplemented with 10% heat-inactivated FBS. The cells are infected with the recombinant baculovirus V-Follistatin-3 at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature form of the follistatin-3 protein, and thus the cleavage point and length of the naturally associated secretory signal peptide.

Example 3

Cloning and Expression of Follistatin-3 in Mammalian Cells

A typical mammalian expression vector contains the promoter element, which mediates the initiation of transcription of mRNA, the protein coding sequence, and 25 signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, RIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS; Murphy, et al., *Biochem J*. 227:277–279 (1991); Bebbington, et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen, et al., *Mol. Cel. Biol*. 5:438–447 (1985)) plus a fragment of the CMV-enhancer (Boshart, et al., *Cell* 41:521–530 (1985)). Multiple cloning sites, e.g., with the restriction enzyme cleavage sites Bam HI, Xba I and Asp 718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pFollistatin-3HA, is made by cloning a portion of the cDNA encoding the mature form of the follistatin-3 protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson and colleagues (*Cell* 37:767 (1984)). The fusion of the HA tag to the target protein allows easy detection and recovery of the recombinant protein with an antibody that recognizes the HA epitope. pcDNAIII contains, in addition, the selectable neomycin marker.

A DNA fragment encoding the complete follistatin-3 polypeptide is cloned into the polylinker region of the vector so that recombinant protein expression is directed by the CMV promoter. The plasmid construction strategy is as follows. The follistatin-3 cDNA of the deposited clone is amplified using primers that contain convenient restriction sites, much as described above for construction of vectors for expression of follistatin-3 in *E. coli*. Suitable primers include the following, which are used in this example. The 5' primer, containing the underlined Bam HI site, a Kozak sequence, an AUG start codon, and 22 nucleotides of the 5' coding region of the complete follistatin-3 polypeptide, has the following sequence: 5'-CAT CGC GGA TCC GCC ACC ATG CGT CCC GGG GCG CCA GGG C-3' (SEQ ID NO:16). The 3' primer, containing the underlined Asp 718 and 23 of nucleotides complementary to the 3' coding sequence immediately before the stop codon, has the following sequence: 5'-TCA CCG CTC GAG CAC GAA GTT CTC TTC CTC TTC TG-3' (SEQ ID NO:17).

The PCR amplified DNA fragment and the vector, pcDNAI/Amp, are digested with Bam HI and Asp 718 and then ligated. The ligation mixture is transformed into *E. coli* strain SURE (Stratagene Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the complete follistatin-3 polypeptide.

For expression of recombinant follistatin-3, COS cells are transfected with an expression vector, as described above, using DEAE-dextran, as described, for instance, by Sambrook and coworkers (*Molecular Cloning: a Laboratory Manual*, Cold Spring Laboratory Press, Cold Spring Harbor, N.Y. (1989)). Cells are incubated under conditions for expression of follistatin-3 by the vector.

Expression of the follistatin-3-HA fusion protein is detected by radiolabeling and immunoprecipitation, using methods described in, for example Harlow and colleagues (*Antibodies: A Laboratory Manual*, 2nd Ed.; Cold Spring Harbor Laboratory Press, Cold Spring Harbor, N.Y. (1988)). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson and colleagues (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of follistatin-3 polypeptide. Plasmid pC4 is a derivative of the plasmid pSV2-dhfr (ATCC® Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., et al., *J. Biol. Chem.* 253:1357–1370 (1957); Hamlin, J. L. and Ma, C. *Biochem. et Biophys. Acta*, 1097:107–143 (1990); Page, M. J. and Sydenham, M. A. *Biotechnology* 9:64–68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Mol. Cell. Biol.* 5:438–447 (1985)) plus a fragment isolated from the enhancer of the immediate early gene of human cytomegalovirus (CMV; Boshart, et al., *Cell* 41:521–530 (1985)). Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the follistatin-3 polypeptide in a regulated way in mammalian cells (Gossen, M., and Bujard, H. *Proc. Natl. Acad. Sci. USA* 89:5547–5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphates by procedures known in the art. The vector is then isolated from a 1% agarose gel. The DNA sequence encoding the complete follistatin-3 polypeptide is amplified using PCR oligonucleotide primers corresponding to the 5' and 3' sequences of the desired portion of the gene. The 5' primer containing the underlined Bam HI site, a Kozak sequence, an AUG start codon, and 22 nucleotides of the 5' coding region of the complete follistatin-3 polypeptide, has the following sequence: 5' CAT CGC GGA TCC GCC ACC ATG CGT CCC GGG GCG CCA GGG C 3' (SEQ ID NO:18). The 3' primer, containing the underlined Asp 718 restriction site and 23 of nucleotides complementary to the 3' coding sequence immediately before the stop codon as shown in FIG. 1A (SEQ ID NO:1), has the following sequence: 5' CAT CCG GGT ACC TCA CAC GAA GTT CTC TTC CTC TTC TG 3' (SEQ ID NO:19).

The amplified fragment is digested with the endonucleases Bam HI and Asp 718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five $\mu$g of the expression plasmid pC4 is cotransfected with 0.5 $\mu$g of the plasmid pSVneo using lipofectin (Feigner, et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 $\mu$M, 2 $\mu$M, 5 $\mu$M, 10 mM, 20 mM). The same procedure is repeated until clones are obtained which grow at a concentration of 100–200 μM. Expression of the desired gene product is analyzed, for instance, by SDS-PAGE and Western blot or by reversed phase HPLC analysis.

Example 4

Tissue Distribution of Follistatin-3 mRNA Expression

Northern blot analysis was carried out to examine follistatin-3 gene expression in human tissues, using methods described by, among others, Sambrook and colleagues (supra). A cDNA probe containing the entire nucleotide sequence of the follistatin-3 protein (SEQ ID NO:1) was labeled with $^{32}$P using the rediprime™ DNA labeling system (Amersham Life Science), according to manufacturer's instructions. After labeling, the probe was purified using a CHROMA SPIN-100™ column (Clontech Laboratories, Inc.), according to manufacturer's protocol number PT1200-1. The purified labeled probe was then used to examine various human tissues for follistatin-3 mRNA.

Multiple Tissue Northern (MTN) blots containing various human tissues (H) or human immune system tissues (IM) were obtained from Clontech and were examined with the labeled probe using ExpressHyb™ hybridization solution (Clontech) according to manufacturer's protocol number PT1190-1. Following hybridization and washing, the blots were mounted and exposed to film at −70° C. overnight, and films developed according to standard procedures. The follistatin-3-specific probe recognized an mRNA species of approximately 2.6 kb in most tissues examined.

Example 5

Follistatin-3 Encodes an Activin-binding Protein that is Differentially Regulated Compared of Follistatin Follistatin is a glycoslylated, single chain polypeptide that was discovered as an activin-binding protein in the rat ovary. (Vale, W., et al., *Nature* 321, 776–79 (1986); Ling, N., et al., *Nature* 321, 779–82 (1986); Ueno, N., et al., *Proc. Natl. Acad. Sci. U.S.A.* 84, 8282–86 (1987); Esch, F. S., et al., *Mol. Endocrinol.* 1, 849–55 (1987); Nakamura, T., et al., *Science* 247, 836–38 (1990), reviewed in Michel, V., et al., *Molec. Cell. Endocrinol.* 91, 1–11 (1993)). It was shown to inhibit the release of follicle-stimulating hormone (FSH) from the pituitary by binding to activins (Nakamura, T., et al., *Science* 247, 836–38 (1990); Kogawa, K., et al., *Endocrinol.* 128, 1434–40 (1991), reviewed in Vale, W., et al., The inhibin/activin family of hormones and growth factors, In Peptide Growth Factors and Their Receptors II, eds. Sporn, M. B. and Roberts, A. B., (Springer-Verlag) (1990)), indicating that follistatin inhibits activin actions. This has now been confirmed in vitro and in vivo experiments (Nakamura, T., et al., *Science* 247, 836–38 (1990); de Winter, J. P., et al., *Mol. Cell. Endocrinol.* 116, 105–14 (1996); for review see Patel, K. *Int. J. Biochem. Cell Biol.* 30, 1087–93 (1998)). Follistatin prevents binding of activins to their high affinity transmembrane receptors (de Winter, J. P., et al., *Mol. Cell. Endocrinol.* 116, 105–14 (1996)) and it also facilitates clearance of activins by accelerating their endocytotic degradation (Hashimoto, O., et al., *J. Biol. Chem.* 272, 13835–13842 (1997)).

Two forms of follistatin have been identified, follistatin-315 (FS-315) and a carboxyterminally truncated variant, follistatin-288 (FS-288). These two follistatin molecules result from alternative splicing of one primary transcript (Shimasaki, S., et al., *Proc., Natl., Acad. Sci. U.S.A.* 85, 4218–22 (1998)). Among several differences, FS-288 was shown to be more potent than FS-315 in suppressing FSH release in rat anterior pituitary cells (Sugino, K., et al., *J. Biol. Chem.* 268, 15579–87 (1993)). In addition to its activin-binding activity, follistatin binds to other members of the transforming growth factor (TGF)-beta superfamily such as bone morphogenetic proteins 2, 4, and 7 (Fainsod. A., et al., *Mech. Dev.* 63, 39–50 (1997)). The in vivo relevance of these interactions is as yet unclear. The physiological role of follistatin is not limited to the inhibition of FSH release. For example, overexpression of follistatin in the developing Xenopus laevis embryo led to induction of neural tissue (Hemmati-Brivanlou, A., et al., *Cell* 77, 283–95 (1994)). Furthermore, follistatin-deficient mice showed multiple defects and perinatal death (Matzuk, M. M., et al., *Nature* 374, 360–63 (1995)). The defects include those in the muscles, skin, bone and teeth. These data are consistant with the hypothesis that follistatin is involved in multiple physiological functions.

We have recently identified a human follistatin homologue, follistatin-3, from the Human Genome Sciences expressed sequence tag (EST) database (EST clone number HDTAH85). The cDNA of this follistatin homologue is 2.6 kb in length and encodes a protein of 263 amino acids. Hayette et al. have also reported the Follistatin-Related Gene (FLRG) (Hayette, S., et al., *Oncogene* 16, 2949–54 (1998)) whose sequence was identical to our cDNA. FLRG was identified by positional cloning of transcriptional units on chromosome 19 at the t(11;19)(q13;p13) translocation breakpoint. This breakpoint was observed in a case of B cell chronic lymphocytic leukemia. Hayette et al. have also reported on the structural rearrangement of the FLRG locus in a case of non-Hodgkin's lymphoma. These data suggest that FLRG may play a role in leukemogenesis.

In this study, we demonstrate that FLRG is a functional activin-binding protein which, like follistatin, binds both activin A and activin B. However, we demonstrate differential expression in tissues and regulation of follistatin and FLRG expression in cultured keratinocytes. Our results indicate differences in the in vivo) regulation and functions of FLRG and follistatin proteins.

Materials and Methods

Molecular Cloning of Follistatin-3. Searches of the Human Genome Sciences database of expressed sequence tags (ESTs) identified a cDNA clone from a Hodgkin's Lymphoma II library, HDTAH85, that was homologous to part of follistatin. We named this clone follistatin-3. A cDNA probe encompassing the first 417 nucleotides of the predicted coding sequence of follistatin-3 was isolated by performing two rounds of PCR from a human adult liver cDNA library. This FLRG-specific probe was used to obtain a longer clone containing the complete coding sequence and the 3' non-coding region of follistatin-3 from a fetal bone cDNA library.

Transfection and immunoprecipitation experiments. For transfection into mammalian cells, the FLRG open reading frame without 5'- or 3'-untranslated regions was cloned into pcDNA3 vector (Invitrogen) with an in-frame epitope tag, HA (YPYDVPDYA) (SEQ ID NO:20), or Flag (DYKDDDDK) (SEQ ID NO:21) at the carboxyl terminus. Likewise, the human activin betaA open reading frame without 5'- or 3'-untranslated regions was cloned into pcDNA3 vector (Invitrogen) with an in-frame HA tag, and the human activin betaB with an in-frame HA tag or a myc tag (EQKLISEEDL) (SEQ ID NO:22), at the carboxyl termini. Human kidney epithelial 293 cells (ATCC), grown in Dulbecco's modified Eagles medium (DMEM) supplemented with 10% fetal calf serum (FCS), were transfected with expression constructs, such as pcDNA-FLRG-HA, pcDNA-FLRG-Flag, or combinations of FLRG constructs with activin betaA or activin betaB constructs. The transfection was performed using the Lipofectamine method (Life Technology) according to the manufacturer's instructions. The cell culture media were collected 48 hours post-transfection. Cells were harvested at the same time as the culture media. Transfected cells were lysed in NP-40 lysis buffer (20 mM Tris, pH 8.0, 137 mM NaCl, 1% NP-40, 10% Glycerol, 1 mN PMSF, Leupeptin 1.0 μg/ml, EDTA 0.5 mM, NaF 1 mN, F64 1 μg/ml, Aprorinin 1 μg/ml sodium orthovanadate 1 mM,). FLRG proteins in the cell culture supernatants and cell lysates were immunoprecipitated with a monoclonal anti-HA antibody (Roche, Mannheim, Germany; 2 micrograms/10 ml for cell supernatants and 1 microgram/ml for cell lysates), or a monoclonal anti-Flag antibody (Kodak-IBI). The immunoprecipates were separated by reducing SDS PAGE and subsequently by Western blot analyses.

Anti-FLRG antibody. Purified FLRG protein from Baculoviraus/insect cell expression system was used to immunize rabbits. The anti-serum was used at 1: 7,500 dilution for Western blotting.

Northern blot analysis. Three Clontech human multiple tissue Northern blots were hybridized with $^{32}$P-labelled FLRG and follistatin cDNA probes as described by the manufacturer.

Cell culture for RNase protection assays. The immortalized but non-transformed human HaCaT keratinocyte cell line (18) was used for all tissue culture experiments. Cells were cultured in Dulbecco's modified Eagles medium (DMEM) supplemented with 10% fetal calf serum. For the analysis of follistatin and FLRG regulation, cells were grown to confluency in 10-cm culture dishes and rendered quiescent by a 16 hr incubation in serum free DMEM. Cells were subsequently incubated for varying periods in fresh DMEM containing 20 ng/ml epidermal growth factor (EGF), 10 ng/ml keratinocyte growth factor (KGF), or 1 ng/ml transforming growth factor beta1 (TGF-beta1). Aliquots of cells were harvested before and at different time points after treatment with these reagents and used for RNA isolation. FCS and DMEM were purchased from Life Technologies, Inc. Growth factors and cytokines were from Roche (Mannheim, Germany). Each experiment was repeated at least twice.

RNA isolation and RNase protection assay. Total cellular RNA was isolated from HaCaT cells as described by Chomczynski and Sacchi (Chomczynski, P. and Sacchi, N. *Anal. Biochem.* 162, 156–59 (1987)). RNase protection assays were carried out as described (Werner, S., et al., *EMBO J.* 12, 2635–43 (1993)). All protection assays were repeated with a different set of RNAs from independent experiments. A 247 bp fragment corresponding to nt 28–274 of the human FLRG cDNA and a 253 bp fragment corresponding to nt 28–280 of the follistatin gene (Shimasaki, S., et al., *Proc., Natl., Acad. Sci. U.S.A.* 85, 4218–22 (1998)) were used as probes.

Results and Discussion
Expression of FLRG in Mammalian Cells

To elucidate the functions of FLRG, we first expressed FLRG protein in mammalian cells. An expression vector containing the entire open reading frame of FLRG fused to a C-terminal epitope tag, Flag, was transfected into 293 human kidney epithelial cell. Cell lysates and cell culture media were analyzed by Western blot analyses. In both cell lysates and cell culture media, FLRG appeared as a diffuse band of approximately 35 kDa on a Western blot probed with an anti-FLRG antibody. The same 35 kDa band was detected with an anti-tag antibody that recognized the C-terminal Flag-tag on FLRG. The amino acid sequence of FLRG contains a signal peptide and therefore predicts that FLRG is a secreted protein. Our results showed that the FLRG protein was indeed secreted into the cell culture media. However, unlike the intracellular FLRG protein, the secreted FLRG detected by the anti-Flag antibody showed a much weaker signal than that detected by the polyclonal anti-FLRG antibody. One hypothesis for this observation could be that part of the secreted FLRG may have a proteolytically clipped C-terminus. The predicted molecular weight of FLRG is 27.6 kDa. The difference between the predicted and the apparent molecular weight (35 kDa) could be accounted for by glycosylation of the FLRG protein. In fact, the FLRG amino acid sequence contains two predicted N-glycosylation sites (aa 73 and aa 215) (Hayette, S., et al., *Oncogene* 16, 2949–54 (1998)). Furthermore, thue diffuseness of the FLRG protein band on the Western blot also suggests that FLRG is glycosylated.

Binding of FLRG to Activin A and B

Activin exists as homo- or heterodimers of a betaA and a betaB chain. Three activins, activin A (betaAbetaA homodimer), activin B (betaBbetaB homodimer), and activin AB (betaAbetaB heterodimer) all bind follistatin with high affinities. Activins are synthesized as large precursor polypeptides which are proteolytically processed into mature polypeptides. The disulfide-linked dimers of mature activins form the biologically active molecules of approximately 28 kDa. Under reducing conditions, the dimers can be separated into two subunits of approximately 14 kDa (reviewed in Vale, W., et al., *The inhibin/activin family of hormones and growth factors*, In Peptide Growth Factors and Their Receptors II, eds. Sporn, M. B. and Roberts, A. B., (Springer-Verlag) (1990)).

To determine whether FLRG is able to bind activins, 293 cells were co-transfected with a C-terminal Flag-tagged FLRG construct with either an activin betaA-HA or with an activin betaB-myc expression construct. Flag-tagged follistatin-315 (FS-315) and Flag-tagged follistatin-288 (FS-288), were used as positive controls. These molecules were immunoprecipitated from either the cell culture media or cell lysates with an anti-Flag monoclonal antibody. The co-immunoprecipitated activins A or B were then detected on a Western blot by anti-tag antibodies. Both positive controls, FS-315 and FS-288, co-immunoprecipitated the mature form of Flag-tagged activin A which appeared on the Western blot as the 16 kDa monomer under reducing conditions. In addition, we made a novel observation that FS-315 and FS-288 immunoprecipitated a protein of approximately 55 kDa from the cell lysates. The latter most likely represents the reduced form of activin A precursor. Although this precursor was reported to be inactive in releasing follicle stimulating hormone from pituitary cells in vitro assays (Mason, A. J., et al., *Mol. Endocrinol.* 10: 1055–65 (1996)), follistatin binding to the precursor may prevent the processing of the precursor into the active mature form of activin A. This may, in turn, further inhibit activin A activity.

In cell lysates where FLRG was co-transfected with the activin-betaA cDNA, FLRG co-immunoprecipitated activin A. The ability of FLRG to associate with activin A was comparable to FS-315 and FS-288, as judged from the amounts of FLRG, FS-315, and FS-288 proteins in the immunoprecipitates. The major activin A species precipitated from cell lysates by FLRG was the high molecular weight form of ~55 kDa under reducing conditions. In control experiments where activin betaA was transfected alone or co-transfected with pcDNA vector, no activin A was immunoprecipitated by the anti-Flag antibody that recognized FLRG. These results demonstrate that FLRG, like FS-315 and FS-288, can bind the unprocessed high molecular weight activin A precursor.

In the cell culture media, secreted FLRG, as well as FS-315 and FS-288, co-immunoprecipitated the secreted low molecular weight mature form activin A, as demonstrated by the detection of the 16 kDa monomeric Flag-tagged activin betaA protein on the Western blot. In addition to the 16 kDa species, FS-288 also precipitated a secreted Flag-tagged activin betaA species of approximately 20 kDa.

In cell lysates where FLRG was co-transfected with activin betaB, FLRG co-immunoprecipitated activin B precursor molecules of 48–55 kDa. Judging from the amounts of FLRG, FS-315, and FS-288 proteins in the immunoprecipitates, the ability of FLRG to co-immunoprecipitate activin B was at least as good as that of FS-315 and possibly even better than that of FS-288. In control experiments in which activin betaB cDNA was transfected alone or co-transfected with pcDNA vector, no activin B was immunoprecipitated by the anti-HA antibody that recognized FLRG.

In a reverse experiment where activin B was immunoprecipitated by an anti-myc antibody, FLRG, FS-315, and FS-288 all co-immunoprecipitated with activin B. These results further support the specificity of the interaction between FLRG and activin B.

In the cell culture media, secreted FLRG co-immunoprecipitated the secreted, low molecular weight mature form of activin B as demonstrated by the detection of the 14 kDa monomeric betaB protein on the Western blot. In addition, secreted FLRG also co-immunoprecipitated the secreted high molecular weight precursor form of activin B as demonstrated by the detection of the 55 kDa monomeric betaB protein on the Western blot.

Differential Expression of FLRG and Follistatin.

To gain insight into possible in vivo functions of FLRG, we analyzed FLRG and follistatin expression in various human tissues. FLRG was expressed at highest levels in the testis, adrenal glands, lung, heart and liver. Lower levels of FLRG transcripts were seen in the stomach, small intestine, colon, pancreas, thyroid, ovary and prostate. FLRG mRNA could not be detected in the thymus, kidney, skeletal muscle, liver, brain, peripheral blood lymphocytes and spleen. The expression pattern of follistatin mRNA revealed obvious similarities to that of FLRG, although this molecule was also expressed in the liver. The FLRG expression data extend the results obtained by Hayette et al. (Hayette, S., et al., Oncogene 16, 2949–54 (1998)), who found expression of this molecule in murine heart, lung, testis, and kidney. In contrast to these data, however, we could not detect FLRG mRNA in the human kidney.

To determine potential differences in the regulation of follistatin and FLRG expression, we analyzed the effect of various growth factors and cytokines on the expression of these genes in HaCaT keratinocytes. This cell line was chosen since it expresses fairly high levels of both follistatin and FLRG mRNA. Cells were rendered quiescent by serum starvation and treated with the epithelial mitogens KGF and EGF. Follistatin and FLRG mRNAs were hardly detectable in quiescent keratinocytes. Upon addition of the growth factors, a strong induction of follistatin expression was observed, whereby maximal levels were seen 8 hours after addition of the mitogen. EGF was the more potent inducer compared to KGF. This induction was long-lasting and follistatin mRNA levels had still not returned to basal levels 24 hours after growth factor stimulation. In contrast to follistatin, FLRG induction occurred already within one hour after addition of the growth factors. However, the degree of induction was significantly lower.

To determine whether follistatin and FLRG mRNA induction is specific for epithelial cell mitogens, we analyzed the effect of TGF-beta1, a strong inhibitor of keratinocyte proliferation. Interestingly, TGF-beta1 caused a strong induction of both FS and FLRG expression, whereby the degree of induction was similar for both genes. Similar as with EGF and KGF, induction of FLRG expression by TGF-beta1 occurred earlier compared to follistatin.

Taken together, these results demonstrate differential regulation of follistatin and FLRG mRNA expression, indicating that the two proteins might be available under different biological circumstances. The discovery of a novel activin-binding protein with a different expression pattern compared to follistatin necessitates the reinterpretation of various activin expression data, since the presence of FLRG is likely to modulate the activity of the available activin. Whether this activin-FLRG interaction leads to inhibition of activin function as shown for follistatin remains to be elucidated.

Example 6

Production of an Antibody a) Hybridoma Technology

The antibodies of the present invention can be prepared by a variety of methods. (See, Current Protocols, Chapter 2.) As one example of such methods, cells expressing follistatin-3 is administered to an animal to induce the production of sera containing polyclonal antibodies. In a preferred method, a preparation of follistatin-3 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Kohler et al., *Nature* 256:495 (1975); Kohler et al., Eur. J. Immunol. 6:511 (1976); Kohler et al., Eur. J. Immunol. 6:292 (1976); Hammerling, et al., in: *Monoclonal Antibodies and T-Cell Hybridomas*, Elsevier, N.Y., pp. 563–681 (1981).) In general, such procedures involve immunizing an animal (preferably a mouse) with follistatin-3 polypeptide or, more preferably, with a secreted follistatin-3 polypeptide-expressing cell. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC®. After fusion, the resulting hybridoma cells are selectively maintained in HAT medium, and then cloned by limiting dilution as described by Wands et al. (Gastroenterology 80:15–232 (1981).) The hybridoma cells obtained through such a selection are then assayed to identify clones which secrete antibodies capable of binding the follistatin-3 polypeptide.

Alternatively, additional antibodies capable of binding to follistatin-3 polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the follistatin-3 protein-specific antibody can be blocked by follistatin-3. Such antibodies comprise anti-idiotypic antibodies to the follistatin-3 protein-specific antibody and can be used to immunize an animal to induce formation of further follistatin-3 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted follistatin-3 protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation of Antibody Fragments Directed Against Follistatin-3 from a Library of scfvs.

Naturally occuring V-genes isolated from human PBLs are constructed into a large library of antibody fragments which contain reactivities against follistatin-3 to which the donor may or may not have been exposed (see e.g., U.S. Pat. No. 5,885,793 incorporated herein in its entirety by reference).

Rescue of the Library. A library of scFvs is constructed from the RNA of human PBLs as described in WO92/01047. To rescue phage displaying antibody fragments, approximately $10^9$ E. coli harbouring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, 2×$10^8$ TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 ug/ml ampicillin and 50 ug/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harbouring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the Library. Immunotubes (Nunc) are coated overnight in PBS with 4 ml of either 100 ug/ml or 10 ug/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0 M Tris-HCl, pH 7.4. Phage are then used to infect 10 ml of mid-log E. coli TG1 by incubating eluted phage with bacteria for 30 minutes at 37 degree C. The E. coli are then plated on TYE plates containing 1% glucose and 100 ug/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

Example 7

Method of Determining Alterations in the Follistatin-3 Gene

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degree C. for 30 seconds; 60–120 seconds at 52–58 degree C.; and 60–120 seconds at 70 degree C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of follistatin-3 is also determined and genomic PCR products analyzed to confirm the results. PCR products harboring suspected mutations in follistatin-3 is then cloned and sequenced to validate the results of the direct sequencing.

PCR products of follistatin-3 are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in follistatin-3 not present in unaffected individuals.

Genomic rearrangements are also observed as a method of determining alterations in the follistatin-3 gene. Genomic clones isolated according to methods well-known in the art are nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the follistatin-3 genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of follistatin-3 (hybridized by the probe) are identified as insertions, deletions, and translocations. These follistatin-3 alterations are used as a diagnostic marker for an associated disease.

Example 8

Method of Detecting Abnormal Levels of Follistatin-3 in a Biological Sample

Follistatin-3 polypeptides can be detected in a biological sample, and if an increased or decreased level of follistatin-3 is detected, this polypeptide is a marker for a particular phenotype. Methods of detection are numerous, and thus, it is understood that one skilled in the art can modify the following assay to fit their particular needs.

For example, antibody-sandwich ELISAs are used to detect follistatin-3 in a sample, preferably a biological sample. Wells of a microtiter plate are coated with specific antibodies to follistatin-3, at a final concentration of 0.2 to 10 ug/ml. The antibodies are either monoclonal or polyclonal and are produced by the method described in Example 6. The wells are blocked so that non-specific binding of follistatin-3 to the well is reduced.

The coated wells are then incubated for >2 hours at RT with a sample containing follistatin-3. Preferably, serial dilutions of the sample should be used to validate results. The plates are then washed three times with deionized or distilled water to remove unbounded follistatin-3.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot follistatin-3 polypeptide concentration on the X-axis (log scale) and fluorescence or absorbance of the Y-axis (linear scale). Interpolate the concentration of the follistatin-3 in the sample using the standard curve.

Example 9

Formulation

The invention also provides methods of treatment and/or prevention of diseases, disorders, and/or conditions (such as, for example, any one or more of the diseases, disorders, and/or conditions disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see generally, Langer, Science 249:1527–1533 (1990); Treat et al., in Liposomes in the Therapy of Infectious Disease and Cancer, Lopez-Berestein and Fidler (eds.), Liss, N.Y., pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-IBBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the Therapeutics of the invention, include, but are not limited to, VIRANUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMNE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondii* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAM™, SANDOGLOBULIN™, GAMMAGARD S/D™, and GAMIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PIGF), as disclosed in International Publication Number WO 92/06194; Placental Growth Factor-2 (PIGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE™ (SARGRAMOSTIM™) and NEUPOGEN™ (FILGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 10

Method of Treating Decreased Levels of Follistatin-3

The present invention relates to a method for treating an individual in need of a decreased level of follistatin-3 activity in the body comprising, administering to such an individual a composition comprising a therapeutically effective amount of follistatin-3 antagonist. Preferred antagonists for use in the present invention are follistatin-3-specific antibodies.

Moreover, it will be appreciated that conditions caused by a decrease in the standard or normal expression level of follistatin-3, in an individual can be treated by administering follistatin-3, preferably in the secreted form. Thus, the invention also provides a method of treatment of an individual in need of an increased level of follistatin-3 polypeptide comprising administering to such an individual a pharmaceutical composition comprising an amount of follistatin-3 to increase the activity level of follistatin-3 in such an individual.

For example, a patient with decreased levels of follistatin-3 polypeptide receives a daily dose 0.1–100 ug/kg of the polypeptide for six consecutive days. Preferably, the polypeptide is in the secreted form. The exact details of the dosing scheme, based on administration and formulation, are provided in Example 8.

Example 11

Method of Treating Increased Levels of Follistatin-3

The present invention also relates to a method for treating an individual in need of an increased level of follistatin-3 activity in the body comprising administering to such an individual a composition comprising a therapeutically effective amount of follistatin-3 or an agonist thereof Antisense technology is used to inhibit production of follistatin-3. This technology is one example of a method of decreasing levels of follistatin-3 polypeptide, preferably a secreted form, due to a variety of etiologies, such as cancer.

For example, a patient diagnosed with abnormally increased levels of follistatin-3 is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 8.

Example 12

Method of Treatment Using Gene Therapy—Ex Vivo

One method of gene therapy transplants fibroblasts, which are capable of expressing follistatin-3 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding follistatin-3 can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted follistatin-3.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the follistatin-3 gene is then added to the media and the packaging cells transduced with the vector. The packaging cells now produce infectious viral particles containing the follistatin-3 gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether follistatin-3 protein is produced.

The engineered fibroblasts are then transplanted onto the host, either alone or after having been grown to confluence on cytodex 3 microcarrier beads.

Example 13

Gene Therapy Using Endogenous Follistatin-3 Gene

Another method of gene therapy according to the present invention involves operably associating the endogenous follistatin-3 sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous follistatin-3, flanking the promoter. The targeting sequence will be sufficiently near the 5' end of follistatin-3 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous follistatin-3 sequence. This results in the expression of follistatin-3 in the cell. Expression may be detected by immunological staining, or any other method known in the art.

Fibroblasts are obtained from a subject by skin biopsy. The resulting tissue is placed in DMEM +10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the follistatin-3 locus, plasmid pUC18 (MBI Fermentas, Amherst, N.Y.) is digested with HindIII. The CMV promoter is amplified by PCR with an XbaI site on the 5' end and a BamHI site on the 3' end. Two follistatin-3 non-coding sequences are amplified via PCR: one follistatin-3 non-coding sequence follistatin-3 fragment 1) is amplified with a HindIII site at the 5' end and an Xba site at the 3'end; the other follistatin-3 non-coding sequence (follistatin-3 fragment 2) is amplified with a BamHI site at the 5' end and a HindIII site at the 3'end. The CMV promoter and follistatin-3 fragments are digested with the appropriate enzymes (CMV promoter—XbaI and BamHI; follistatin-3 fragment 1—XbaI; follistatin-3 fragment 2-BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 14

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) follistatin-3 sequences into an animal to increase or decrease the expression of the follistatin-3 polypeptide. The follistatin-3 polynucleotide may be operatively linked to a promoter or any other genetic elements necessary for the expression of the follistatin-3 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3): 470–479, Chao J. et al. (1997) Pharmacol. Res. 35(6): 517–522, Wolff J. A. (1997) Neuromuscul. Disord. 7(5): 314–318, Schwartz B. et al. (1996) Gene Ther. 3(5): 405–411, Tsurumi Y. et al. (1996) Circulation 94(12): 3281–3290 (incorporated herein by reference).

The follistatin-3 polynucleotide constructs may be delivered by any method that delivers injectable materials to the cells of an animal, such as, injection into the interstitial space of tissues (heart, muscle, skin, lung, liver, intestine and the like). The follistatin-3 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the follistatin-3 polynucleotides may also be delivered in liposome formulations (such as those taught in Feigner P. L. et al. (1995) Ann. NY Acad. Sci. 772:126–139 and Abdallah B. et al. (1995) Biol. Cell 85(1):1–7) which can be prepared by methods well known to those skilled in the art.

The follistatin-3 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The follistatin-3 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked follistatin-3 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked follistatin-3 polynucleotide constructs can be delivered to arteries during angioplasty by the catheter used in the procedure.

The dose response effects of injected follistatin-3 polynucleotide in muscle in vivo is determined as follows.

Suitable follistatin-3 template DNA for production of mRNA coding for follistatin-3 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The follistatin-3 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for follistatin-3 protein expression. A time course for follistatin-3 protein expression may be done in a similar fashion except that quadriceps from different mice are harvested at different times. Persistence of follistatin-3 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using follistatin-3 naked DNA.

Example 15

Follistatin-3 Transgenic Animals

The follistatin-3 polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989), etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of follistatin-3 polypeptides, studying conditions and/or disorders associated with aberrant follistatin-3 expression, and in screening for compounds effective in ameliorating such conditions and/or disorders.

Example 16

Follistatin-3 Knock-Out Animals

Endogenous follistatin-3 gene expression can also be reduced by inactivating or "knocking out" the follistatin-3 gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the follistatin-3 polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of follistatin-3 polypeptides, studying conditions and/or disorders associated with aberrant follistatin-3 expression, and in screening for compounds effective in ameliorating such conditions and/or disorders.

Example 17

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay-Purified follistatin-3 protein, or truncated forms thereof, is assessed for its ability to induce activation, proliferation, differentiation or inhibition and/or death in B-cell populations and their precursors. The activity of follistatin-3 protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed Staphylococcus aureus Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R (B220).

Various dilutions of each sample are placed into individual wells of a 96-well plate to which are added $10^5$ B-cells suspended in culture medium (RPMI 1640 containing 10% FBS, $5 \times 10^{-5}$ M 2ME, 100U/ml penicillin, 10 ug/ml streptomycin, and $10^{-5}$ dilution of SAC) in a total volume of 150 ul. Proliferation or inhibition is quantitated by a 20h pulse (luCi/well) with 3H-thymidine (6.7 Ci/mM) beginning 72h post factor addition. The positive and negative controls are IL2 and medium respectively.

In Vivo Assay-BALB/c mice are injected (i.p.) twice per day with buffer only, or 2 mg/Kg of follistatin-3 protein, or truncated forms thereof Mice receive this treatment for 4 consecutive days, at which time they are sacrificed and various tissues and serum collected for analyses. Comparison of H&E sections from normal and follistatin-3 protein-treated spleens identify the results of the activity of follistatin-3 protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from follistatin-3 protein-treated mice is used to indicate whether follistatin-3 protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and follistatin-3 protein-treated mice.

The studies described in this example tested activity in follistatin-3 protein. However, one skilled in the art could easily modify the exemplified studies to test the activity of follistatin-3 polynucleotides (e.g., gene therapy), agonists, and/or antagonists of follistatin-3.

Example 18

T Cell Proliferation Assay

A CD3-induced proliferation assay is performed on PBMCs and is measured by the uptake of $^3$H-thymidine. The assay is performed as follows. Ninety-six well plates are coated with 100 microliters/well of mAb to CD3 (HIT3a, Pharmingen) or isotype-matched control mAb (B33.1) overnight at 4° C. (1 microgram/ml in 0.05M bicarbonate buffer, pH 9.5), then washed three times with PBS. PBMC are isolated by F/H gradient centrifugation from human peripheral blood and added to quadruplicate wells ($5 \times 10^4$/well) of mAb coated plates in RPMI containing 10% FCS and P/S in the presence of varying concentrations of follistatin-3 protein (total volume 200 microliters). Relevant protein buffer and medium alone are controls. After 48 hr. culture at 37° C., plates are spun for 2 min. at 1000 rpm and 100 microliters of supernatant is removed and stored −20° C. for measurement of IL-2 (or other cytokines) if effect on proliferation is observed. Wells are supplemented with 100 microliters of medium containing 0.5 microCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of follistatin-3 proteins.

The studies described in this example tested activity in follistatin-3 protein. However, one skilled in the art could easily modify the exemplified studies to test the activity of follistatin-3 polynucleotides (e.g., gene therapy), agonists, and/or antagonists of follistatin-3.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, in both computer and paper forms, is hereby incorporated by reference in its entirety. Moreover, each of the Sequence Listings submitted with the following applications, in both computer and paper forms, is hereby incorporated by reference in its entirety: U.S. Provisional Application Ser. No. 60/144,088, filed Jul. 16, 1999, U.S. Provisional Application Ser. No. 60/056,248, filed Aug. 29, 1997; U.S. application Ser. No. 09/141,027, filed Aug. 27, 1998; and PCT Application Ser. No. PCT/US98/17710, filed Aug. 27, 1998.

What is claimed is:

1. An isolated protein comprising an amino acid sequence selected from the group consisting of:
   (a) amino acid residues −26 to +237 of SEQ ID NO:2;
   (b) amino acid residues −25 to +217 of SEQ ID NO:2;
   (c) amino acid residues +12 to +217 of SEQ ID NO:2;
   (d) amino acid residues +1 to +237 of SEQ ID NO:2; and
   (e) at least 30 contiguous amino acid residues of amino acid residues −26 to +237 of SEQ ID NO:2.

2. The isolated protein of claim 1 which comprises amino acid sequence (a).

3. The isolated protein of claim 1 which comprises amino acid sequence (b).

4. The isolated protein of claim 1 which comprises amino acid sequence (c).

5. The isolated protein of claim 1 which comprises amino acid sequence (d).

6. The isolated protein of claim 1 which comprises amino acid sequence (e).

7. The isolated protein of claim 1, wherein the amino acid sequence comprises a heterologous polypeptide.

8. The isolated protein of claim 7, wherein the heterologous polypeptide is the Fc domain of immunoglobulin.

9. The isolated protein of claim 1, wherein said isolated protein is glycosylated.

10. A composition comprising the isolated protein of claim 1.

11. A protein produced by a method comprising:
    (a) culturing a host cell under conditions suitable to produce the isolated protein of claim 1; and
    (b) recovering the protein from the host cell culture.

12. An isolated protein comprising an amino acid sequence selected from the group consisting of:
    (a) the amino acid sequence of the full length polypeptide encoded by the cDNA in ATCC Deposit No. 209199;
    (b) the amino acid sequence of the full-length polypeptide, excluding the N-terminal methionine residue, encoded by the human cDNA clone contained in ATCC Deposit No. 209199;
    (c) at least 30 contiguous amino acid residues of the full length polypeptide encoded by the human cDNA clone contained in ATCC Deposit No. 209199;
    (d) the amino acid sequence of the mature polypeptide encoded by the cDNA clone contained in ATCC Deposit No. 209199; and
    (e) a fragment of the polypeptide full length sequence encoded by the cDNA clone contained in ATCC Deposit No. 209199, wherein said fragment binds activin.

13. The isolated protein of claim 12 which comprises amino acid sequence (a).

14. The isolated protein of claim 12 which comprises amino acid sequence (b).

15. The isolated protein of claim 12 which comprises amino acid sequence (c).

16. The isolated protein of claim 12 which comprises amino acid sequence (d).

17. The isolated protein of claim 12 which comprises amino acid sequence (e).

18. The isolated protein of claim 12, wherein the amino acid sequence comprises a heterologous polypeptide.

19. The isolated protein of claim 18, wherein the heterologous polypeptide is the Fc domain of immunoglobulin.

20. The isolated protein of claim 12, wherein said isolated protein is glycosylated.

21. A composition comprising the isolated protein of claim 12.

22. A protein produced by a method comprising:
    (a) culturing a host cell under conditions suitable to produce the isolated protein of claim 12; and
    (b) recovering the protein from the host cell culture.

23. An isolated protein comprising a first amino acid sequence 90% or more identical to a second amino acid sequence selected from the group consisting of:
    (a) amino acid residues −26 to +237 of SEQ ID NO:2;
    (b) amino acid residues +1 to +237 of SEQ ID NO:2; and
    (c) amino acid residues +12 to +217 of SEQ ID NO:2,
    wherein said isolated protein binds activin.

24. The isolated protein of claim 23 which comprises amino acid sequence (a).

25. The isolated protein of claim 23 which comprises amino acid sequence (b).

26. The isolated protein of claim 23 which comprises amino acid sequence (c).

27. The isolated protein of claim 23, wherein the amino acid sequence comprises a heterologous polypeptide.

28. The isolated protein of claim 27, wherein the heterologous polypeptide is the Fc domain of immunoglobulin.

29. The isolated protein of claim 23, wherein said isolated protein is glycosylated.

30. A composition comprising the isolated protein of claim 23.

31. A protein produced by a method comprising:
    (a) culturing a host cell under conditions suitable to produce the isolated protein of claim 23; and
    (b) recovering the protein from the host cell culture.

32. An isolated protein comprising a first amino acid sequence 90% or more identical to a second amino acid sequence selected from the group consisting of:
    (a) the full length amino acid sequence encoded by the cDNA clone contained in ATCC Deposit No. 209199; and (b) the amino acid sequence of the mature polypeptide encoded by the cDNA clone contained in ATCC Deposit No. 209199, wherein said isolated protein binds activin.

33. The isolated protein of claim 32 which comprises amino acid sequence (a).

34. The isolated protein of claim 32 which comprises amino acid sequence (b).

35. The isolated protein of claim 32, wherein the amino acid sequence comprises a heterologous polypeptide.

36. The isolated protein of claim 35, wherein the heterologous polypeptide is the Fc domain of immunoglobulin.

37. The isolated protein of claim 32, wherein said isolated protein is glycosylated.

38. A composition comprising the isolated protein of claim 32.

39. A protein produced by a method comprising:
   (a) culturing a host cell under conditions suitable to produce the isolated protein of claim 32; and
   (b) recovering the protein from the host cell culture.

40. An isolated protein comprising a first amino acid sequence 95% or more identical to a second amino acid sequence selected from the group consisting of:
   (a) amino acid residues −26 to +237 of SEQ ID NO:2;
   (b) amino acid residues +1 to +237 of SEQ ID NO:2; and
   (c) amino acid residues +12 to +217 of SEQ ID NO:2,
   wherein said isolated protein binds activin.

41. The isolated protein of claim 40 which comprises amino acid sequence (a).

42. The isolated protein of claim 40 which comprises amino acid sequence (b).

43. The isolated protein of claim 40 which comprises amino acid sequence (c).

44. The isolated protein of claim 40, wherein the amino acid sequence comprises a heterologous polypeptide.

45. The isolated protein of claim 44, wherein the heterologous polypeptide is the Fc domain of immunoglobulin.

46. The isolated protein of claim 40, wherein said isolated protein is glycosylated.

47. A composition comprising the isolated protein of claim 40.

48. A protein produced by a method comprising:
   (a) culturing a host cell under conditions suitable to produce the isolated protein of claim 40; and
   (b) recovering the protein from the host cell culture.

49. An isolated protein comprising a first amino acid sequence 95% or more identical to a second amino acid sequence selected from the group consisting of:
   (a) the full length amino acid sequence encoded by the cDNA clone contained in ATCC Deposit No. 209199; and
   (b) the amino acid sequence of the mature polypeptide encoded by the cDNA clone contained in ATCC Deposit No. 209199, wherein said isolated protein binds activin.

50. The isolated protein of claim 49 which comprises amino acid sequence (a).

51. The isolated protein of claim 49 which comprises amino acid sequence (b).

52. The isolated protein of claim 49, wherein the amino acid sequence comprises a heterologous polypeptide.

53. The isolated protein of claim 52, wherein the heterologous polypeptide is the Fc domain of immunoglobulin.

54. The isolated protein of claim 49, wherein said isolated protein is glycosylated.

55. A composition comprising the isolated protein of claim 49.

56. A protein produced by a method comprising:
   (a) culturing a host cell under conditions suitable to produce the isolated protein of claim 49; and
   (b) recovering the protein from the host cell culture.

57. An isolated protein comprising an amino acid sequence selected from the group consisting of:
   (a) amino acid residues 14 to 20 of SEQ ID NO:2;
   (b) amino acid residues 46 to 55 of SEQ ID NO:2;
   (c) amino acid residues 88 to 97 of SEQ ID NO:2;
   (d) amino acid residues 113 to 113 of SEQ ID NO:2; and
   (e) amino acid residues 138 to 146 of SEQ ID NO:2.

58. The isolated protein of claim 57, which comprises amino acid sequence (a).

59. The isolated protein of claim 57, which comprises amino acid sequence (b).

60. The isolated protein of claim 57, which comprises amino acid sequence (c).

61. The isolated protein of claim 57, which comprises amino acid sequence (d).

62. The isolated protein of claim 57, which comprises amino acid sequence (e).

63. The isolated protein of claim 57, wherein the amino acid sequence comprises a heterologous polypeptide.

64. The isolated protein of claim 63, wherein the heterologous polypeptide is the Fc domain of immunoglobulin.

65. The isolated protein of claim 57, wherein said isolated protein is glycosylated.

66. A composition comprising the isolated protein of claim 57.

67. A protein produced by a method comprising:
   (a) culturing a host cell under conditions suitable to produce the isolated protein of claim 57; and
   (b) recovering the protein from the host cell culture.

* * * * *

SEQUENCE LISTING

```
<160> NUMBER OF SEQ ID NOS: 22

<210> SEQ ID NO 1
<211> LENGTH: 2495
<212> TYPE: DNA
<213> ORGANISM: Homo sapiens
<220> FEATURE:
<221> NAME/KEY: CDS
<222> LOCATION: (19)..(807)
<221> NAME/KEY: mat_peptide
<222> LOCATION: (97)..(807)
<221> NAME/KEY: sig_peptide
<222> LOCATION: (19)..(96)
<221> NAME/KEY: misc_feature
<222> LOCATION: (2429)
<223> OTHER INFORMATION: n equals a, t, g, or c

<400> SEQUENCE: 1
gccgtctctg cgttcgcc atg cgt ccc ggg gcg cca ggg cca ctc tgg cct         51
                    Met Arg Pro Gly Ala Pro Gly Pro Leu Trp Pro
                        -25                 -20 ctg ccc tgg ggg gcc ctg gct tgg gcc gtg ggc ttc gtg agc tcc atg         99
Leu Pro Trp Gly Ala Leu Ala Trp Ala Val Gly Phe Val Ser Ser Met
-15                 -10                  -5                  -1   1 ggc tcg ggg aac ccc gcg ccc ggt ggt gtt tgc tgg ctc cag cag ggc        147
Gly Ser Gly Asn Pro Ala Pro Gly Gly Val Cys Trp Leu Gln Gln Gly
                5                  10                  15 cag gag gcc acc tgc agc ctg gtg ctc cag act gat gtc acc cgg gcc        195
Gln Glu Ala Thr Cys Ser Leu Val Leu Gln Thr Asp Val Thr Arg Ala
            20                  25                  30 gag tgc tgt gcc tcc ggc aac att gac acc gcc tgg tcc aac ctc acc        243
Glu Cys Cys Ala Ser Gly Asn Ile Asp Thr Ala Trp Ser Asn Leu Thr
        35                  40                  45 cac ccg ggg aac aag atc aac ctc ctc ggc ttc ttg ggc ctt gtc cac        291
His Pro Gly Asn Lys Ile Asn Leu Leu Gly Phe Leu Gly Leu Val His
    50                  55                  60                  65 tgc ctt ccc tgc aaa gat tcg tgc gac ggc gtg gag tgc ggc ccg ggc        339
Cys Leu Pro Cys Lys Asp Ser Cys Asp Gly Val Glu Cys Gly Pro Gly
                70                  75                  80 aag gcg tgc cgc atg ctg ggg ggc cgc ccg cgc tgc gag tgc gcg ccc        387
Lys Ala Cys Arg Met Leu Gly Gly Arg Pro Arg Cys Glu Cys Ala Pro
            85                  90                  95 gac tgc tcg ggg ctc ccg gcg cgg ttg cag gtc tgc ggc tca gac ggc        435
Asp Cys Ser Gly Leu Pro Ala Arg Leu Gln Val Cys Gly Ser Asp Gly
```

```
                100                 105                 110
gcc acc tac cgc gac gag tgc gag ctg cgc gcc gcg cgc tgc cgc ggc      483
Ala Thr Tyr Arg Asp Glu Cys Glu Leu Arg Ala Ala Arg Cys Arg Gly
        115                 120                 125 cac ccg gac ctg agc gtc atg tac cgg ggc cgc tgc cgc aag tcc tgt      531
His Pro Asp Leu Ser Val Met Tyr Arg Gly Arg Cys Arg Lys Ser Cys
130                 135                 140                 145 gag cac gtg gtg tgc ccg cgg cca cag tcg tgc gtc gtg gac cag acg      579
Glu His Val Val Cys Pro Arg Pro Gln Ser Cys Val Val Asp Gln Thr
                150                 155                 160 ggc agc gcc cac tgc gtg gtg tgt cga gcg gcg ccc tgc cct gtg ccc      627
Gly Ser Ala His Cys Val Val Cys Arg Ala Ala Pro Cys Pro Val Pro
            165                 170                 175 tcc agc ccc ggc cag gag ctt tgc ggc aac aac aac gtc acc tac atc      675
Ser Ser Pro Gly Gln Glu Leu Cys Gly Asn Asn Asn Val Thr Tyr Ile
        180                 185                 190 tcc tcg tgc cac atg cgc cag gcc acc tgc ttc ctg ggc cgc tcc atc      723
Ser Ser Cys His Met Arg Gln Ala Thr Cys Phe Leu Gly Arg Ser Ile
    195                 200                 205 ggc gtg cgc cac gcg ggc agc tgc gca ggc acc cct gag gag ccg cca      771
Gly Val Arg His Ala Gly Ser Cys Ala Gly Thr Pro Glu Glu Pro Pro
210                 215                 220                 225 ggt ggt gag tct gca gaa gag gaa gag aac ttc gtg tgagcctgca           817
Gly Gly Glu Ser Ala Glu Glu Glu Glu Asn Phe Val
                230                 235 ggacaggcct gggcctggtg cccgaggccc ccatcatcc cctgttattt attgccacag      877
cagagtctaa tttatatgcc acggacactc cttagagccc ggattcggac cacttgggga    937
tcccagaacc tccctgacga tatcctggaa ggactgagga agggaggcct ggggccggc     997 tggtgggtgg gatagacctg cgttccggac actgagcgcc tgatttaggg cccttctcta    1057
ggatgcccca gccctaccc taagacctat tgccggggag gattccacac ttccgctcct     1117
ttggggataa acctattaat tattgctact atcaagaggg ctgggcattc tctgctggta    1177
attcctgaag aggcatgact gcttttctca gccccaagcc tctagtctgg gtgtgtacgg    1237
agggtctagc ctgggtgtgt acggagggtc tagcctgggt gagtacggag ggtctagcct    1297
gggtgagtac ggaggatcta gcctgggtga gtacggagag tctagcctgg gtgtgtatgg    1357
aggatctagc ctgggtgagt atggagggtc tagcctgggt gagtatggag ggtctagcct    1417
gggtgtgtat ggagggtcta gcctgggtga gtatggaggg tctagcctgg gtgtgtatgg    1477
agggtctagc ctgggtgagt atggagggtc tagcctgggt gtgtacggag ggtctagtct    1537
gagtgcgtgt ggggacctca gaacactgtg accttagccc agcaagccag gcccttcatg    1597
aaggccaaga aggctgccac cattccctgc cagcccaaga actccagctt ccccactgcc    1657
tctgtgtgcc cctttgcgtc ctgtgaaggc cattgagaaa tgcccagtgt gcccctggg     1717 aaagggcacg gcctgtgctc ctgacacggg ctgtgcttgg ccacagaacc acccagcgtc    1777
tcccctgctg ctgtccacgt cagttcatga ggcaacgtcg cgtggtctca gacgtggagc    1837
agccagcggc agctcagagc agggcactgt gtccggcgga gccaagtcca ctctggggga    1897
gctctggcgg ggaccacggg ccactgctca cccactggcc ccgagggggg tgtagacgcc    1957
aagactcacg catgtgtgac atccggagtc ctggagccgg gtgtcccagt ggcaccacta    2017
ggtgcctgct gcctccacag tggggttcac acccagggct ccttggtccc ccacaacctg    2077
cccccggcca gcctgcagac ccagactcca gccagacctg cctcacccac caatgcagcc    2137
ggggctggcg acaccagcca ggtgctggtc ttgggccagt tctcccacga cggctcaccc    2197
```

```
tcccctccat ctgcgttgat gctcagaatc gcctacctgt gcctgcgtgt aaaccacagc    2257
ctcagaccag ctatggggag aggacaacac ggaggatatc cagcttcccc ggtctggggt    2317
gaggagtgtg gggagcttgg gcatcctcct ccagcctcct ccagccccca ggcagtgcct    2377
tacctgtggt gcccagaaaa gtgccctag gttggtgggt ctacaggagc cncagccagg     2437
cagcccaccc caccctgggg ccctgcctca ccaaggaaat aaagactcaa agaagcct     2495
```

<210> SEQ ID NO 2
<211> LENGTH: 263
<212> TYPE: PRT
<213> ORGANISM: Homo sapiens

<400> SEQUENCE: 2

```
Met Arg Pro Gly Ala Pro Gly Pro Leu Trp Pro Leu Pro Trp Gly Ala
    -25             -20                 -15

Leu Ala Trp Ala Val Gly Phe Val Ser Ser Met Gly Ser Gly Asn Pro
-10                  -5                 -1   1                 5

Ala Pro Gly Gly Val Cys Trp Leu Gln Gln Gly Gln Glu Ala Thr Cys
                10                  15                  20

Ser Leu Val Leu Gln Thr Asp Val Thr Arg Ala Glu Cys Cys Ala Ser
            25                  30                  35

Gly Asn Ile Asp Thr Ala Trp Ser Asn Leu Thr His Pro Gly Asn Lys
        40                  45                  50

Ile Asn Leu Leu Gly Phe Leu Gly Leu Val His Cys Leu Pro Cys Lys
    55                  60                  65                  70

Asp Ser Cys Asp Gly Val Glu Cys Gly Pro Gly Lys Ala Cys Arg Met
                75                  80                  85

Leu Gly Gly Arg Pro Arg Cys Glu Cys Ala Pro Asp Cys Ser Gly Leu
                90                  95                  100

Pro Ala Arg Leu Gln Val Cys Gly Ser Asp Gly Ala Thr Tyr Arg Asp
            105                 110                 115

Glu Cys Glu Leu Arg Ala Ala Arg Cys Arg Gly His Pro Asp Leu Ser
        120                 125                 130

Val Met Tyr Arg Gly Arg Cys Arg Lys Ser Cys Glu His Val Val Cys
135                 140                 145                 150

Pro Arg Pro Gln Ser Cys Val Val Asp Gln Thr Gly Ser Ala His Cys
                155                 160                 165

Val Val Cys Arg Ala Ala Pro Cys Pro Val Pro Ser Ser Pro Gly Gln
            170                 175                 180

Glu Leu Cys Gly Asn Asn Asn Val Thr Tyr Ile Ser Ser Cys His Met
        185                 190                 195

Arg Gln Ala Thr Cys Phe Leu Gly Arg Ser Ile Gly Val Arg His Ala
    200                 205                 210

Gly Ser Cys Ala Gly Thr Pro Glu Pro Pro Gly Gly Glu Ser Ala
215                 220                 225                 230

Glu Glu Glu Glu Asn Phe Val
                235
```

<210> SEQ ID NO 3
<211> LENGTH: 317
<212> TYPE: PRT
<213> ORGANISM: Homo sapiens

<400> SEQUENCE: 3

Met Val Arg Ala Arg His Gln Pro Gly Gly Leu Cys Leu Leu Leu Leu

```
              1               5              10              15

Leu Leu Cys Gln Phe Met Glu Asp Arg Ser Ala Gln Ala Gly Asn Cys
                            20                  25                  30

Trp Leu Arg Gln Ala Lys Asn Gly Arg Cys Gln Val Leu Tyr Lys Thr
                        35                  40                  45

Glu Leu Ser Lys Glu Glu Cys Cys Ser Thr Gly Arg Leu Ser Thr Ser
                    50                  55                  60

Trp Thr Glu Glu Asp Val Asn Asp Asn Thr Leu Phe Lys Trp Met Ile
             65                  70                  75                  80

Phe Asn Gly Gly Ala Pro Asn Cys Ile Pro Cys Lys Glu Thr Cys Glu
                            85                  90                  95

Asn Val Asp Cys Gly Pro Gly Lys Lys Cys Arg Met Asn Lys Lys Asn
                        100                 105                 110

Lys Pro Arg Cys Val Cys Ala Pro Asp Cys Ser Asn Ile Thr Trp Lys
                        115                 120                 125

Gly Pro Val Cys Gly Leu Asp Gly Lys Thr Tyr Arg Asn Glu Cys Ala
                        130                 135                 140

Leu Leu Lys Ala Arg Cys Lys Glu Gln Pro Glu Leu Glu Val Gln Tyr
            145                 150                 155                 160

Gln Gly Arg Cys Lys Lys Thr Cys Arg Asp Val Phe Cys Pro Gly Ser
                        165                 170                 175

Ser Thr Cys Val Val Asp Gln Thr Asn Asn Ala Tyr Cys Val Thr Cys
                        180                 185                 190

Asn Arg Ile Cys Pro Glu Pro Ala Ser Ser Glu Gln Tyr Leu Cys Gly
                        195                 200                 205

Asn Asp Gly Val Thr Tyr Ser Ser Ala Cys His Leu Arg Lys Ala Thr
                        210                 215                 220

Cys Leu Leu Gly Arg Ser Ile Gly Leu Ala Tyr Glu Gly Lys Cys Ile
            225                 230                 235                 240

Lys Ala Lys Ser Cys Glu Asp Ile Gln Cys Thr Gly Gly Lys Lys Cys
                        245                 250                 255

Leu Trp Asp Phe Lys Val Gly Arg Gly Arg Cys Ser Leu Cys Asp Glu
                        260                 265                 270

Leu Cys Pro Asp Ser Lys Ser Asp Glu Pro Val Cys Ala Ser Asp Asn
                        275                 280                 285

Ala Thr Tyr Ala Ser Glu Cys Ala Met Lys Glu Ala Ala Cys Ser Ser
                        290                 295                 300

Gly Val Leu Leu Glu Val Lys His Ser Gly Ser Cys Asn
            305                 310                 315

<210> SEQ ID NO 4
<211> LENGTH: 508
<212> TYPE: DNA
<213> ORGANISM: Homo sapiens
<220> FEATURE:
<221> NAME/KEY: misc_feature
<222> LOCATION: (377)
<223> OTHER INFORMATION: n equals a, t, g, or c
<221> NAME/KEY: misc_feature
<222> LOCATION: (379)
<223> OTHER INFORMATION: n equals a, t, g, or c
<221> NAME/KEY: misc_feature
<222> LOCATION: (428)
<223> OTHER INFORMATION: n equals a, t, g, or c
<221> NAME/KEY: misc_feature
<222> LOCATION: (439)
<223> OTHER INFORMATION: n equals a, t, g, or c
<221> NAME/KEY: misc_feature
<222> LOCATION: (444)
```

```
<223> OTHER INFORMATION: n equals a, t, g, or c
<221> NAME/KEY: misc_feature
<222> LOCATION: (452)
<223> OTHER INFORMATION: n equals a, t, g, or c
<221> NAME/KEY: misc_feature
<222> LOCATION: (461)
<223> OTHER INFORMATION: n equals a, t, g, or c
<221> NAME/KEY: misc_feature
<222> LOCATION: (466)
<223> OTHER INFORMATION: n equals a, t, g, or c
<221> NAME/KEY: misc_feature
<222> LOCATION: (468)
<223> OTHER INFORMATION: n equals a, t, g, or c
<221> NAME/KEY: misc_feature
<222> LOCATION: (470)
<223> OTHER INFORMATION: n equals a, t, g, or c
<221> NAME/KEY: misc_feature
<222> LOCATION: (475)
<223> OTHER INFORMATION: n equals a, t, g, or c
<221> NAME/KEY: misc_feature
<222> LOCATION: (485)
<223> OTHER INFORMATION: n equals a, t, g, or c
<221> NAME/KEY: misc_feature
<222> LOCATION: (501)
<223> OTHER INFORMATION: n equals a, t, g, or c
<221> NAME/KEY: misc_feature
<222> LOCATION: (505)
<223> OTHER INFORMATION: n equals a, t, g, or c
<221> NAME/KEY: misc_feature
<222> LOCATION: (399)
<223> OTHER INFORMATION: n equals a, t, g or c

<400> SEQUENCE: 4
aattcggcac gagtttctca gccccaagcc tctagtctgg gtgtgtacgg agggtctagc      60
ctgggtgtgt acggagggtc tagcctgggt gagtacggag ggtctagcct gggtgagtac     120
ggagggtcta gcctgggtga gtacggagag tctagcctgg gtgtgtatgg aggatctagc     180
ctgggtgagt atggagggtc tagcctgggt gagtatggag ggtctagcct gggtgtgtat     240
ggagggtcta gcctgggtga gtatggaggg tctagcctgg gtgtgtatgg agggtctagc     300
ctgggtgagt atggagggtc tagccttggt gtttacggag gtctagtct gagttcgttt      360 tggggacctc agaacantnt taacctttag cccagnaanc caggcccttta atgaaggcca    420 gaaggttnca ccattcctnc cctnccaaga antcaatttc nnaatncntn ttgtnccctt     480
ttggnccttt aagccattta naatncca                                        508

<210> SEQ ID NO 5
<211> LENGTH: 466
<212> TYPE: DNA
<213> ORGANISM: Homo sapiens
<220> FEATURE:
<221> NAME/KEY: misc_feature
<222> LOCATION: (415)
<223> OTHER INFORMATION: n equals a, t, g, or c
<221> NAME/KEY: misc_feature
<222> LOCATION: (422)
<223> OTHER INFORMATION: n equals a, t, g, or c
<221> NAME/KEY: misc_feature
<222> LOCATION: (437)
<223> OTHER INFORMATION: n equals a, t, g, or c
<221> NAME/KEY: misc_feature
<222> LOCATION: (449)
<223> OTHER INFORMATION: n equals a, t, g, or c

<400> SEQUENCE: 5
ggcgacggcg tggagtgcgg cccgggcaag gcgtgccgca tgctgggggg ccgcccgcgc      60
tgcgagtgcg cgcccgactg ctcggggctc ccggcgcggt tgcaggtctg cggctcagac     120
ggcgccacct accgcgacga gtgcgagctg cgcgccgcgc gctgccgcgg ccacccggac     180
```

| | |
|---|---|
| ctgagcgtca tgtaccgggg ccgctgccgc aagtcctgtg agcacgtggt gtgcccgcgg | 240 |
| ccacagtcgt gcgtcgtgga ccagacgggc agcgcccact gcgtggtgtg tcgaagcggc | 300 |
| gccctgccct gtgccctcca gccccggcca ggagctttgc ggccaacaac aaagttacct | 360 |
| aaatttcttc gtgccaaatg cgccaaggcc aactgcttcc tgggccggtt ccatnnggcg | 420 |
| tncgccaagc gggcaanttt cgcaagcanc cctgaaggag ccgcca | 466 |

<210> SEQ ID NO 6
<211> LENGTH: 337
<212> TYPE: DNA
<213> ORGANISM: Homo sapiens
<220> FEATURE:
<221> NAME/KEY: misc_feature
<222> LOCATION: (33)
<223> OTHER INFORMATION: n equals a, t, g, or c
<221> NAME/KEY: misc_feature
<222> LOCATION: (60)
<223> OTHER INFORMATION: n equals a, t, g, or c
<221> NAME/KEY: misc_feature
<222> LOCATION: (92)..(93)
<223> OTHER INFORMATION: n equals a, t, g, or c
<221> NAME/KEY: misc_feature
<222> LOCATION: (141)
<223> OTHER INFORMATION: n equals a, t, g, or c
<221> NAME/KEY: misc_feature
<222> LOCATION: (264)
<223> OTHER INFORMATION: n equals a, t, g, or c
<221> NAME/KEY: misc_feature
<222> LOCATION: (129)
<223> OTHER INFORMATION: n equals a, t, g or c

<400> SEQUENCE: 6

| | |
|---|---|
| cttgagtgcg tgtggggacc tcagaacact gtnaccttag cccagcaagc caggcccttn | 60 |
| atgaaggcca agaaggctgc caccattccc tnncagccca agaactccag cttccccact | 120 |
| gcctcttnt gccccttgc ntcctgtgaa ggccattgag aaatgcccag tgtgccccct | 180 |
| gggaagggc acggcctgtg ctcctgacac gggctgtgct tggccacaga accacccagc | 240 |
| gtctcccctg ctgctgtcca cgtnagttca tgaggcaacg tcgcgtggtc ttcagacgtg | 300 |
| ggagcagcca gcggcagctc aggaggcagg gcactgt | 337 |

<210> SEQ ID NO 7
<211> LENGTH: 298
<212> TYPE: DNA
<213> ORGANISM: Homo sapiens
<220> FEATURE:
<221> NAME/KEY: misc_feature
<222> LOCATION: (5)
<223> OTHER INFORMATION: n equals a, t, g, or c
<221> NAME/KEY: misc_feature
<222> LOCATION: (11)
<223> OTHER INFORMATION: n equals a, t, g, or c
<221> NAME/KEY: misc_feature
<222> LOCATION: (68)
<223> OTHER INFORMATION: n equals a, t, g, or c
<221> NAME/KEY: misc_feature
<222> LOCATION: (70)
<223> OTHER INFORMATION: n equals a, t, g, or c
<221> NAME/KEY: misc_feature
<222> LOCATION: (84)
<223> OTHER INFORMATION: n equals a, t, g, or c
<221> NAME/KEY: misc_feature
<222> LOCATION: (111)
<223> OTHER INFORMATION: n equals a, t, g, or c
<221> NAME/KEY: misc_feature
<222> LOCATION: (186)
<223> OTHER INFORMATION: n equals a, t, g, or c
<221> NAME/KEY: misc_feature
<222> LOCATION: (243)
<223> OTHER INFORMATION: n equals a, t, g, or c

```
<221> NAME/KEY: misc_feature
<222> LOCATION: (266)
<223> OTHER INFORMATION: n equals a, t, g, or c
<221> NAME/KEY: misc_feature
<222> LOCATION: (272)
<223> OTHER INFORMATION: n equals a, t, g, or c
<221> NAME/KEY: misc_feature
<222> LOCATION: (280)
<223> OTHER INFORMATION: n equals a, t, g, or c
<221> NAME/KEY: misc_feature
<222> LOCATION: (288)
<223> OTHER INFORMATION: n equals a, t, g, or c

<400> SEQUENCE: 7
ggcanagccg nctggtgggt gggatagacc tgctttccgg acactgagcg cctgatttag      60
ggcccttntn taggaatgcc ccancccta ccctaagacc tattgccggg naggattcca     120
cacttccgct cctttgggga taaacctatt aattattgct actatcaaga gggctggggc    180
attctntgct ggtaaattcc tgaagaggca tgactgcttt tttaagcccc aagcctctag    240
ttntgggtgt tttacggagg ggtctnagcc tngggttgtn gtacgggngg ggttctta     298

<210> SEQ ID NO 8
<211> LENGTH: 186
<212> TYPE: DNA
<213> ORGANISM: Homo sapiens
<220> FEATURE:
<221> NAME/KEY: misc_feature
<222> LOCATION: (34)
<223> OTHER INFORMATION: n equals a, t, g, or c
<221> NAME/KEY: misc_feature
<222> LOCATION: (128)
<223> OTHER INFORMATION: n equals a, t, g, or c
<221> NAME/KEY: misc_feature
<222> LOCATION: (155)..(156)
<223> OTHER INFORMATION: n equals a, t, g, or c
<221> NAME/KEY: misc_feature
<222> LOCATION: (180)
<223> OTHER INFORMATION: n equals a, t, g, or c

<400> SEQUENCE: 8
ccggcggagc aaagtccact ctgggggagc tctngcgggg accacgggcc actgctcacc     60
cactggcccc gagggggtg tagacgccaa gactcacgca tgtttgacat ccggagtcct    120
ggagccgngt gtcccagtgg caccactagg tgctnnctgc ctccacagtg gggttcacan   180
ccaggg                                                              186

<210> SEQ ID NO 9
<211> LENGTH: 308
<212> TYPE: DNA
<213> ORGANISM: Homo sapiens
<220> FEATURE:
<221> NAME/KEY: misc_feature
<222> LOCATION: (3)
<223> OTHER INFORMATION: n equals a, t, g, or c
<221> NAME/KEY: misc_feature
<222> LOCATION: (19)
<223> OTHER INFORMATION: n equals a, t, g, or c
<221> NAME/KEY: misc_feature
<222> LOCATION: (24)
<223> OTHER INFORMATION: n equals a, t, g, or c
<221> NAME/KEY: misc_feature
<222> LOCATION: (29)
<223> OTHER INFORMATION: n equals a, t, g, or c
<221> NAME/KEY: misc_feature
<222> LOCATION: (34)
<223> OTHER INFORMATION: n equals a, t, g, or c
<221> NAME/KEY: misc_feature
<222> LOCATION: (38)
<223> OTHER INFORMATION: n equals a, t, g, or c
<221> NAME/KEY: misc_feature
```

```
<222> LOCATION: (40)
<223> OTHER INFORMATION: n equals a, t, g, or c
<221> NAME/KEY: misc_feature
<222> LOCATION: (50)
<223> OTHER INFORMATION: n equals a, t, g, or c
<221> NAME/KEY: misc_feature
<222> LOCATION: (83)
<223> OTHER INFORMATION: n equals a, t, g, or c
<221> NAME/KEY: misc_feature
<222> LOCATION: (107)
<223> OTHER INFORMATION: n equals a, t, g, or c
<221> NAME/KEY: misc_feature
<222> LOCATION: (205)
<223> OTHER INFORMATION: n equals a, t, g, or c
<221> NAME/KEY: misc_feature
<222> LOCATION: (220)
<223> OTHER INFORMATION: n equals a, t, g, or c
<221> NAME/KEY: misc_feature
<222> LOCATION: (237)
<223> OTHER INFORMATION: n equals a, t, g, or c
<221> NAME/KEY: misc_feature
<222> LOCATION: (272)
<223> OTHER INFORMATION: n equals a, t, g, or c
<221> NAME/KEY: misc_feature
<222> LOCATION: (242)
<223> OTHER INFORMATION: n equals a, t, g, or c
<221> NAME/KEY: misc_feature
<222> LOCATION: (297)
<223> OTHER INFORMATION: n equals a, t, g, or c
<221> NAME/KEY: misc_feature
<222> LOCATION: (308)
<223> OTHER INFORMATION: n equals a, t, g, or c

<400> SEQUENCE: 9
ggnagaggtg acaccagcna ggtnctgtnt tggnccantn ctcccacgan ggctcaccct      60
cccctccatc tgctttaatg ctncgaatcg cctacctgtg ccctgcntgt aaaccacagc     120
tttcaaacca gctatgggga gaggacaaca cggaggatat tccagcttcc ccggtctggg     180
gtgaaggagt gtggggagct tgggncatcc tcctccagtn tcctccagcc cccaggnagt     240
gnctttaanc tgtgggttgc ccagaaaagt gnccctagg  tttgttgggt tttaaangga     300 gctttaan                                                              308

<210> SEQ ID NO 10
<211> LENGTH: 407
<212> TYPE: DNA
<213> ORGANISM: Homo sapiens
<220> FEATURE:
<221> NAME/KEY: misc_feature
<222> LOCATION: (290)
<223> OTHER INFORMATION: n equals a, t, g, or c
<221> NAME/KEY: misc_feature
<222> LOCATION: (298)
<223> OTHER INFORMATION: n equals a, t, g, or c
<221> NAME/KEY: misc_feature
<222> LOCATION: (324)
<223> OTHER INFORMATION: n equals a, t, g, or c
<221> NAME/KEY: misc_feature
<222> LOCATION: (326)
<223> OTHER INFORMATION: n equals a, t, g, or c
<221> NAME/KEY: misc_feature
<222> LOCATION: (386)
<223> OTHER INFORMATION: n equals a, t, g, or c
<221> NAME/KEY: misc_feature
<222> LOCATION: (402)
<223> OTHER INFORMATION: n equals a, t, g, or c
<221> NAME/KEY: misc_feature
<222> LOCATION: (407)
<223> OTHER INFORMATION: n equals a, t, g, or c

<400> SEQUENCE: 10
ggcacgagcc tgggtgtgta cggagggtct agtctgagtg cgtgtggggc ctcagaacac      60
```

```
tgtgacctta gcccagcaag ccaggccttc atgaaggcaa gaaggtgcca ccattccctg    120
ccagcccaag actccagttc cccactgcct ctgtgtgccc tttgcgtcct gtgaagccat    180
tgagaaatgc ccatgtgccc ctgggaaagg gcacggctgt gtcctgacag ggtgtgtttg    240
cacagaccac caggtttcct gtgtgtcagt attatgagga acgtcggtgn ttagagtnga    300
gcagcaggga gttagagcag gatntntccg gggcaagtcc attttggggt tttgcggaca    360
gggcatgtta ccattgcccg aggggntaga gcagttagat tntgaan                 407
```

<210> SEQ ID NO 11
<211> LENGTH: 139
<212> TYPE: DNA
<213> ORGANISM: Homo sapiens
<220> FEATURE:
<221> NAME/KEY: misc_feature
<222> LOCATION: (2)
<223> OTHER INFORMATION: n equals a, t, g, or c
<221> NAME/KEY: misc_feature
<222> LOCATION: (9)
<223> OTHER INFORMATION: n equals a, t, g, or c
<221> NAME/KEY: misc_feature
<222> LOCATION: (11)
<223> OTHER INFORMATION: n equals a, t, g, or c
<221> NAME/KEY: misc_feature
<222> LOCATION: (45)
<223> OTHER INFORMATION: n equals a, t, g, or c
<221> NAME/KEY: misc_feature
<222> LOCATION: (70)
<223> OTHER INFORMATION: n equals a, t, g, or c
<221> NAME/KEY: misc_feature
<222> LOCATION: (105)
<223> OTHER INFORMATION: n equals a, t, g, or c
<221> NAME/KEY: misc_feature
<222> LOCATION: (131)
<223> OTHER INFORMATION: n equals a, t, g, or c
<221> NAME/KEY: misc_feature
<222> LOCATION: (137)
<223> OTHER INFORMATION: n equals a, t, g, or c

<400> SEQUENCE: 11

```
anccagggnt ncttggtccc ccacaacctt ccccggccag gcctncagac ccagacttca     60
gccagacctn ccttaaccac caatgcagcc ggggcttgcg acaanagcag gtgctggtct    120
tggggcagtt nttccangg                                                 139
```

<210> SEQ ID NO 12
<211> LENGTH: 25
<212> TYPE: DNA
<213> ORGANISM: Homo sapiens

<400> SEQUENCE: 12

```
tcacgccata tgggctcggg gaacc                                           25
```

<210> SEQ ID NO 13
<211> LENGTH: 41
<212> TYPE: DNA
<213> ORGANISM: Homo sapiens

<400> SEQUENCE: 13

```
catccgggta ccttattaca cgaagttctc ttcctcttct g                         41
```

<210> SEQ ID NO 14
<211> LENGTH: 40
<212> TYPE: DNA
<213> ORGANISM: Homo sapiens

<400> SEQUENCE: 14

-continued

```
catcgcggat ccgccatcat gcgtcccggg gcgccagggc                    40

<210> SEQ ID NO 15
<211> LENGTH: 38
<212> TYPE: DNA
<213> ORGANISM: Homo sapiens

<400> SEQUENCE: 15
catccgggta cctcacacga agttctcttc ctcttctg                      38

<210> SEQ ID NO 16
<211> LENGTH: 40
<212> TYPE: DNA
<213> ORGANISM: Homo sapiens

<400> SEQUENCE: 16
catcgcggat ccgccaccat gcgtcccggg gcgccagggc                    40

<210> SEQ ID NO 17
<211> LENGTH: 35
<212> TYPE: DNA
<213> ORGANISM: Homo sapiens

<400> SEQUENCE: 17
tcaccgctcg agcacgaagt tctcttcctc ttctg                         35

<210> SEQ ID NO 18
<211> LENGTH: 40
<212> TYPE: DNA
<213> ORGANISM: Homo sapiens

<400> SEQUENCE: 18
catcgcggat ccgccaccat gcgtcccggg gcgccagggc                    40

<210> SEQ ID NO 19
<211> LENGTH: 38
<212> TYPE: DNA
<213> ORGANISM: Homo sapiens

<400> SEQUENCE: 19
catccgggta cctcacacga agttctcttc ctcttctg                      38

<210> SEQ ID NO 20
<211> LENGTH: 9
<212> TYPE: PRT
<213> ORGANISM: Primer_Bind
<220> FEATURE:
<223> OTHER INFORMATION: Description of Artificial Sequence:
      hemaglutanin tag

<400> SEQUENCE: 20

Tyr Pro Tyr Asp Val Pro Asp Tyr Ala
 1               5

<210> SEQ ID NO 21
<211> LENGTH: 8
<212> TYPE: PRT
<213> ORGANISM: Primer_Bind
<220> FEATURE:
<223> OTHER INFORMATION: Description of Artificial Sequence: Myc tag

<400> SEQUENCE: 21

Asp Tyr Lys Asp Asp Asp Asp Lys
 1               5
```

-continued

```
<210> SEQ ID NO 22
<211> LENGTH: 10
<212> TYPE: PRT
<213> ORGANISM: Primer_Bind
<220> FEATURE:
<223> OTHER INFORMATION: Description of Artificial Sequence: Myc tag

<400> SEQUENCE: 22

Glu Gln Lys Leu Ile Ser Glu Glu Asp Leu
1               5                   10
```